United States Patent
González-Canudas

(10) Patent No.: US 11,951,081 B2
(45) Date of Patent: Apr. 9, 2024

(54) METFORMIN GLYCINATE, PHARMACEUTICAL COMPOSITIONS COMPRISING THE SAME, AND METHODS OF USING THE SAME

(71) Applicant: Laboratorios Silanes S.A. DE C.V., Cdmx (MX)

(72) Inventor: Jorge González-Canudas, Mexico City (MX)

(73) Assignee: LABORATORIOS SILANES S.A. DE C.V., Mexico City (MX)

( * ) Notice: Subject to any disclaimer, the term of this patent is extended or adjusted under 35 U.S.C. 154(b) by 228 days.

(21) Appl. No.: 17/516,961

(22) Filed: Nov. 2, 2021

(65) Prior Publication Data
US 2022/0296539 A1   Sep. 22, 2022

Related U.S. Application Data

(62) Division of application No. 16/337,984, filed as application No. PCT/IB2017/056031 on Sep. 29, 2017, now Pat. No. 11,185,516.

(60) Provisional application No. 62/402,924, filed on Sep. 30, 2016.

(51) Int. Cl.
| | |
|---|---|
| A61K 31/155 | (2006.01) |
| A61K 9/00 | (2006.01) |
| A61K 31/135 | (2006.01) |
| A61K 31/17 | (2006.01) |
| A61K 31/403 | (2006.01) |
| A61K 31/4439 | (2006.01) |
| A61K 31/444 | (2006.01) |
| A61K 31/495 | (2006.01) |
| A61K 31/4985 | (2006.01) |
| A61K 31/513 | (2006.01) |
| A61K 31/522 | (2006.01) |
| A61K 31/573 | (2006.01) |
| A61K 38/22 | (2006.01) |
| A61K 38/28 | (2006.01) |
| A61P 3/10 | (2006.01) |

(52) U.S. Cl.
CPC .......... *A61K 31/155* (2013.01); *A61K 9/0053* (2013.01); *A61K 31/135* (2013.01); *A61K 31/17* (2013.01); *A61K 31/403* (2013.01); *A61K 31/4439* (2013.01); *A61K 31/444* (2013.01); *A61K 31/495* (2013.01); *A61K 31/4985* (2013.01); *A61K 31/513* (2013.01); *A61K 31/522* (2013.01); *A61K 31/573* (2013.01); *A61K 38/22* (2013.01); *A61K 38/28* (2013.01); *A61P 3/10* (2018.01)

(58) Field of Classification Search
CPC .................................................. A61K 31/155
See application file for complete search history.

(56) References Cited

U.S. PATENT DOCUMENTS

| | | | |
|---|---|---|---|
| 3,903,141 A | 9/1975 | Just et al. | |
| 3,957,853 A | 5/1976 | Bohuon | |
| 4,028,402 A | 6/1977 | Fischer et al. | |
| 4,835,184 A | 5/1989 | Hugelin et al. | |
| 8,703,183 B2 * | 4/2014 | Lara .......................... | A61P 3/10 514/483 |
| 8,853,259 B2 | 10/2014 | Mylari | |
| 2002/0040063 A1 | 4/2002 | Chandran et al. | |
| 2002/0147226 A1 * | 10/2002 | Smith .................... | A61K 31/44 514/342 |
| 2005/0158374 A1 | 7/2005 | Wong et al. | |
| 2008/0031964 A1 | 2/2008 | Messadek | |
| 2010/0004304 A1 | 1/2010 | Kohn et al. | |
| 2011/0171142 A1 | 7/2011 | Lara | |
| 2012/0219623 A1 | 8/2012 | Meinicke | |
| 2014/0018419 A1 | 1/2014 | Mylari et al. | |
| 2016/0101082 A1 | 4/2016 | Kiyono et al. | |
| 2017/0119841 A1 | 5/2017 | Mathias et al. | |
| 2020/0022930 A1 | 1/2020 | González-Canudas | |
| 2020/0222343 A1 | 7/2020 | González-Canudas | |

FOREIGN PATENT DOCUMENTS

| | | |
|---|---|---|
| WO | WO 2005/065675 | 7/2005 |
| WO | WO 2006/086856 | 8/2006 |
| WO | WO 2008/061456 | 5/2008 |
| WO | WO 2008/093984 | 8/2008 |
| WO | WO 2009/038396 | 3/2009 |
| WO | WO 2009/144527 | 12/2009 |
| WO | WO 2011/051974 | 5/2011 |
| WO | WO 2018/060959 | 4/2018 |
| WO | WO 2018/060962 A2 | 4/2018 |

OTHER PUBLICATIONS

Bogan, J.S., et al., "Functional cloning of TUG as a regulator of GLUT4 glucose transporter trafficking," *Nature* 425:727-733, 2003, Nature Publishing Group, United Kingdom.

Fioranelli, M., et al., "Twenty-five years of studies and trials for the therapeutic application of IL-10 immunomodulating properties. From high doses administration to low dose medicine new paradigm," *J. Integr. Cardio.* 1(1):2-6, 2014, Open Access Text, United Kingdom.

Galadari, S., et al., "Role of ceramide in diabetes mellitus: evidence and mechanisms," *Lipids Health Disease* 12:98-114, 2013, Springer Nature, United States.

(Continued)

*Primary Examiner* — Rei Tsang Shiao
(74) *Attorney, Agent, or Firm* — Hudak, Shunk & Farine Co. LPA

(57) ABSTRACT

The present disclosure relates to metformin glycinate and methods of using metformin glycinate for the treatment of diseases including diabetes mellitus, obesity, dyslipidemia, diseases associated with IL-10 up-regulation, and diseases or disorders associated with elevated or increased ceramide levels. Pharmaceutical formulations comprising metformin glycinate are also disclosed.

18 Claims, 22 Drawing Sheets

(56) References Cited

OTHER PUBLICATIONS

Granero, F., et al., "A human-specific TNF-responsive promoter for Goodpasture antigen-binding protein," *FEBS Journal* 272:5291-5305, 2005, John Wiley & Sons, United States.

Granero-Moltó, F., et al., "Goodpasture Antigen-binding Protein and Its Spliced Variant, Ceramide Transfer Protein, Have Different Functions in the Modulation of Apoptosis during Zebrafish Development," *J. Biol. Chem.* 283(29):20495-20504, 2008, American Society for Biochemistry and Molecular Biology, Inc., United States.

Hla, T., et al., "C16:0-Ceramide Signals Insulin Resistance," *Cell Metab.* 20:703-705, 2014, Elsevier Inc., United States.

Jembrek, M.J., et al., "Ceramides in Alzheimer's Disease: Key Mediators of Neuronal Apoptosis Induced by Oxidative Stress and Aβ Accumulation," *Oxidative Med. Cell. Longevity* 2015:1-17, 2015, Hindawi Publishing Corporation, Egypt.

Kramer, H.F., et al., "AS160 Regulates Insulin-and Contraction-stimulated Glucose Uptake in Mouse Skeletal Muscle," *J. Biol. Chem.* 281(42):31478-31485, American Society for Biochemistry and Molecular Biology, Inc., United States.

Lee, J.O., et al., "Metformin Regulates Glucose Transporter 4 (GLUT4) Translocation through AMP-activated Protein Kinase (AMPK)-mediated Cbl/CAP Signaling in 3T3-L1 Preadipocyte Cells," *J. Biol. Chem.* 287(53):44121-44129, 2012, American Society for Biochemistry and Molecular Biology, Inc., United States.

Miralem, T., et al., "Human Biliverdin Reductase Suppresses Goodpasture Antigen-binding Protein (GPBP) Kinase Activity," *J. Biol. Chem.* 285(17):12551-12558, 2010, American Society for Biochemistry and Molecular Biology, Inc., United States.

Mosser, D.M., et al., "Interleukin-10: new perspectives on an old cytokine," *Immunol. Rev.* 226:205-218, 2008, Blackwell Munksgaard, United Kingdom.

Raya, A., et al., "Characterization of a Novel Type of Serine/Threonine Kinase That Specifically Phosphorylates the Human Goodpasture Antigen," *J. Biol. Chem.* 274(18):12642-12649, 1999, American Society for Biochemistry and Molecular Biology, Inc., United States.

Raya, A., et al., "Goodpasture Antigen-binding Protein, the Kinase That Phosphorylates the Goodpasture Antigen, Is an Alternatively Spliced Variant Implicated in Autoimmune Pathogenesis," *J. Biol. Chem.* 275(51):40392-40399, 2000, American Society for Biochemistry and Molecular Biology, Inc., United States.

Revert, F., et al., "Goodpasture Antigen-binding Protein Is a Soluble Exportable Protein that Interacts with Type IV Collagen," *J. Biol. Chem.* 283(44):30246-30255, 2008, American Society for Biochemistry and Molecular Biology, Inc., United States.

Sawada, M., et al., "Molecular mechanisms of TNF-α-induced ceramide formation in human glioma cells: P53-mediated oxidant stress-dependent and -independent pathways," *Cell Death Differentiation* 11:997-1008, 2004, Nature Publishing Group, United Kingdom.

Sharma, K., et al., "The yins and yangs of ceramide," *Cell Res.* 9:1-10, 1999, Nature Publishing Group, United Kingdom.

Turpin, S.M., et al., "Obesity-Induced CerS6-Dependent C16:0 Ceramide Production Promotes Weight Gain and Glucose Intolerance," *Cell Metab.* 20:678-686, 2014, Elsevier, Inc., United States.

Xia, J.Y., et al., "The adipokine/ceramide axis: Key aspects of insulin sensitization," *Biochimie* 96:130-139, 2014, Elsevier, Inc., United States.

Brunmair, B., et al., "Thiazolidinediones, Like Metformin, Inhibit Respiratory Complex I: A Common Mechanism Contributing to Their Antidiabetic Actions?" *Diabetes* 53:1052-1059, 2004, American Diabetes Association, United States.

Buzzai, M., et al., "Systemic Treatment with the Antidiabetic Drug Metformin Selectively Impairs p53-Deficient Tumor Cell Growth," *Cancer Res.* 67(14):6745-6752, 2007, Science Publishing Group, United States.

Hardie, D.G., "Neither LKB1 Nor AMPK Are the Direct Targets of Metformin," *Gastroenterology* 131:973, 2006, Elsevier, Netherlands.

Kim, Y.D., et al., "Metformin Inhibits Hepatic Gluconeogenesis Through AMP-Activated Protein Kinase-Dependent Regulation of the Orphan Nuclear Receptor SHP," *Diabetes* 57:307-314, 2008, American Diabetes Association, United States.

Natali, A., et al., "Effects of metformin and thiazolidinediones on suppression of hepatic glucose production and stimulation of glucose update in type 2 diabetes: a systematic review," *Diabetologia* 49:434-441, 2006, Springer-Verlag, Germany.

Ouyang, J., et al., "Metformin Activates AMP Kinase through Inhibition of AMP Deaminase," *J. Biol. Chem.* 286(1):1-11, 2011, American Society for Biochemistry and Molecular Biology, Inc., United States.

Zhang, Y., et al., "Metformin interacts with AMPK through binding to γ subunit," *Mol. Cell Biochem.* 368:69-76, 2012, Springer Science+Business Media, LLC, United States.

International Search Report and Written Opinion for International Application No. PCT/IB2017/056031, ISA/US, Commissioner for Patents, Alexandria, Virginia, dated Jan. 17, 2018, 12 pages.

International Search Report and Written Opinion for International Application No. PCT/IB2017/056034, ISA/US, Commissioner for Patents, Alexandria, Virginia, dated Apr. 12, 2018, 8 pages.

Office Action dated Oct. 14, 2020, in U.S. Appl. No. 16/337,994, Gonzalez-Canudas, J. et al., filed Mar. 29, 2019, 12 pages.

Office Action dated Apr. 22, 2021, in U.S. Appl. No. 16/337,994, Gonzalez-Canudas, J. et al., filed Mar. 29, 2019, 17 pages.

Mencarelli, Chiara, et al. "Goodpasture antigen-binding protein/ceramide transporter binds to human serum amyloid P-component and is present in brain amyloid plaques." Journal of Biological Chemistry 287(18): 14897-14911. (2012).

Scotland, S., et al. "Mitochondrial energetic and AKT status mediate metabolic effects and apoptosis of metformin in human leukemic cells." Leukemia 27(11): 2129-2138. (2013).

Rena, Graham, Ewan R. Pearson, and Kei Sakamoto. "Molecular mechanism of action of metformin: old or new insights?." Diabetologia 56(9): 1898-1906. (2013).

Park, S-I, et al., "A fixed-dose combination tablet of gemigliptin and metformin sustained release has comparable pharmacodynamic, pharmacokinetic, and tolerability profiles to separate tablets in healthy subjects," Drug Des. Devel. Ther. 9: 729-736, 735 (2015) (available at https://www.ncbi.nlm.nih.gov/pmc/articles/PMC4324327/).

* cited by examiner

FIGURE 1. Treatment with Metformin Glycinate Reduces Blood A1C Levels in Type 2 Diabetic Patients
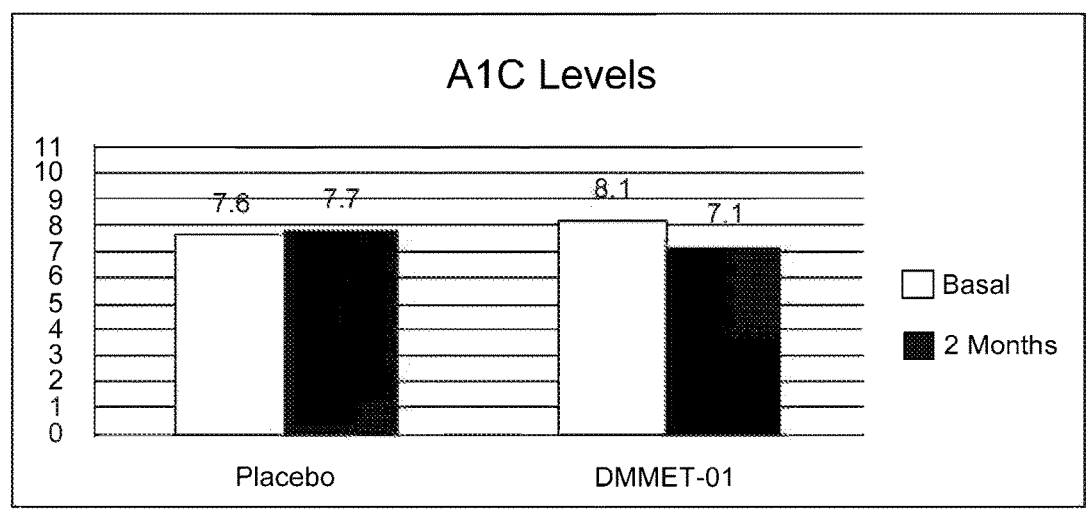

FIGURE 2. Plasma Metformin Glycinate Concentration after Administration with and without Food
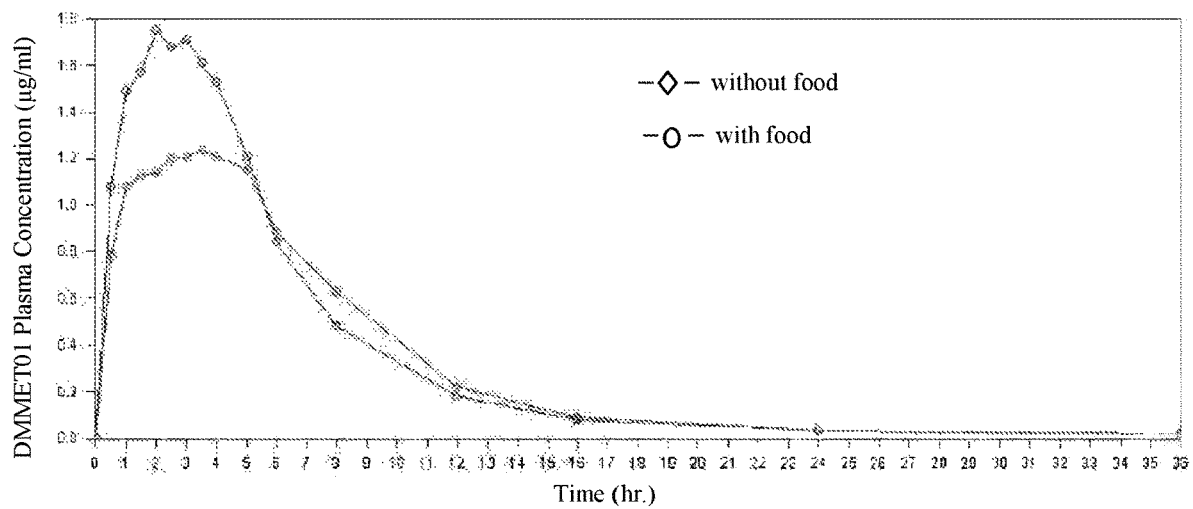

FIGURE 3. Metformin Glycinate Inhibits IL-10 Expression in Macrophages Activated by LPS and INF-γ
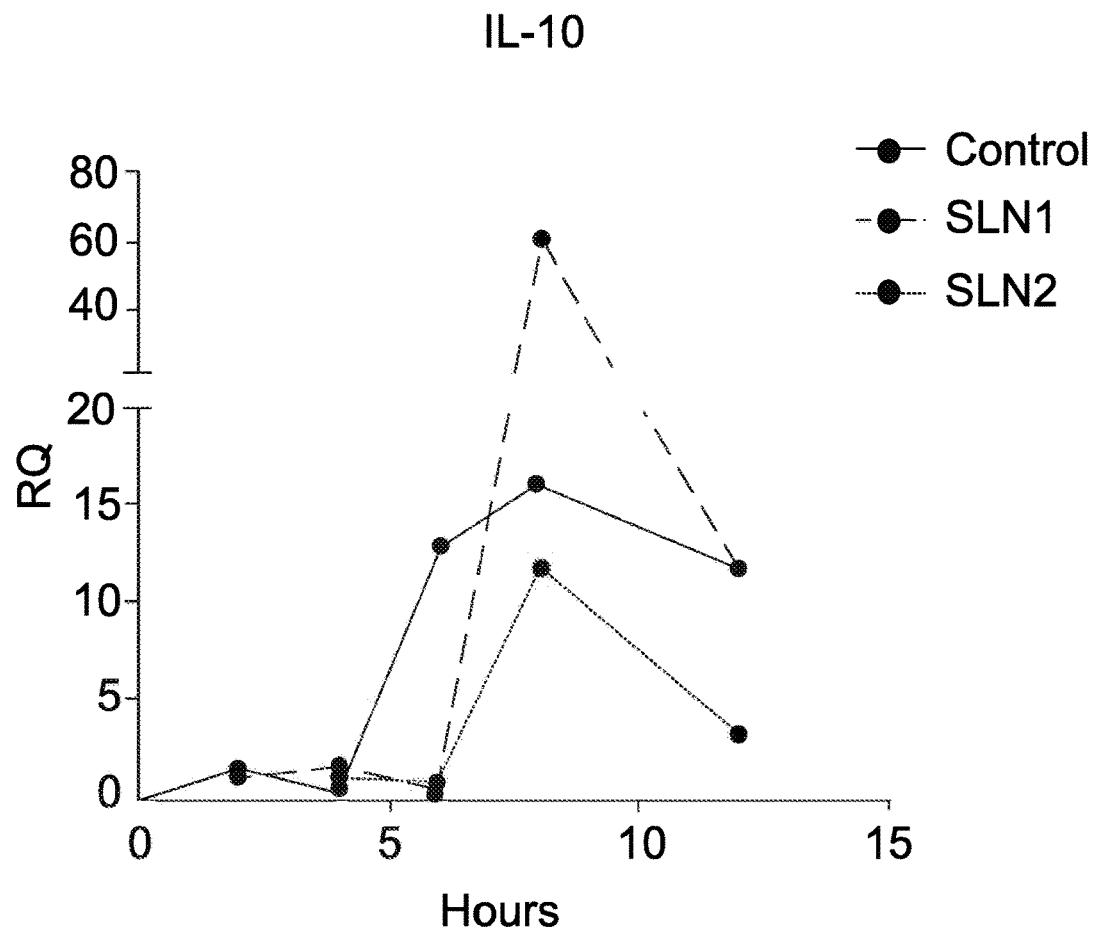
|  | Control | SLN1 | SLN2 |
|---|---|---|---|
| AUC | 100.7 | 206.6 | 46.54 |

FIGURE 4. Metformin Glycinate Inhibits the Growth of Cancer Cells
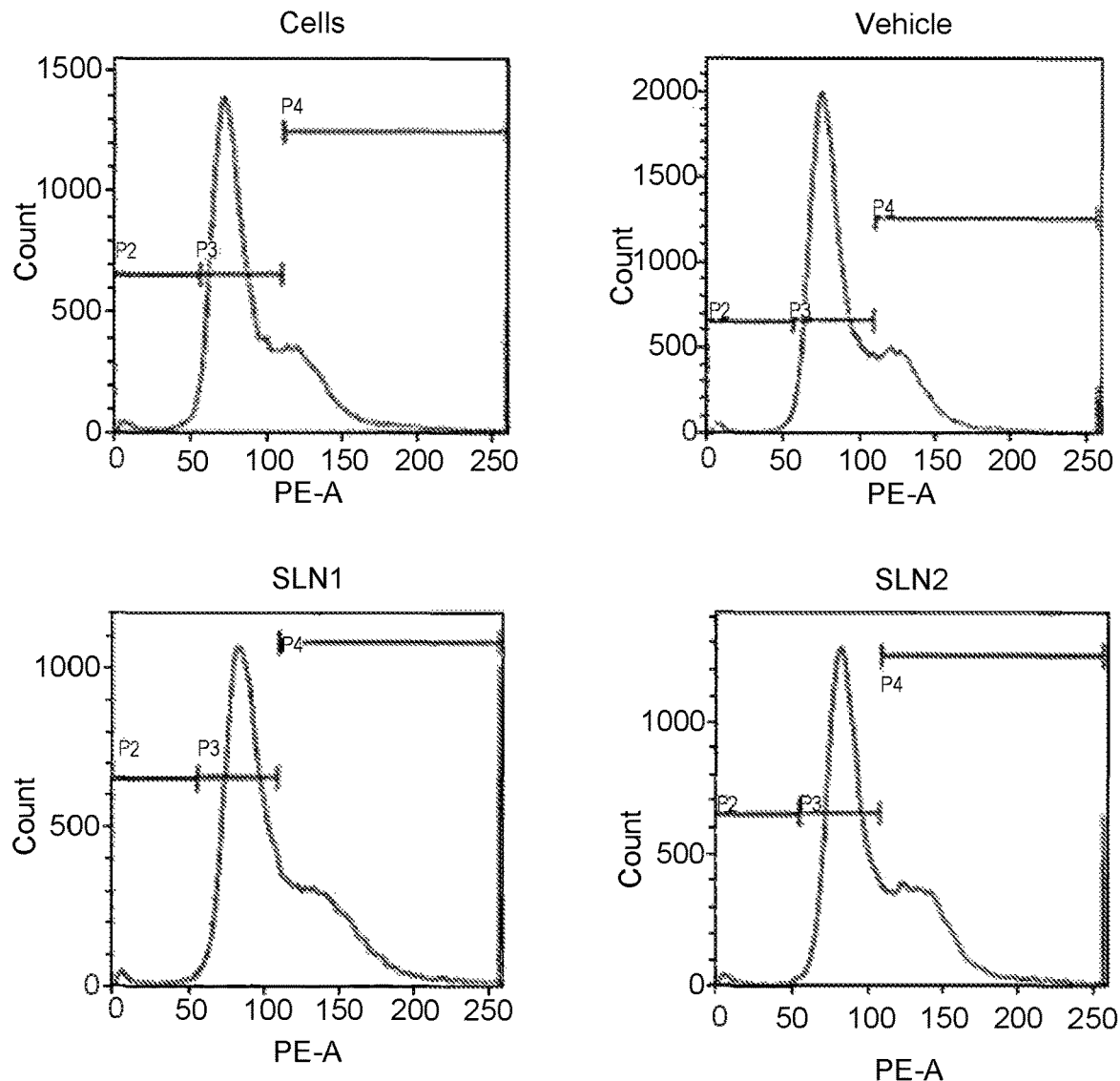
|  | P2 (sub-G0/G1) | P3 (G1) | P4 (S/G2/M) |
| --- | --- | --- | --- |
| Cells | 5.37% | 65.30% | 19.24% |
| Vehicle | 3.40% | 68.92% | 23.29% |
| SLN1 | 1.92% | 50.95% | 28.42% |
| SLN2 | 1.83% | 55.65% | 30.67% |

FIGURE 5. Metformin Glycinate Reduces Fasting Serum Leptin Levels in IRS2 Knockout Mice
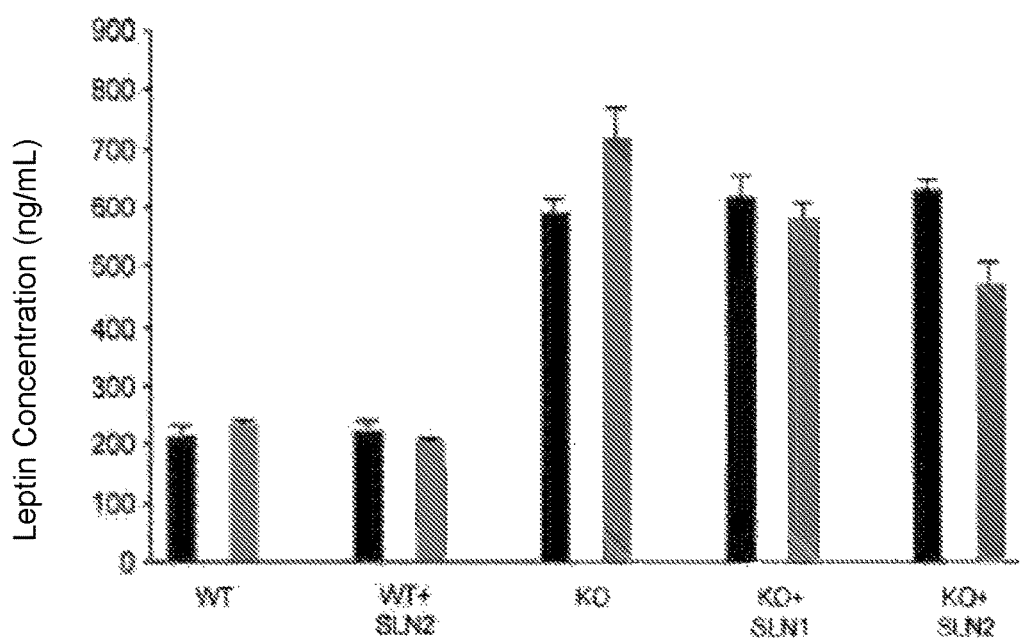

FIGURE 7. Metformin Glycinate Inhibits GPBP Phosphorylation
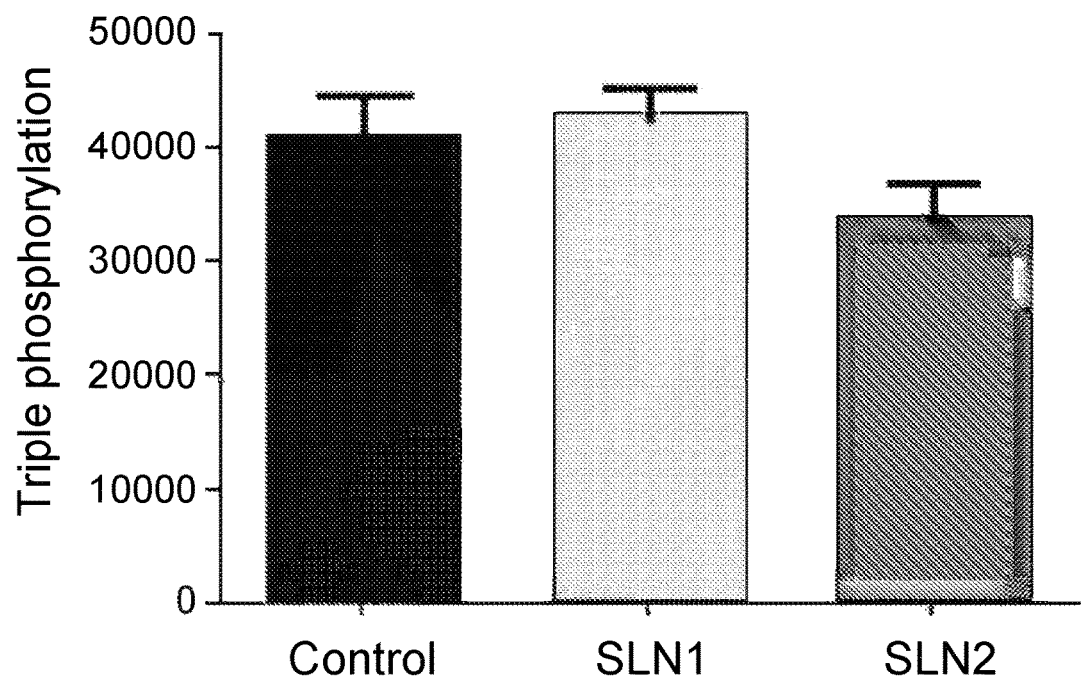

FIGURE 8. Metformin Glycinate Reduces Ceramide Levels
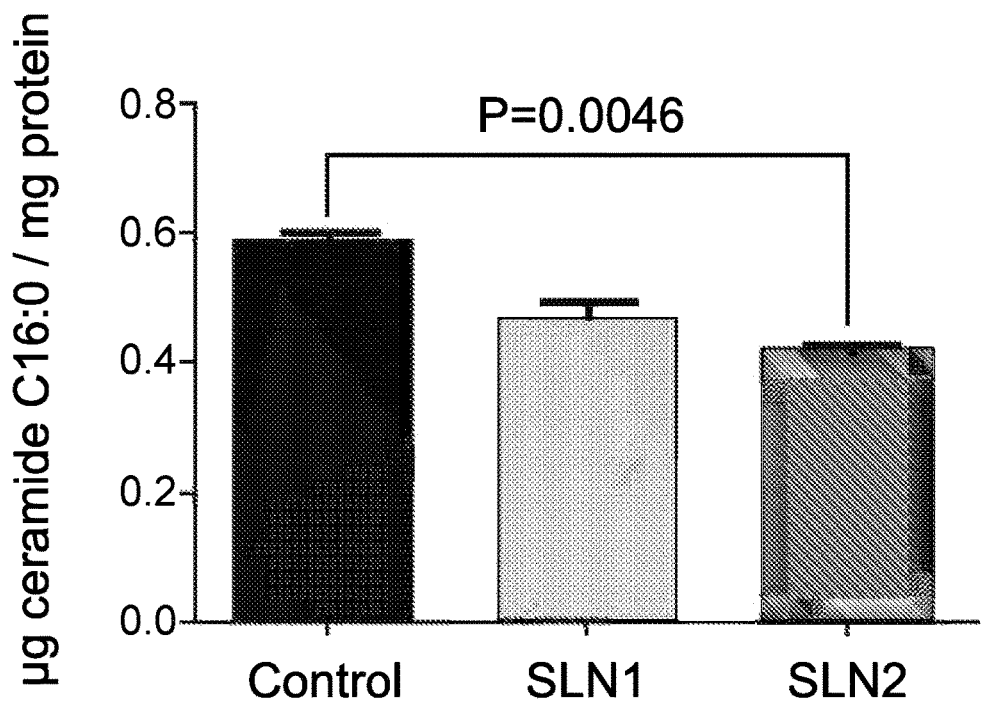

FIGURE 9. Treatment with Metformin Glycinate Resulted in Significantly More Accumulation of IRβ on the Cell Membrane than Treatment with Metformin
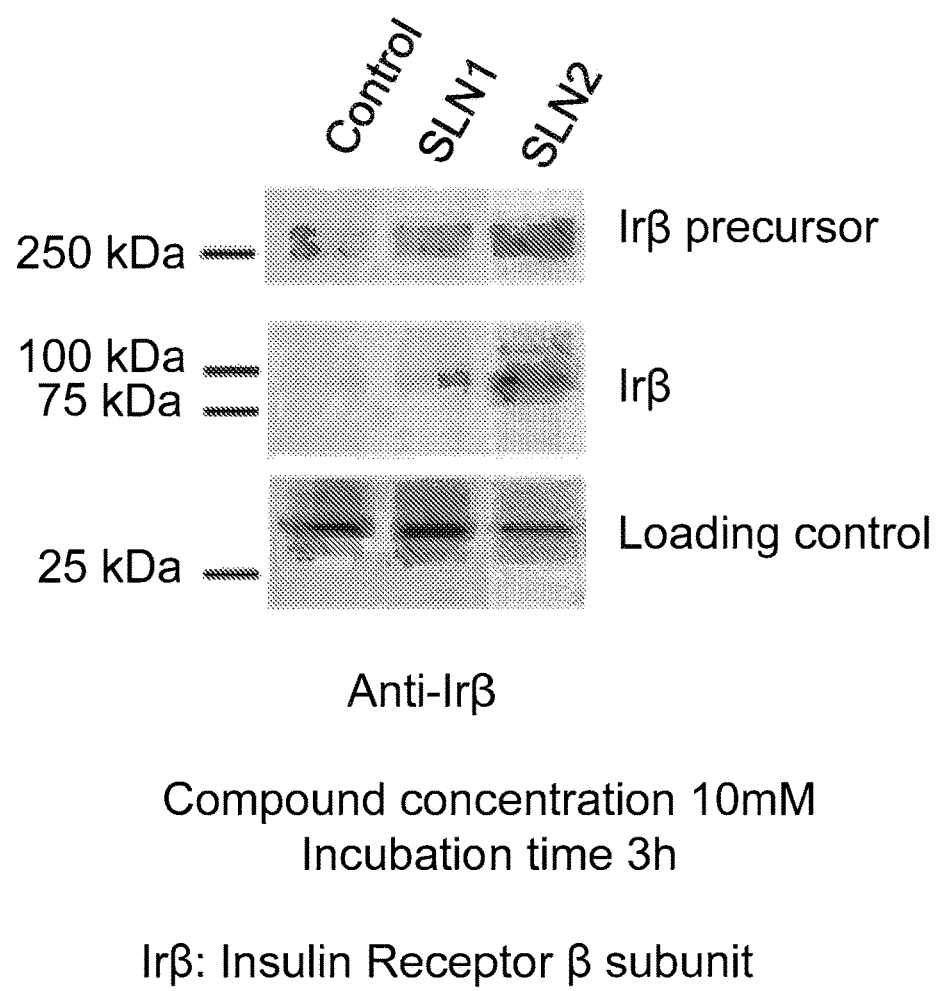

FIGURE 10. Treatment with Metformin Glycinate Reduces Pro-inflammatory Cytokines
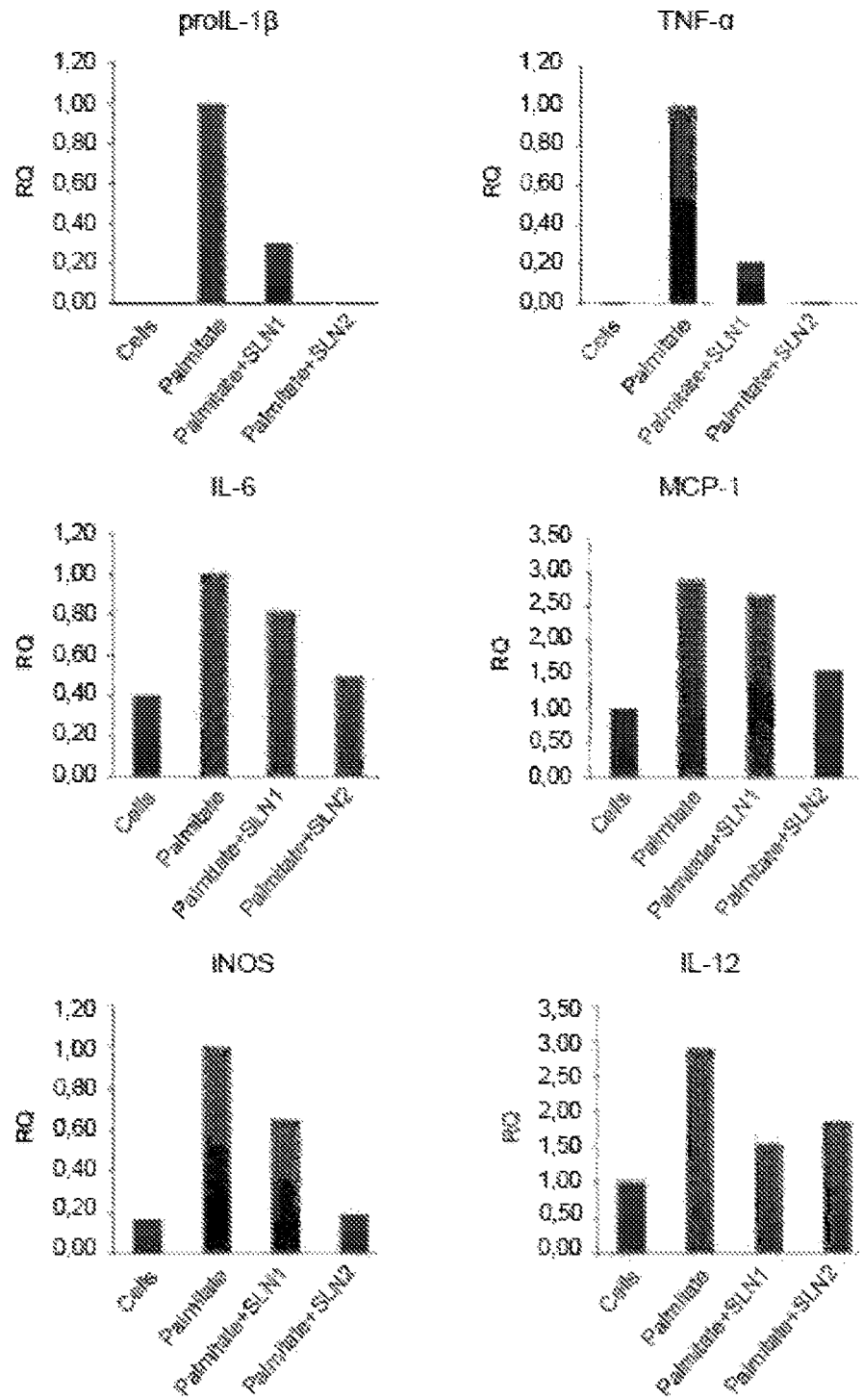

FIGURE 11. Metformin Glycinate Decreases Hyperglycemic Levels in C2C12 Myotubes Induced by M1 Macrophage Conditioned Media
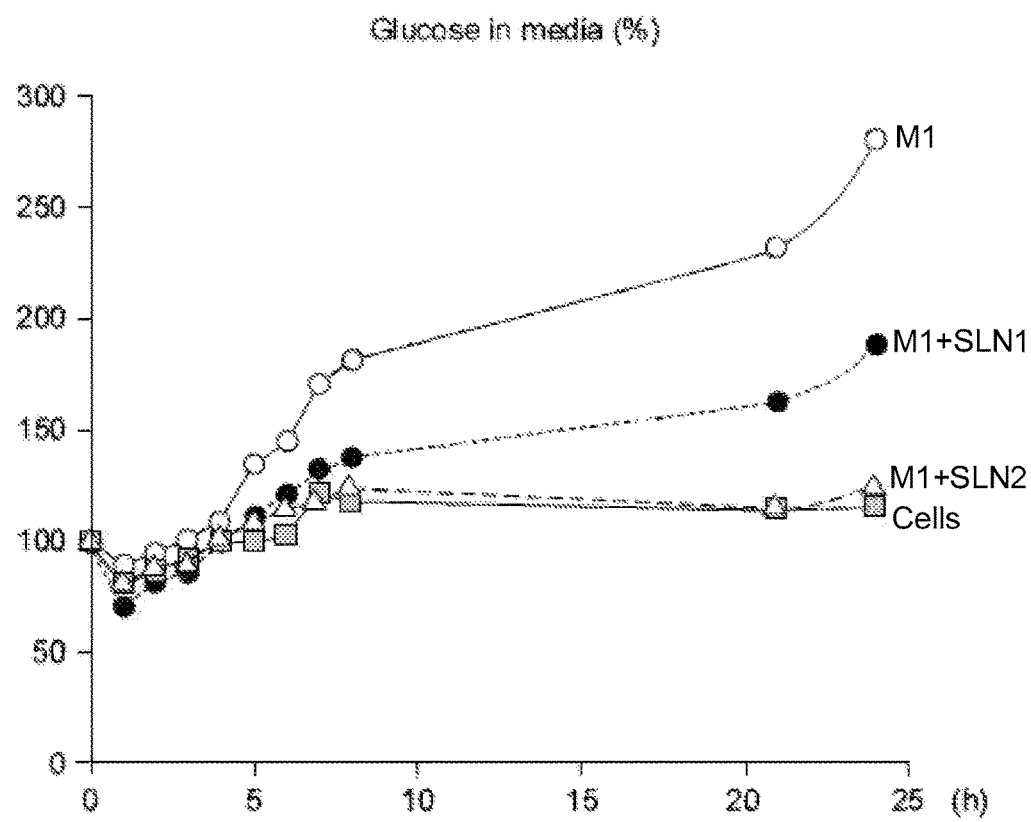

FIGURE 13. Metformin Association with Glycine in Aqueous Solutions
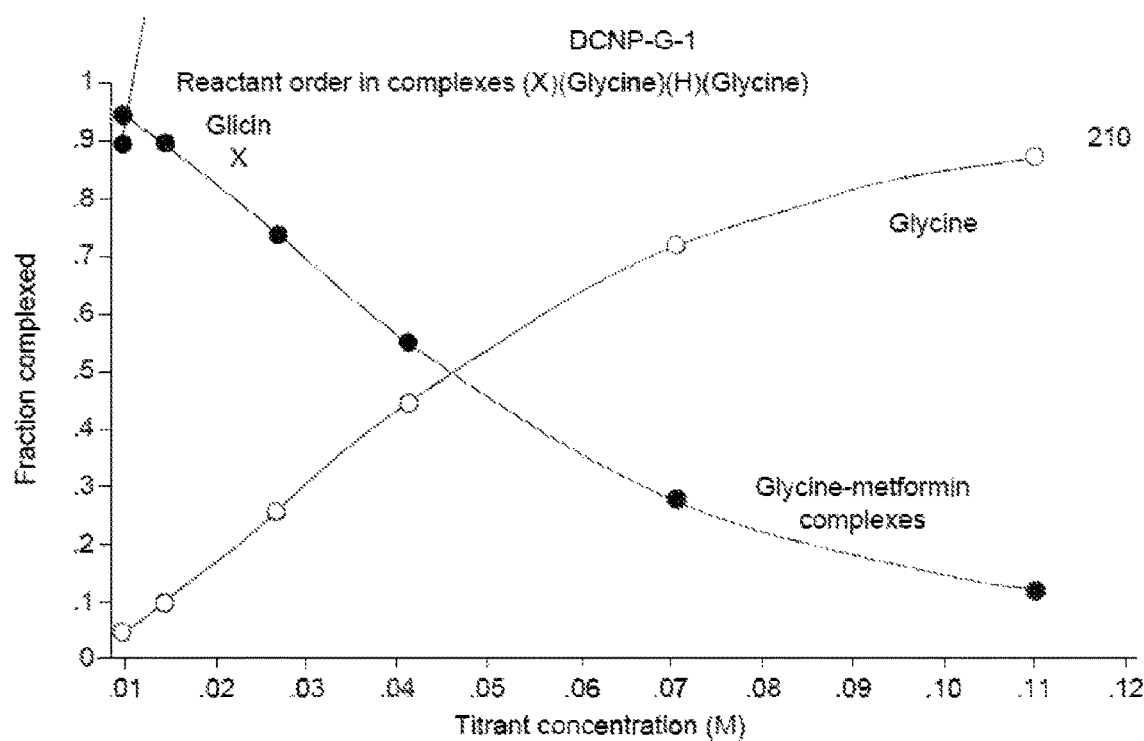

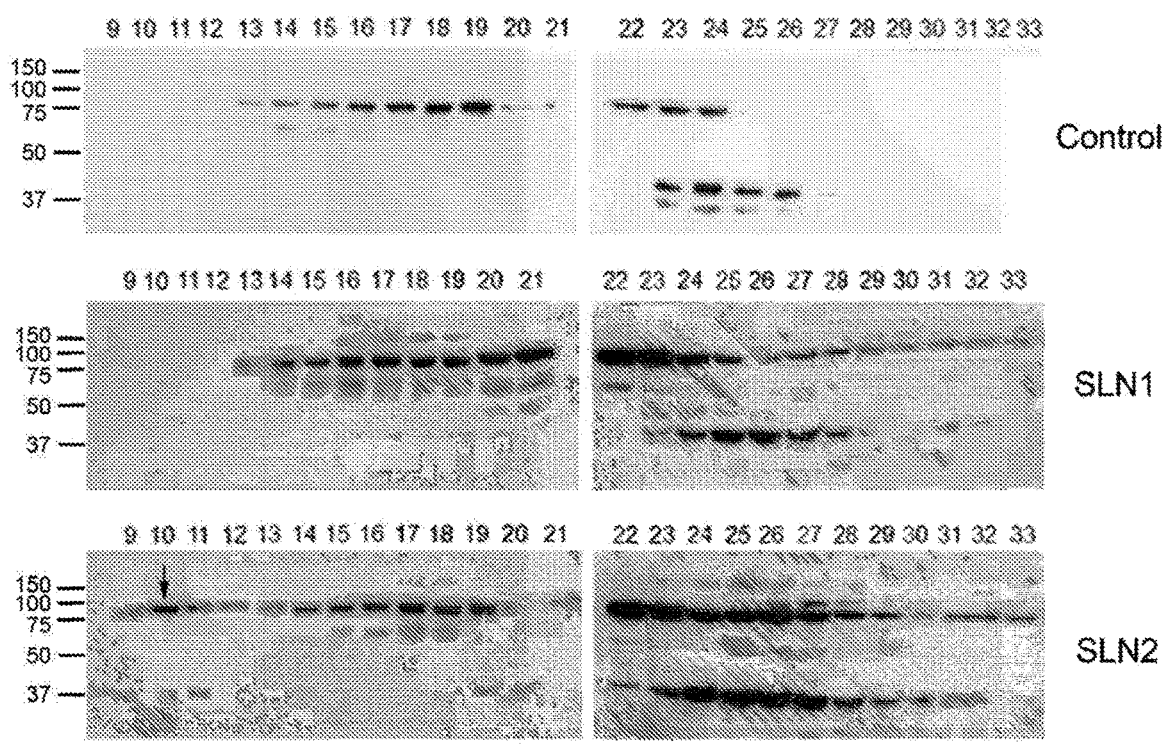
FIGURE 14. SLN2 alters GPBP aggregation state in the cytoplasm of HeLa cells FIGURE 15. SLN2 inhibits cross activation of GPBP/CERT
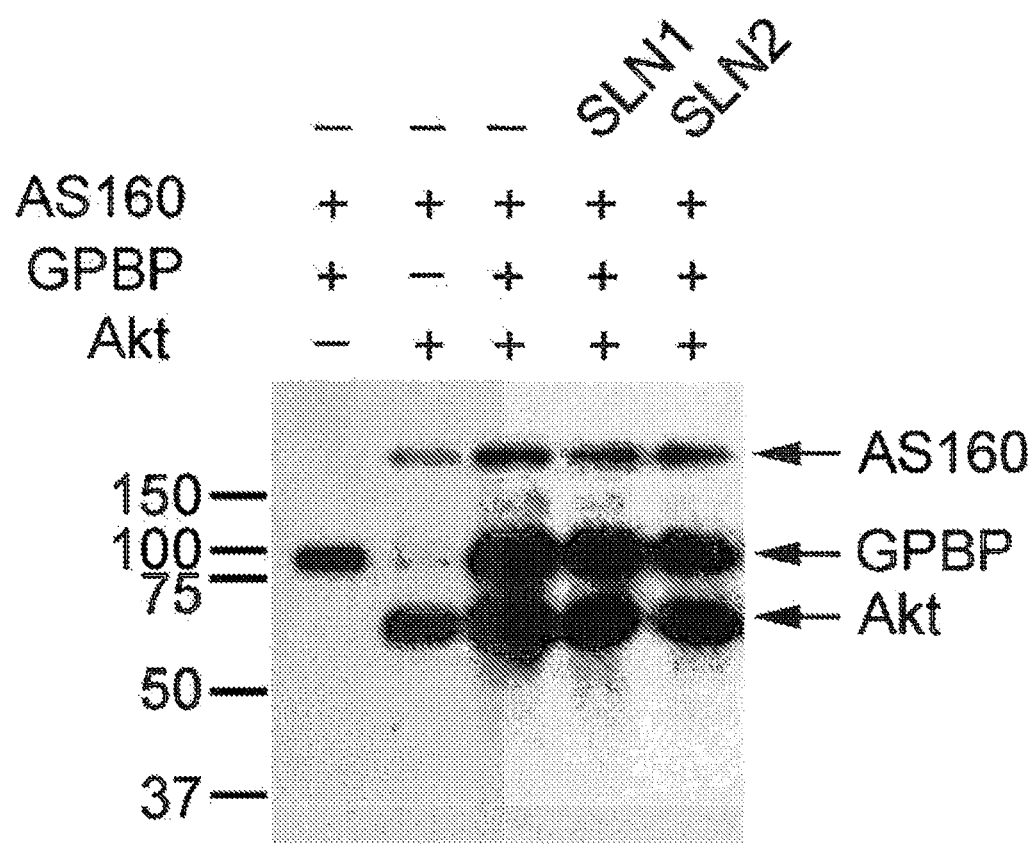

FIGURE 16. SLN2 increases AS160 phosphorylation in the presence of GPBP, AMPK, and AKT
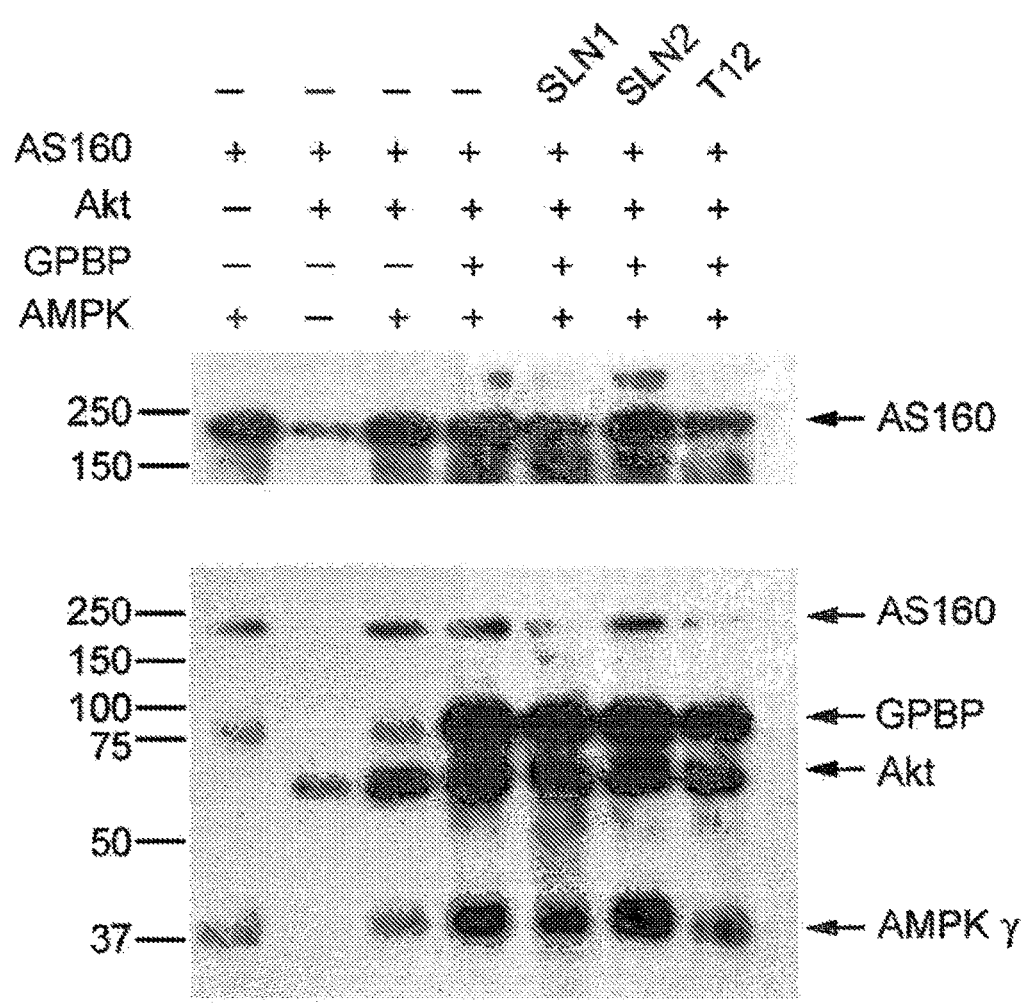

FIGURE 17. GPBP-1 Expression is Required for IL-1β and IL-10 Expression and Secretion to Extracellular Media
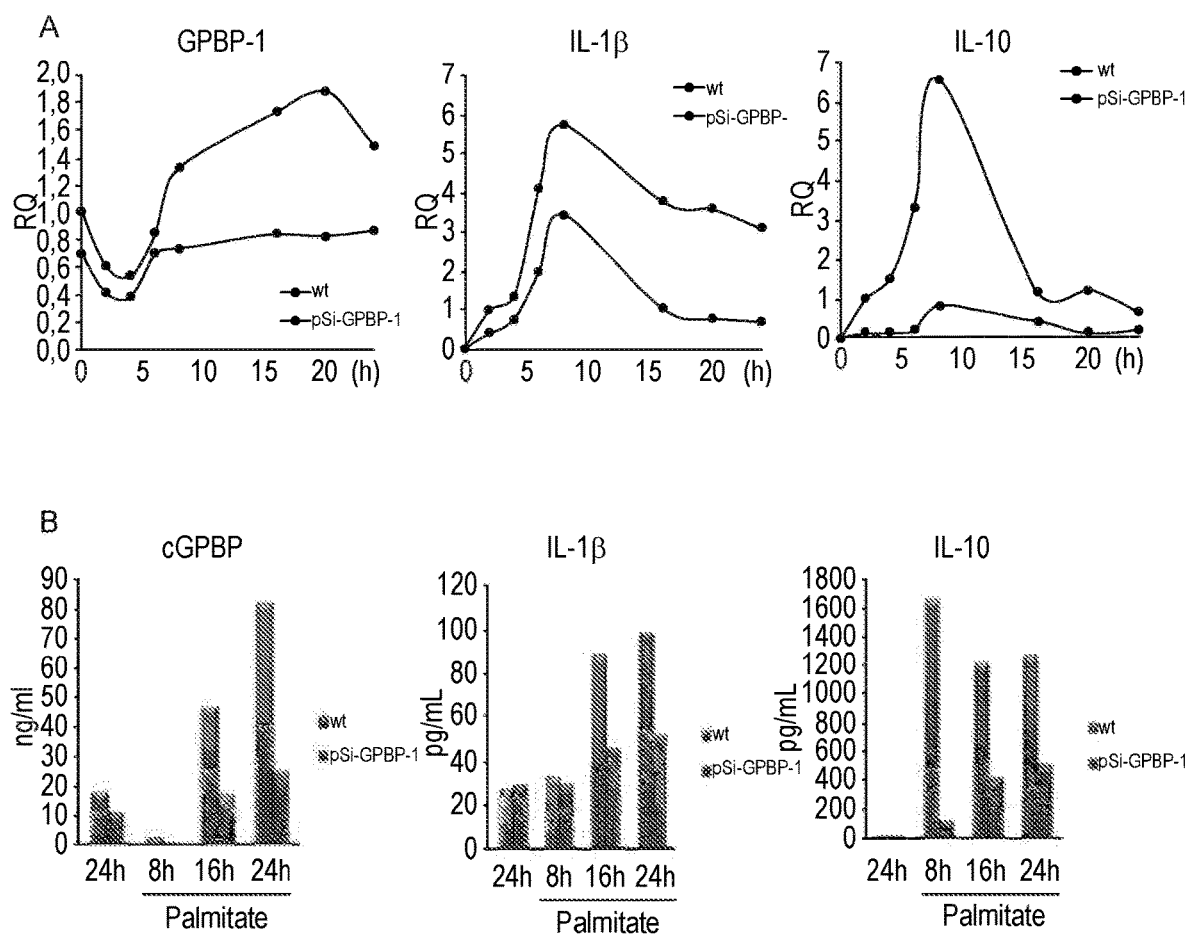

FIGURE 18. Metformin Glycinate Reduces Colocalization of VAPA and VAMPs
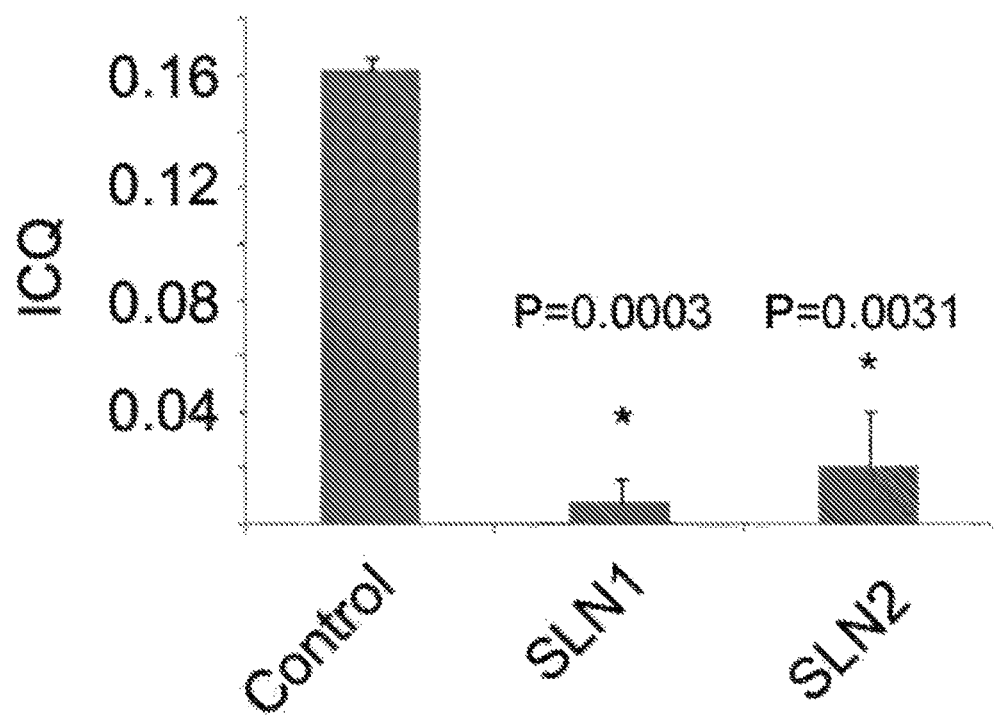

Green for GLUT4, Red for GPBP, and white for GPBP

FIGURE 20. Treatment with SLN2 Reduces Body Weight in IRS2 Knockout Mice
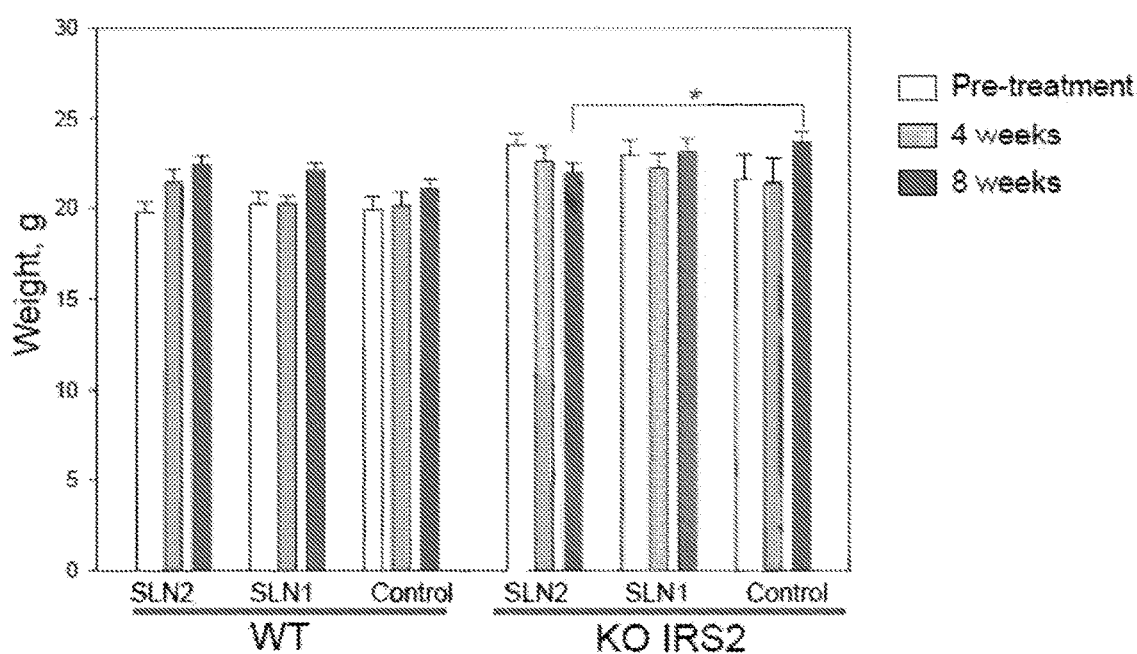

FIGURE 21. Serum Triglycerides are Reduced in IRS2 Knockout Mice Treated with SLN2
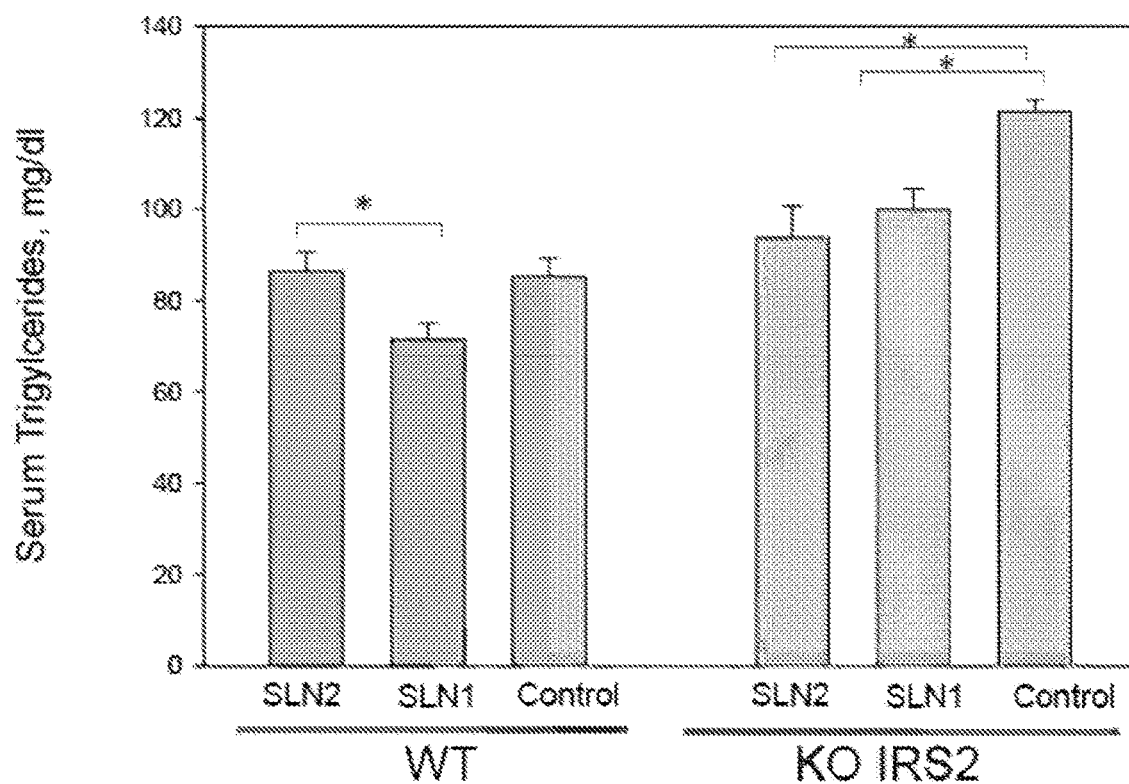

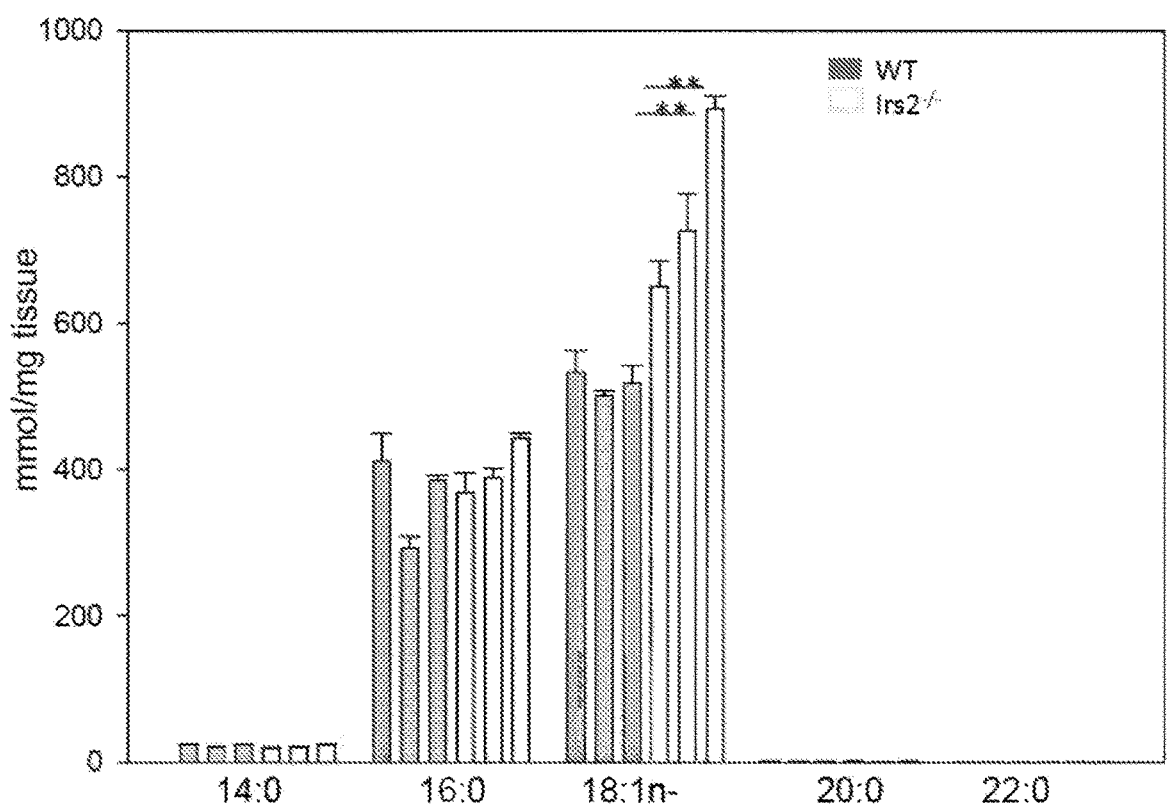
FIGURE 22. Adipose Triglycerides are Reduced in IRS2 Knockout Mice Treated with SLN2

METFORMIN GLYCINATE, PHARMACEUTICAL COMPOSITIONS COMPRISING THE SAME, AND METHODS OF USING THE SAME

FIELD OF THE INVENTION

The field of this invention generally relates to metformin glycinate, compositions comprising the compound, and methods of using the compound for the treatment of diseases.

BACKGROUND OF THE INVENTION

Diabetes mellitus, commonly referred to as diabetes, is a chronic disease associated with abnormally high levels of glucose in the blood. Diabetes is due to the pancreas not producing enough insulin and/or the cells of the body not responding to insulin properly. There are two main types of diabetes: type 1, which results from the pancreas' failure to produce enough insulin, and type 2, which results from cells' failure to respond to insulin properly. Type 2 diabetes is more common of the two. Treatments of diabetes include mono- and combination therapies.

Metformin is a medication for the treatment of type 2 diabetes. It belongs to the class of compounds known as biguanides. Marketed metformin medications contain metformin hydrochloride. Side effects of metformin hydrochloride include gastrointestinal intolerance (e.g., diarrhea, nausea/vomiting). Metformin hydrochloride is contraindicated in patients with renal disease or renal dysfunction or acute or chronic metabolic acidosis.

Metformin glycinate is a biguanide useful for treating diabetes. U.S. Pat. No. 8,703,183 discloses that the compound has the following exemplary characteristics: chemical name: N,N-dimethylimidodicarbonimidic diamide glycinate; molecular formula: $C_6H_{16}N_6O_2$ ($C_4H_{11}N_5 \cdot C_2H_5NO_2$); molecular weight: 204.25; and the structural formula:

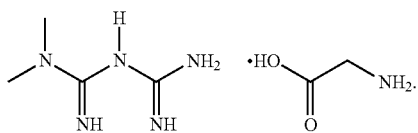

Obesity is a medical condition in which excess body fat has accumulated to the extent that it may have a negative effect on health. Obesity is a leading preventable cause of death worldwide, with increasing rates in adults and children. See "Obesity and overweight" WHO January 2015. See who.int/mediacentre/factsheets/fs311/en/. In 2013, the American Medical Association classified obesity as a disease.

Dyslipidemia is a disorder characterized by disruption in the amount of lipids in the blood, including elevated low density lipoprotein cholesterol (LDL), elevated apolipoprotein B, elevated triglycerides (TGs), elevated lipoprotein (a), elevated apolipoprotein A, reduced high density cholesterol (HDL) or reduced apolipoprotein A1. Abnormal cholesterol and TG levels have been implicated in the onset of diseases such as atherosclerosis, coronary artery disease, stroke and heart attacks. Cholesterol and TG levels can be mediated by lifestyle changes, but those changes alone some patients may not be sufficient. Many patients require medication to treat dyslipidemia.

Interleukin 10 (IL-10), also known as human cytokine synthesis inhibitory factor (CSIF), is an anti-inflammatory cytokine. Mosser D. M. and Zhang X., "Interleukin-10: new perspectives on an old cytokine" *Immunological Reviews* 226(1): 205-18 (2008). In humans, interleukin 10 is encoded by the IL10 gene. IL-10 signals through a receptor complex consisting of two IL-10 receptor 1 (IL-10R1) and two IL-10 receptor 2 (IL-10R2) proteins. Mosser D. M. and Zhang X., "Interleukin-10: new perspectives on an old cytokine" *Immunological Reviews* 226(1): 205-18 (2008). The functional receptor consists of four IL-10 receptor molecules. IL-10 binding induces STAT3 signaling via the phosphorylation of the cytoplasmic tails of IL-10 receptor 1 and IL-10 receptor 2 by JAK1 and Tyk2, respectively.

IL-10 inhibits the production of pro-inflammatory mediators as well as augments the production of anti-inflammatory factors including soluble TNF-α receptors and IL-1RA. Fioranelli M. and Grazia R. M., "Twenty-five years of studies and trials for the therapeutic application of IL-10 immunomodulating properties. From high doses administration to low dose medicine new paradigm," *Journal of Integrative Cardiology* 1(1): 2-6 (2014). IL-10 is a candidate for therapeutic intervention in a wide variety of disease states, including autoimmune disorders, acute and chronic inflammatory diseases, cancer, infectious disease, autoimmune and allergic disease, rejection of transplanted organs and graft-versus-host diseases after transplantation.

BRIEF SUMMARY OF THE INVENTION

The present disclosure provides a method of treating diabetes comprising orally administering to a subject in need thereof a therapeutically effective amount metformin glycinate, wherein the metformin glycinate is administered without food. In some embodiments, the therapeutically effective amount of metformin glycinate is from about 500 mg to about 3000 mg, from about 500 mg to about 2500 mg, from about 500 mg to about 2000 mg, from about 500 mg to about 1500 mg, from about 500 mg to about 1000 mg, from about 600 mg to about 2500 mg, from about 600 to about 2000 mg, from about 600 mg to about 1500 mg, from about 600 mg to about 1000 mg, from about 700 mg to about 2500 mg, from about 700 mg to about 2000 mg, from about 700 mg to about 1500 mg, from about 700 mg to about 1000 mg, from about 800 to about 2500 mg, from about 800 mg to about 2000 mg, from about 800 mg to about 1500 mg, from about 900 mg to about 2500 mg, from about 900 mg to about 2000 mg, from about 900 mg to about 1500 mg, from about 1000 mg to about 2500 mg, from about 1000 mg to about 2000 mg, from about 1000 mg to about 1500 mg, or any other amount or range described herein.

In some embodiments, the therapeutically effective amount of metformin glycinate is about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, or about 3000 mg. In other embodiments, the therapeutically effective amount of metformin glycinate is about 620 mg, about 930 mg, about 1240 mg, or about 2480 mg.

In some embodiments, the therapeutically effective amount metformin glycinate is comprised in a pharmaceutical composition. In some embodiments, the pharmaceutical composition is a solid composition such as a tablet or a capsule.

In some embodiments, the metformin glycinate is administered at least 1 hour, at least 2 hours, at least 3 hours, or at least 4 hours before or after any meals. In some embodiments, the method decreases the $T_{max}$ compared to an administration with food. In other embodiments, the metformin glycinate is administered once a day, twice a day, or three times a day.

Also provided is a method of treating diabetes comprising administering to a subject in need thereof a therapeutically effective amount metformin glycinate in combination with one of more additional antidiabetic agents. In some embodiments, the one or more additional antidiabetic agents are selected from the group consisting of a sulfonylurea, a thiazolidinedione, a dipeptidyl peptidase 4 (DPP4) inhibitor, a sodium/glucose cotransporter 2 (SGLT2) inhibitor, a glucagon-like peptide-1 (GLP1) receptor agonist, glucagon like peptide-1 (GLP-1), and insulin. In some embodiments, the metformin glycinate is administered before the administration of the one or more additional antidiabetic agents. In some embodiments, the metformin glycinate is administered at the same time as the administration of the one or more additional antidiabetic agents. In some embodiments, the metformin glycinate is administered after the administration of the one or more additional antidiabetic agents.

In some embodiments, the metformin glycinate and the one or more additional antidiabetic agents are administered orally. In some embodiments, the metformin glycinate and the one or more additional antidiabetic agents are in the same dosage form.

In some embodiments, the metformin glycinate is administered once daily or twice daily. In some embodiments, the treatment reduces the blood glycated hemoglobin (HbA1c) level in the subject to ≥about 7%.

The present disclosure further provides a method of treating obesity or reducing weight comprising administering to a subject in need thereof a therapeutically effective amount of metformin glycinate. In some embodiments, the metformin glycinate is administered orally. In some embodiments, the therapeutically effective amount of metformin glycinate is from about 500 mg to about 3000 mg, from about 500 mg to about 2500 mg, from about 500 mg to about 2000 mg, from about 500 mg to about 1500 mg, from about 500 mg to about 1000 mg, or any other amount or range described herein. In some embodiments, the metformin glycinate is administered once daily or twice daily.

The present disclosure further provides a method of treating dyslipidemia comprising administering to a subject in need thereof a therapeutically effective amount metformin glycinate. In some embodiments, the dyslipidemia is characterized by an elevated blood triglyceride level, an elevated blood low-density lipoproteins (LDL), a low level of blood high-density lipoproteins (HDL), or a combination thereof. In some embodiments, the metformin glycinate is administered orally. In some embodiments, the therapeutically effective amount of metformin glycinate is from about 500 mg to about 3000 mg, from about 500 mg to about 2500 mg, from about 500 mg to about 2000 mg, from about 500 mg to about 1500 mg, from about 500 mg to about 1000 mg, or any other amount or range described herein. In some embodiments, the metformin glycinate is administered once daily or twice daily. In some embodiments, the treatment lowers the blood triglyceride, lowers the blood LDL, raises the blood HDL level, or a combination thereof.

The present disclosure further provides a method of treating a heart disease comprising administering to a subject in need thereof a therapeutically effective amount metformin glycinate, wherein the heart disease is selected from the group consisting of atherogenesis, atherosclerosis, coronary artery disease (CAD), angina, heart attack, stroke, and a combination thereof. In some embodiments, the metformin glycinate is administered orally. In some embodiments, the therapeutically effective amount of metformin glycinate is from about 500 mg to about 3000 mg, from about 500 mg to about 2500 mg, from about 500 mg to about 2000 mg, from about 500 mg to about 1500 mg, from about 500 mg to about 1000 mg, or any other amount or range described herein. In some embodiments, the metformin glycinate is administered once daily or twice daily. In some embodiments, the metformin glycinate is administered in combination with one or more HMG-CoA reductase inhibitors.

The present disclosure further provides a method of treating a disease associated with IL-10 up-regulation comprising administering to a subject in need thereof a therapeutically effective amount metformin glycinate. In some embodiments, the disease is melanoma, carcinoma, lymphoma, food allergy, asthma, eosinophilic esophagitis or atopic dermatitis. In some embodiments, the metformin glycinate is administered orally. In some embodiments, the therapeutically effective amount of metformin glycinate is from about 500 mg to about 3000 mg, from about 500 mg to about 2500 mg, from about 500 mg to about 2000 mg, from about 500 mg to about 1500 mg, from about 500 mg to about 1000 mg, or any other amount or range described herein. In some embodiments, the metformin glycinate is administered once daily or twice daily.

In some embodiments, the subject being treated by the methods is a human.

The present disclosure also provides a pharmaceutical composition comprising metformin glycinate and one or more antidiabetic agents. In one embodiment, the composition comprises metformin glycinate and a sulfonylurea. In one embodiment, the composition comprises metformin glycinate and a thiazolidinedione (e.g., rosiglitazone). In one embodiment, the composition comprises metformin glycinate and a DPP4 inhibitor (e.g., sitagliptin, saxagliptin, linagliptin, or alogliptin) at an amount from about 2.5 mg to about 100 mg. In one embodiment, the composition comprises metformin glycinate and a SGLT2 inhibitor. In one embodiment, the composition comprises metformin glycinate and a GLP1 receptor agonist. In one embodiment, the composition comprises metformin glycinate and GLP-1. In one embodiment, the composition comprises metformin glycinate and insulin.

In some embodiments, the present disclosure provides a composition comprising metformin glycinate and an antihistamine selected from the group consisting of loratadine, diphendydramine, and cetirizine.

In some embodiments, the present disclosure provides a composition comprising metformin glycinate and a steroid selected from the group consisting of betamethasone, cortisone, dexamethasone, hydrocortisone, methylprednisolone, prednisolone, prednisone, and triamcinolone. In some embodiments, the present disclosure provides a composition comprising metformin glycinate and a bronchodilator selected from the group consisting of salbutamol and salmeterol.

In one aspect, the disclosure herein provides a method of treating a disease or disorder associated with elevated or increased ceramide levels comprising administering to a subject in need thereof a therapeutically effective amount of metformin glycinate. In some embodiments, the disease or disorder is insulin resistance, Alzheimer's disease, systemic lupus erythematosus, renal failure, allergic encephalomyelitis, central pontine myelinolysis (CPM), transverse myelitis, tabes dorsalis, optic neuritis, multiple sclerosis, systemic lupus erythematosus, or a combination thereof. In some embodiments, the disease or disorder is insulin resistance, Alzheimer's disease, systemic lupus erythematosus, multiple sclerosis, or a combination thereof. In one embodiment, the disease or disorder is insulin resistance. In another embodiment, the disease or disorder is Alzheimer's disease. In some embodiments, the therapeutically effective amount of metformin glycinate is an amount that lowers the ceramide level in the subject compared to the ceramide level before the administration. In some embodiments, the metformin glycinate is administered via commonly known routes (e.g., oral administration). In some embodiments, the subject is a human.

BRIEF DESCRIPTION OF THE DRAWINGS/FIGURES

FIG. 1 shows treatment with metformin glycinate reduces blood A1C levels in type 2 diabetic patients.

FIG. 2 shows that the administration of metformin glycinate after food intake increased $T_{max}$ compared to administration without food.

FIG. 3 shows metformin glycinate inhibits IL-10 expression in macrophages activated by LPS and INF-γ.

FIG. 4 shows metformin glycinate inhibits cancer cell growth.

FIG. 5 shows metformin glycinate reduces fasting serum leptin levels in IRS2 knockout mice. The black bars show fasting serum leptin levels at the beginning of the treatment and the grey bars show fasting serum leptin levels at the end of the treatment.

FIG. 7 shows that treatment with metformin glycinate but not with metformin hydrochloride reduced the amount of triple phosphorylated peptide.

FIG. 8 shows treatment with metformin glycinate, but not metformin hydrochloride, significantly reduced ceramide C16:0 levels in L1 adipocytes expressing recombinant GPBP.

FIG. 9 shows that treatment with metformin glycinate resulted in significantly more accumulation of IRβ on the cell membrane than treatment with metformin hydrochloride.

FIG. 10 shows that treatment with metformin glycinate reduces pro-inflammatory cytokines such as proIL-1β, TNFα, iNOS, IL-6, MCP-1, and IL-12.

FIG. 11 shows that metformin glycinate decreases hyperglycemic levels of in C2C12 myotubes induced by M1 macrophage conditioned media.

Figure 12A:
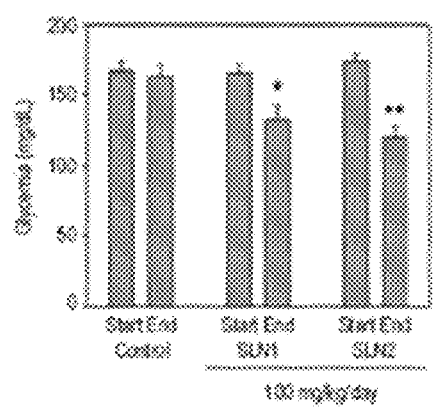
Figure 12B:
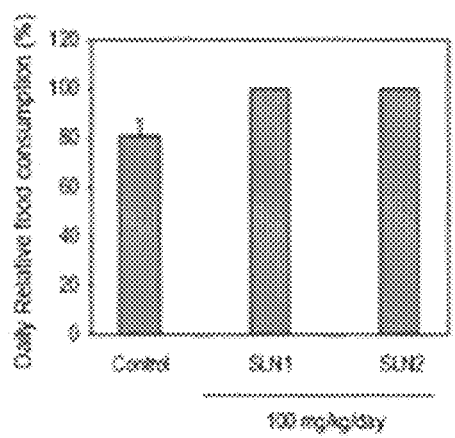
Figure 12C:
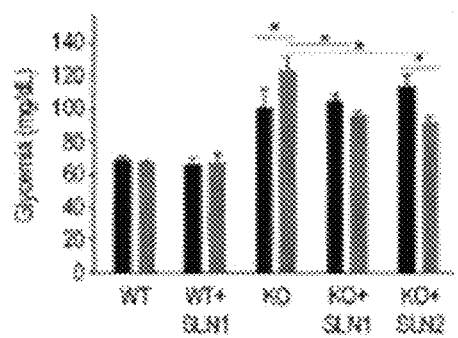
Figure 12D:
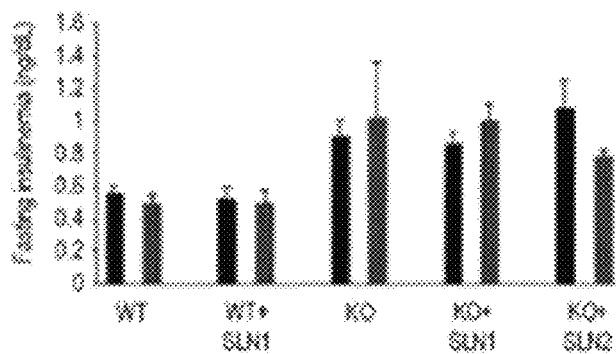

FIGS. 12A-D show the glycemic levels and appetite in C57BL/6 mice as well as fasting glycemia and insulinemia in IRS2 knockout (IRS2-/-) mice treated with metformin hydrochloride (SLN1) or metformin glycinate (SLN2). FIG. 12A shows the differences of glycemic levels at the beginning and the end of the treatment. FIG. 12B shows the relative daily dietary intake of the mice used in FIG. 12A. FIG. 12C shows glycemia of female IRS2-/- (KO) mice and their corresponding controls (WT) in different groups pre-treatment (black bars) and post-treatment (gray bars) along with their standard deviations. An asterisk (*) denotes statistically significant differences (P<0.05) among the indicated groups according to the Student's t-test. FIG. 12D shows the fasting serum insulin levels taken in KO mice and their corresponding controls (WT) pre-treatment (black bars) and post-treatment (gray bars). Mean values and standard deviations are presented for each group (n=3).

FIG. 13 shows that metformin associates with glycine in aqueous solutions.

FIG. 14 shows that SLN2 alters GPBP aggregation state in the cytoplasm of HeLa cells.

FIG. 15 shows that SLN2 inhibits cross activation of GPBP/CERT.

FIG. 16 shows that SLN2 increases AS160 phosphorylation in the presence of GPBP, AMPK, and AKT.

FIG. 17 shows that GPBP-1 expression is critical for IL-1β and IL-10 expression and secretion to extracellular media.

FIG. 18 shows that metformin glycinate reduces colocalization of VAPA and VAMPs.

Figure 19A:
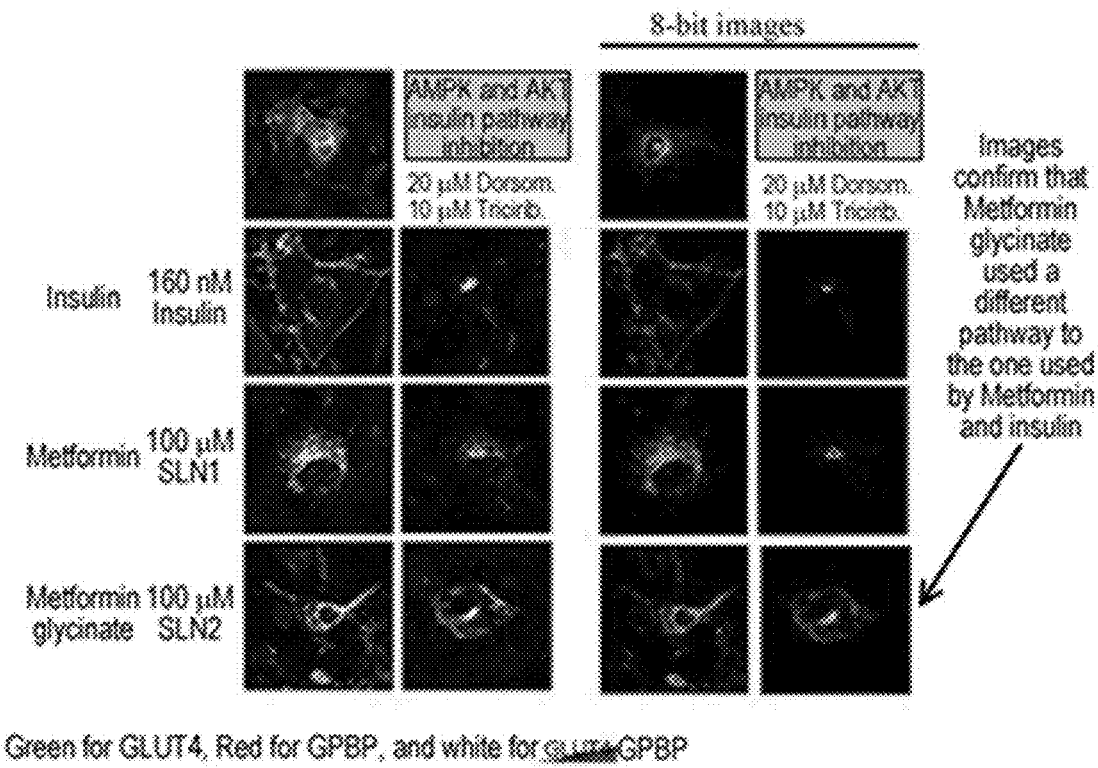
Figure 19B:
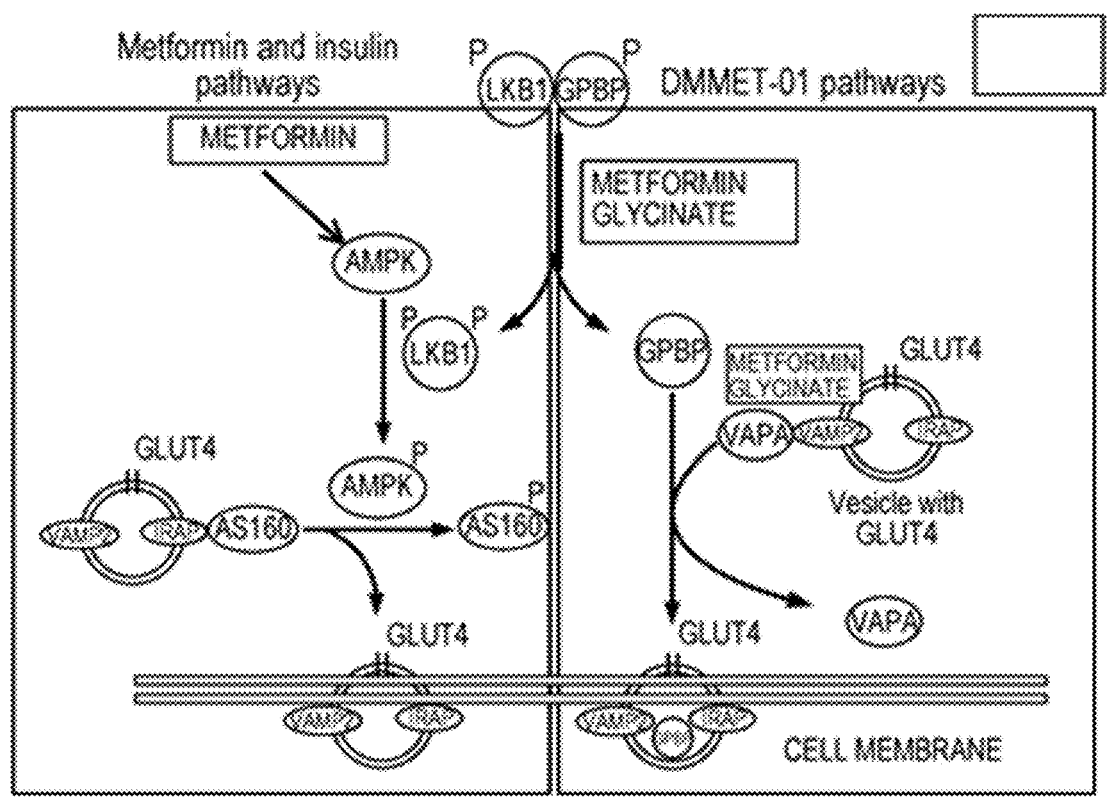

FIG. 19A shows that metformin glycinate translocates GLUT4 more efficiently than metformin hydrochloride. FIG. 19B shows a model depicting the pathways of metformin glycinate and metformin hydrochloride in translocating GLUT4.

FIG. 20 shows that metformin glycinate reduces body weight in IRS2 knockout mice.

FIG. 21 shows that metformin glycinate reduces serum triglyceride levels in IRS2 knockout mice.

FIG. 22 shows that metformin glycinate reduces adipose triglyceride levels in IRS2 knockout mice.

DETAILED DESCRIPTION OF THE INVENTION

The present disclosure provides pharmaceutical compositions comprising metformin glycinate and methods of using metformin glycinate for the treatment of various diseases. In one aspect, the present disclosure provides a method for treating diabetes in a subject in need thereof comprising administering a therapeutically effective amount of metformin glycinate, preferably without food. In one aspect, the present disclosure provides a method for treating diabetes comprising administering to a subject in need thereof a therapeutically effective amount metformin glycinate in combination with one or more additional antidiabetic agents.

In one aspect, the present disclosure provides a method for treating obesity comprising administering to a subject in need thereof a therapeutically effective amount of metformin glycinate.

In one aspect, the present disclosure provides a method of treating dyslipidemia comprising administering to a subject in need thereof a therapeutically effective amount metformin glycinate. In another aspect, the present disclosure provides a method of treating a heart disease such as atherogenesis, atherosclerosis, coronary artery disease (CAD), angina, heart attack, stroke, or a combination thereof, comprising administering to a subject in need thereof a therapeutically effective amount metformin glycinate.

In one aspect, the present disclosure provides a method of treating a disease associated with IL-10 up-regulation, such as melanoma, carcinoma, lymphoma, food allergy, asthma, eosinophilic esophagitis, atopic dermatitis, or a combination thereof, comprising administering to a subject in need thereof a therapeutically effective amount metformin glycinate.

To facilitate an understanding of the present inventions, a number of terms and phrases are defined below.

Definitions

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

In this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

The term "about" as used herein refers to that the number comprehended is not limited to the exact number set forth herein, and is intended to refer to ranges substantially within the quoted range while not departing from the scope of the invention. As used herein, "about" will be understood by persons of ordinary skill in the art to account for measurement errors, for example, in the range of up to plus or minus 10% of the particular term.

As used herein the terms "treat," "treatment," or "treatment of" refer to (i) reducing the potential for a disease or disorder (e.g., diabetes or other disease disclosed herein), (ii) reducing the occurrence of a disease or disorder, (iii) reducing the severity of a disease or disorder, preferably, to an extent that the subject no longer suffers discomfort and/or altered function due to it, or (iv) a combination thereof.

For example, treating can refer to the ability of a therapy when administered to a subject, to prevent a disease or disorder from occurring and/or to cure or to alleviate the disease or disorder's symptoms, signs, or causes. Treating also refers to mitigating or decreasing at least one clinical symptom and/or inhibition or delay in the progression of the condition and/or prevention or delay of the onset of a disease or illness. Thus, the terms "treat," "treating" or "treatment of" (or grammatically equivalent terms) refer to both prophylactic and therapeutic treatment regimes.

The terms "subject" or "patient" as used herein refer to any subject, particularly a mammalian subject, for whom diagnosis, prognosis, or therapy of a disease or disorder (e.g., diabetes or other disease disclosed herein) is desired. As used herein, the terms "subject" or "patient" include any human or nonhuman animal. The term "nonhuman animal" includes all vertebrates, e.g., mammals and non-mammals, such as mice, nonhuman primates, sheep, dogs, cats, horses, cows, bears, chickens, amphibians, reptiles, etc. In preferred embodiments, a subject is a human.

The term "therapeutically effective amount" as used herein refers to an amount of a drug effective to "treat" a disease or disorder in a subject. A "therapeutically effective amount" includes an amount of a drug or a therapeutic agent that provides some improvement or benefit to a subject having a disease or disorder (e.g., diabetes or other disease disclosed herein). Thus, a "therapeutically effective" amount is an amount that provides some alleviation, mitigation, and/or decrease in at least one clinical symptom of a disease or disorder (e.g., diabetes or other disease disclosed herein).

The term "administration" or "administering" of a drug or a medication, as used herein, includes delivering, applying, or giving the therapy or drug to a subject including self-administering by the subject.

The term "without food" as used herein refers to the administration of a drug or a medication on a substantially empty stomach. Accordingly, in some embodiments, administration without food includes administration more than about 15 minutes, 30 minutes, 60 minutes, 90 minutes, 120 minutes, 150 minutes, 3 hours, 4 hours, 5 hours, 6 hours, 7 hours, or 8 hours after the most recent consumption of food. In other embodiments, administration without food includes administration at least about 15 minutes, 30 minutes, 60 minutes, 90 minutes, 120 minutes, 150 minutes, 3 hours, 4 hours, 5 hours, 6 hours, 7 hours, or 8 hours before the next consumption of food. In some embodiments, food includes nutritional liquids or liquid nutritional supplements (e.g., Glucerna Shake or Nepro®). In some embodiments, the term "without food" is administration of a drug or a medication at least about one hour, at least about two hours, at least about three hours, or at least about four hours, before a meal or after a meal.

The term "obesity" as used herein refers to a condition of abnormal or excessive accumulation of adipose tissue, to the extent that health of a subject may be impaired. In humans, the body mass index (BMI; $kg/m^2$) provides a useful measure of obesity. BMI refers to the weight in kilograms divided by the square of the height in meters, and it is a commonly used index to classify overweight and obesity in adults. The World Health Organization (WHO) has classified overweight and obesity for adults using BMI. According to the WHO BMI classification for adults, underweight: BMI<18.5 $kg/m^2$, normal weight: BMI between 18.5 $kg/m^2$ and higher to 24.99 $kg/m^2$, overweight: BMI 25 $kg/m^2$ and higher to 29.99 kg/m², obese grade I: BMI 30 kg/m² and higher to 34.99 kg/m², obese grade II: BMI 35 kg/m² and higher to 39.99 kg/m², obese grade III and more: BMI≥40 kg/m². See who.int/features/factfiles/obesity/facts/en/. Accordingly, in some embodiments, the term "obesity" includes adult humans with a BMI of ≥25 kg/m², in other embodiments, the term include adult humans with a BMI of ≥35 kg/m², in other embodiments, the term includes adult humans with a BMI of ≥40 kg/m².

The term "overweight" as used herein refers to a condition of having more body fat than what is considered healthy. In humans, the body mass index (BMI; kg/m²) provides a useful measure of being overweight. According to the WHO BMI classification for adults, overweight refers to an adult person having a BMI of between 25 to 29.99 kg/m². Accordingly, in some embodiments, the term "overweight" includes adult humans with a BMI of between 25 and higher to 29.99 kg/m².

The term an "antidiabetic agent" as used herein refers to a drug or a medication that treats diabetes mellitus by lowering glucose levels in the blood of a subject, reduces or alleviates the severity of diabetes, alleviates at least one clinical symptom of diabetes, inhibits or delays in the progression of diabetes, prevents or delays the onset of diabetes, or a combination thereof. In some aspects, an antidiabetic agent includes a sulfonylurea (e.g., glimepiride, glipizide, glyburide), a thiazolidinedione (e.g., pioglitazone, rosiglitazone, lobeglitazone), a dipeptidyl peptidase 4 (DPP4) inhibitor (e.g., sitagliptin, vildagliptin, saxagliptin, linagliptin, gemigliptin, anagliptin, teneligliptin, alogliptin, trelagliptin, dutogliptin, omarigliptin), a sodium/glucose cotransporter 2 (SGLT2) inhibitor (e.g., canagliflozin, dapagliflozin), a glucagon-like peptide-1 (GLP1) receptor agonist (e.g., exenatide, liraglutide, lixisenatide, albiglutide, dulaglutide, taspoglutide, semaglutide), glucagon like peptide-1 (GLP-1), or insulin (e.g., animal insulin preparations extracted from the pancreas of cattle or pigs; human insulin preparations synthesized by genetic engineering using *Escherichia coli* or yeast; insulin zinc; protamine insulin zinc; insulin fragments or derivatives (e.g., INS-1), oral insulin preparations).

The term "dyslipidemia" as used herein refers to a disorder with abnormal amount of lipids in the blood. The disorder is characterized by an elevated blood triglyceride (TG) level, an elevated blood low-density lipoproteins (LDL), an elevated total blood cholesterol, a low level of blood high-density lipoproteins (HDL), elevated blood apolipoprotein B (apo B) level, elevated blood apolipoprotein A1 (apo A1), or a combination thereof. Blood TG, LDL, DHL, apo B, and apo A1 levels can be determined by methods well known in the art. Total blood cholesterol level can be calculated using the following equation: HDL+LDL+20 percent of TG level.

Dyslipidemia increases the risk of and contributes to the development of cardiovascular diseases such as atherosclerosis, coronary artery disease (CAD), stroke and heart attacks. Risk factors for dyslipidemia include primary (e.g., genetic) and/or secondary (e.g., lifestyle). Common secondary causes for dyslipidemia include sedentary lifestyle, excessive dietary intake of saturated fat, cholesterol, and trans fats, alcohol overuse, smoking, other diseases such as HIV infection, nephrotic syndrome, diabetes mellitus, hypothyroidism, primary biliary cirrhosis and other cholestatic liver diseases, chronic kidney disease, and drugs (e.g., thiazides, β3-blockers, retinoids, highly active antiretroviral agents, cyclosporine, tacrolimus, estrogen and progestins, and glucocorticoids).

Although there is no natural cutoff between normal and abnormal lipid levels, there are general guidelines for blood HDL, LDL, TG, apoA1, apoB, and total cholesterol levels. Generally the target LDL level is less than 160 mg/dL (4.15 mmol/L) for patients with one risk factor, and 130 mg/dL (3.35 mmol/L) or less for patients with two or more risk factors. The target HDL level is 60 mg/dL or greater, the target TG level is 150 mg/dL or less, and the target total cholesterol level is 200 mg/dL (5.15 mmol/L) or less. The target apo B level is <90 mg/dL (patients with risk of CAD) or <80 mg/dL (patients with established CAD). Patients who have one or more of blood LDL, TG, total cholesterol, and apoB levels above the target normal, or blood HDL level below the target level may be treated with the method disclosed herein. Screening and determining normal or target blood lipid levels (e.g., HDL, LDL, TG, total cholesterol, apoB, and apoA1) are known in the art. See e.g., American Association of Clinical Endocrinologists' Guidelines for Management of Dyslipidemia and Prevention of Atherosclerosis (AACE Guidelines), accessible at aace.com/files/lipid-guidelines.pdf. Blood HDL, LDL, TG, apoA1, apoB and total cholesterol levels can be determined by measuring fast lipid profile of a patient. Such measurements are well known in the art, e.g., can be performed by a clinical laboratory.

As a linear relation typically exists between lipid levels and cardiovascular risk, people with "normal" cholesterol levels can benefit from achieving still lower levels. Consequently, in certain aspects, the term also includes lipid levels for which treatment would be considered beneficial.

The term "a disease associated with interleukin-10 (IL-10) up-regulation" as used herein refers to any pathology associated with (alone or in association with other mediators) or exacerbated by elevated levels of IL-10, or any pathology prolonged by elevated levels of IL-10 in a subject having the disorder. As used herein, elevated levels of IL-10 expression include elevated levels of IL-10 mRNA and/or protein.

IL-10 is a homodimeric cytokine that modulates the biological activities of immune cells, keratinocytes and endothelial cells. Generally, IL-10 binds to a tetrameric transmembrane cytokine receptor composed of two molecules of IL-10R1 and two accessory molecules of IL-10R2. IL-10-receptor interaction starts an intracellular signaling pathway that involves JAK1, Tyk2 and STAT3. STAT3 dimerization and nuclear translocation induce the expression of target genes. In addition, IL-10 reduces NK cytotoxicity and Th-1 response, resulting in immune depression.

IL-10 up-regulation is associated with increased cancer development, viral infection chronicization, and Th2 dependent autoimmune, inflammatory and allergic disorders. For example, IL-10 is up-regulated or over-expressed in many malignant diseases such as melanoma, carcinoma, lymphoma, and tumor cells derived from NK, T and B cell lymphomas. High levels of IL-10 are associated with disease progression, metastasize and immune suppression of these cancers. There is also a correlation between high levels of IL-10 and VEGF over-expression in some types of esophageal cancer. Increased IL-10 levels are linked to poor prognosis, unresponsiveness to chemotherapy and tumor recurrence after surgery.

IL-10 up-regulation can lead to an inappropriate clearance of pathogens, which can aid immune escape of viruses such as HIV, HBV, HCV, EBV and HPV. Th2-driven allergic response (e.g., food allergy, asthma, eosinophilic esophagitis and atopic dermatitis) is associated with IL-10 overexpression.

Thus, in some aspects, "a disease associated with interleukin-10 (IL-10) up-regulation" includes diseases such as cancers (e.g., melanoma, carcinoma, lymphoma), and their progression (e.g., metastasization), viral infections (e.g., HIV, HBV, HCV, EBV and HPV) and chronization, and allergic diseases (e.g., food allergy, asthma, eosinophilic esophagitis and atopic dermatitis). In some aspects, the term includes metastasized cancers (e.g., metastasized melanoma, carcinoma, or lymphoma). In other aspects, the term includes allergic diseases such as food allergy, asthma, eosinophilic esophagitis and atopic dermatitis or a combination thereof.

As used herein, the term "ceramides" refers to a family of lipid molecules. A ceramide is composed of sphingosine and a fatty acid that varies in length from 14 to 26 carbon atoms. Common ceramides include C16:0-ceramide (composed of sphingosine and a 16 carbon (palmitic) non-hydroxy fatty acid) and C18:0-ceramide (composed of sphingosine and a 18 carbon (stearic) non-hydroxy fatty acid).

As used herein, the term "a disease or disorder associated with elevated or increased ceramide levels" refers to any pathology associated with (alone or in association with other mediators) or exacerbated by elevated levels of any ceramide (e.g., C16:0-ceramide or C18:0-ceramide) or a combination thereof (e.g., C16:0-ceramide and C18:0-ceramide), or any pathology prolonged by elevated levels of any ceramide or a combination thereof in a subject having the disease or disorder. As used herein, elevated levels of ceramide include levels of any ceramide or a combination thereof in blood or tissue that are higher than a normal level considered by those of ordinary skill in the art.

Exemplary diseases or disorders associated with elevated or increased ceramide levels include, for example, insulin resistance, Alzheimer's disease, systemic lupus erythematosus, renal failure, allergic encephalomyelitis, demyelinating syndromes (e.g., central pontine myelinolysis (CPM), transverse myelitis, tabes dorsalis, and optic neuritis), multiple sclerosis, and a combination thereof.

As used herein, the term "ceramide level" refers to blood, plasma, serum, or intracellular (e.g., tissue) ceramide level. The terms "blood ceramide level," "plasma ceramide level," and "serum ceramide level" are used interchangeably herein unless otherwise clear from the context.

As used herein, the term "insulin resistance" refers to a condition in which cells (e.g., muscle, fat, and liver cells) fail to respond to the normal actions of the hormone insulin and do not properly absorb glucose from the bloodstream. In humans, insulin resistance results in excess glucose in the blood, leading to prediabetes, type 2 diabetes, and other disorders (e.g., obesity, abnormal levels of cholesterol in the blood). Insulin resistance can be identified by health care providers (e.g., doctors) based on risk factors and/or tests known in the art.

The disclosure herein pertains to metformin glycinate, compositions comprising the compound and methods of using the compound for treating various diseases in a subject. In certain aspects, the subject is a human.

Metformin glycinate, also known as 1,1-dimethylbiguanide glycinate, DMMET01 or SLN2, is a biguanide useful for the treatment of diseases such as diabetes mellitus. In certain aspects, diabetes mellitus is type 2 diabetes. Metformin glycinate can be synthesized by methods such as those disclosed in U.S. Pat. No. 8,703,183.

Metformin glycinate exhibits advantageous properties, including rapid absorption, leading to higher plasma concentrations of the drug and better bioavailability compared to metformin hydrochloride. The compound has better rheological properties compared to metformin hydrochloride, which facilitate industrial-scale handling and the preparation of pharmaceutical compositions.

Various aspects of the invention are described in further detail below.

Methods and Compositions for Treating Diabetes

In one aspect, the disclosure herein provides a method of treating diabetes in a subject in need thereof by administering a therapeutically effective amount of metformin glycinate without food, e.g., administering metformin glycinate on a substantially empty stomach. In some embodiments, metformin glycinate is administered more than about 15 minutes, about 30 minutes, about 60 minutes, about 90 minutes, about 120 minutes, about 150 minutes, about 3 hours, or about 4 hours, or about 5 hours, or about 6 hours, or about 7 hours, before or after a meal or any food intake. In some embodiments, metformin glycinate is administered more than about 15 minutes, about 30 minutes, about 60 minutes, about 90 minutes, about 120 minutes, about 150 minutes, about 3 hours, or about 4 hours before or after a meal or any food intake. Food includes solid and liquid food. Liquid food includes any nutritional liquids or liquid supplements, home-made or commercially available. In some embodiments, metformin glycinate is administered about 15 minutes, 30 minutes, 60 minutes, 90 minutes, 120 minutes, or 150 minutes before or after a meal or any food intake, in other embodiments, metformin glycinate is administered about 15 minutes, about 30 minutes, about 60 minutes, about 90 minutes, or about 120 minutes, before or after a meal or any food intake.

Advantageously, administration of metformin glycinate without food lowers the $T_{max}$ (e.g., provides a faster onset of therapeutic effects) compared to administration of metformin glycinate with food. The drug is well tolerated when administered without food; there is no detectable gastrointestinal adverse reaction.

By contrast, known adverse reactions resulting from the administration of metformin (e.g., metformin hydrochloride) include gastrointestinal adverse events, including diarrhea, flatulence, abdominal pain and dyspepsia (a group of abdominal epigastric symptoms include pain, satiety, burping and pyrosis). Consequently, it is recommended that metformin (e.g., metformin hydrochloride) be taken with food or meals, especially when administered at high doses. Thus, it is surprising that metformin glycinate is well tolerated when administered without food in view of what was known for metformin (e.g., metformin hydrochloride).

In some embodiments, the therapeutically effective amount of metformin glycinate is from about 500 mg to about 3000 mg, from about 500 mg to about 2500 mg, from about 500 mg to about 2000 mg, from about 500 mg to about 1500 mg, from about 500 mg to about 1000 mg, from about 600 mg to about 2500 mg, from about 600 mg to about 2000 mg, from about 600 mg to about 1500, from about 600 mg to about 1000 mg, from about 700 mg to about 2500 mg, from about 700 mg to about 2000 mg, from about 700 mg to about 1500 mg, from about 700 mg to about 1000 mg, from about 800 mg to about 2500 mg, from about 800 mg to about 2000 mg, from about 800 mg to about 1500 mg, from about 900 mg to about 2500 mg, from about 900 mg to about 2000 mg, from about 900 mg to about 1500 mg, from about 1000 mg to about 2500 mg, from about 1000 mg to about 2000 mg, from about 1000 mg to about 1500 mg, or any other range described herein.

In some embodiments, the therapeutically effective amount of metformin glycinate is about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, or about 3000 mg. In some embodiments, the therapeutically effective amount of metformin glycinate is about 620 mg, about 930 mg, about 1240 mg, or about 2480 mg.

In some embodiments, the therapeutically effective amount of metformin glycinate is administered once a day, twice a day, or three times a day. In some embodiments, the therapeutically effective amount of metformin glycinate is administered once a day or twice a day.

In some embodiments, the therapeutically effective amount of metformin glycinate is administered for 1, 2, 3, 4, 5, 6, 7, 8, 9, 10, 11, 12, 13, or 14 days.

In some embodiments, the subject is a human. In other embodiments, the subject is a mammal.

Combination Treatment

In some embodiments, methods of the invention comprise administering a therapeutically effective amount of metformin glycinate in combination with one or more additional anti-diabetic agents to a subject in need thereof to treat, ameliorate, or reduce diabetes and/or symptoms thereof. The one or more anti-diabetic agents include those known and those that will be developed in the future. Non-limiting known anti-diabetic agents include sulfonylureas, glinidines (also known as meglitinides), thiazolidinediones, dipeptidyl peptidase 4 (DPP4) inhibitors, sodium/glucose cotransporter 2 (SGLT2) inhibitors, glucagon-like peptide-1 (GLP1) receptor agonists, glucagon like peptide-1 (GLP-1), alpha-glucosidase inhibitors (AGIs), and insulin.

In some embodiments, the method comprises administering a therapeutically effective amount of metformin glycinate and a sulfonylurea. In some embodiments, the method comprises administering a therapeutically effective amount of metformin glycinate and a thiazolidinedione. In some embodiments, the method comprises administering a therapeutically effective amount of metformin glycinate and a DPP4 inhibitor. In some embodiments, the method comprises administering a therapeutically effective amount of metformin glycinate and a SGLT2 inhibitor. In some embodiments, the method comprises administering a therapeutically effective amount of metformin glycinate and a GLP1 agonist. In some embodiments, the method comprises administering a therapeutically effective amount of metformin glycinate and a GLP-1. In some embodiments, the method comprises administering a therapeutically effective amount of metformin glycinate and an AGI. In some embodiments, the method comprises administering a therapeutically effective amount of metformin glycinate and insulin.

In some embodiments, the method comprises administering a therapeutically effective amount of metformin glycinate and two or more anti-diabetic agents selected from a sulfonylurea, a glinidine, a thiazolidinedione, a DPP4 inhibitor, a SGLT2 inhibitor, a GLP1 receptor agonist, GLP-1, an AGI, and insulin.

When metformin glycinate is administered in combination with one or more additional anti-diabetic agents, the metformin glycinate is administered before, at the same time, or after the administration of the one or more additional anti-diabetic agents. In one embodiment, the metformin glycinate and the one or more additional anti-diabetic agents are administered concurrently. In another embodiment, the metformin glycinate and the one or more additional anti-diabetic agents are administered orally. In another embodiment, the metformin glycinate and the one or more additional anti-diabetic agents are in the same dosage form. In another embodiment, when metformin glycinate is administered with one or more additional anti-diabetic agents, the metformin glycinate is administered once daily or twice daily.

Sulfonylureas are a class of compounds useful in the treatment of diabetes (e.g., type 2 diabetes). These compounds act by increasing insulin release from the beta cells in the pancreas. Exemplary sulfonylureas include glyburide (also known as glibenclamide), gliclazide, glimepiride, glipizide, chlorpropamide, tolbutamide, and tolazamide. Therapeutic doses, dosing regiments, and routes of administration of this class of drugs for treating diabetes are known in the art.

Glinidines (also known as meglitinides) are a class of compounds useful in the treatment of diabetes (e.g., type 2 diabetes). They bind to an ATP-dependent K+(KATP) channel on the cell membrane of pancreatic beta cells resulting in increased secretion of insulin. Exemplary glinidines include repaglinide (Prandin®) and nateglinide (Starlix®). Therapeutic doses, dosing regiments, and routes of administration of this class of drugs for treating diabetes are known in the art.

Thiazolidinediones are a class of compounds useful in the treatment of diabetes (e.g., type 2 diabetes). These compounds bind to peroxisome proliferator-activated receptor gamma in adipocytes to promote adipogenesis and fatty acid uptake (in peripheral), reducing circulating fatty acid concentrations and lipid availability in liver and muscle, and thus improving the patient's sensitivity to insulin. Exemplary thiazolidinediones include rosiglitazone (Avandia®) and pioglitazone (Actos®). Therapeutic doses, dosing regiments, and routes of administration of this class of drugs for treating diabetes are known in the art.

DPP4 inhibitors are a type of antidiabetes agents for the treatment of diabetes (e.g., type 2 diabetes). DPP4 inhibitors inhibit DPP4 enzymes, which in turn inactivate glucagon-like peptide-1 (GLP-1) and glucose-dependent insulinotropic polypeptide (GIP). GLP-1 and GIP are released when food is consumed to facilitate the disposal of glucose by increasing insulin secretion. DPP4 inhibitors prevent the inactivation of GLP-1 and GIP and are useful for treating type 2 diabetes mellitus. Exemplary DPP4 inhibitors include sitagliptin (Januvia®), vildagliptin (Galvus®), saxagliptin (Onglyza®), Linagliptin (Tradjenta®), gemigliptin (approved in Korea), anagliptin (approved in Japan), teneligliptin (approved in Japan), Alogliptin (Nesina®), trelagliptin (approved in Japan), dutogliptin (Phase III trials), and omarigliptin (MK-3102, under development). Therapeutic doses, dosing regiments, and routes of administration of this class of drugs for treating diabetes are known in the art. For example, DPP4 inhibitors are used in an amount of between about 0.5 mg and about 100 mg for treating diabetes.

SGLT2 inhibitors are a type of antidiabetes agents for the treatment of diabetes (e.g., type 2 diabetes). SGLT2 inhibitors inhibit sodium-glucose co-transporter 2, reduce reabsorption of filtered glucose and lower the renal threshold for glucose, and thereby increase urinary glucose excretion. Exemplary SGLT2 inhibitors include dapagliflozin (Forxiga®), canagliflozin (Invokana®), and Empagliflozin (Jardiance®). Therapeutic doses, dosing regiments, and routes of administration of this class of drugs for treating diabetes are known in the art.

GLP1 receptor agonists are a type of antidiabetes agents for the treatment of diabetes (e.g., type 2 diabetes). GLP1 receptor agonists act on similar pathway as DPP4 inhibitors to achieve the anti-diabetic effects. Exemplary GLP1 receptor agonists include exenatide (Byetta®/Bydureon®), liraglutide (Victoza®, Saxenda®), lixisenatide (Lyxumia®), albiglutide (Tanzeum®), dulaglutide (Trulicity®), taspoglutide (under development), and semaglutide (under development). Therapeutic doses, dosing regiments, and routes of administration of this class of drugs for treating diabetes are known in the art.

GLP-1 is a neuropeptide and an incretin derived from the transcription product of the proglucagon gene. It is a potent antihyperglycemic hormone, inducing glucose-dependent stimulation of insulin secretion while suppressing glucagon secretion. There are three biologically active forms of GLP-1: GLP-1-(7-37) and GLP-1-(7-36)NH2, resulting from selective cleavage of the proglucagon molecule. Exemplary commercially available GLP-1 includes GlucaGen® and Glycagon®. Therapeutic doses, dosing regiments, and routes of administration of this class of drugs for treating diabetes are known in the art.

AGIs are a type of antidiabetic agents for the treatment of diabetes (e.g., type 2 diabetes). These compounds inhibit a number of alpha-glucosidase enzymes (e.g., maltase), consequently delaying the absorption of sugars from the gut. Acarbose (Glucobay®) is the most widely prescribed AGI. Exemplary AGIs include miglitol (Glyset®) and voglibose (Volix®, Basen®). Therapeutic doses, dosing regiments, and routes of administration of this class of drugs for treating diabetes are known in the art.

Insulin is useful for the treatment of diabetes (e.g., type 2 diabetes). Biosynthetic insulin comprising human insulin polypeptide sequence or analogues thereof (e.g., insulin zinc; protamine insulin zinc; insulin fragments or derivatives (e.g., INS-1)) can be manufactured using recombinant DNA technology in cells such as *Escherichia coli* or yeast. Therapeutic doses, dosing regiments, and routes of administration of insulin for treating diabetes are well known in the art.

Pharmaceutical Compositions Comprising Metformin Glycinate

Some embodiments of the invention are directed to a pharmaceutical composition comprising metformin glycinate. In some embodiments, the pharmaceutical composition comprises metformin glycinate and a pharmaceutically acceptable excipient. In other embodiments, the pharmaceutical composition contains a therapeutically effective amount of metformin glycinate.

The therapeutically effective amount of metformin glycinate can be administered systemically (e.g., oral, transmucosal, and injectable) or locally (e.g., topically and suppositories) via various routes known in the art. Nonlimiting exemplary routes of administration include oral, topical (e.g., transdermal), transmucosal (e.g., buccal and sublingual), injectable (e.g., intracenous, intramuscular, and subcutaneous), and inhalation (e.g., aerosol). In some embodiments, the therapeutically effective amount of metformin glycinate is administered orally. In some embodiments, the therapeutically effective amount of metformin glycinate is administered transmucosally. In some embodiments, the therapeutically effective amount of metformin glycinate is administered via injection.

The therapeutically effective amount of metformin glycinate can be formulated in various pharmaceutically compositions for administration. Nonlimiting exemplary pharmaceutical compositions include solutions, suspensions, emulsions, tablets, pills, pellets, powders, multi-particulates, capsules, capsules containing liquids, capsules containing powders, capsules containing multi-particulates, lozenges, sustained-release formulations, suppositories, transdermal patches, transmucosal films, sublingual tablets or films, aerosols, sprays, or any other form suitable for use. Various pharmaceutical compositions, pharmaceutically acceptable excipients, and methods for making pharmaceutical compositions are known in art, e.g., as described in described in *Remington's Pharmaceutical Sciences* 1447-1676 (Alfonso R. Gennaro ed., 19th ed. 1995), incorporated herein by reference in its entirety.

In some embodiments, the therapeutically effective amount of metformin glycinate is administered orally, e.g., comprised in a pharmaceutically acceptable oral dosage form. Such oral dosage forms can also comprise a suitable amount of one or more pharmaceutically acceptable excipients, including a diluent, suspending agent, solubilizer, binder, disintegrant, preservative, coloring agent, lubricant, and the like. The pharmaceutical excipients can be a liquid, such as water or oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to a human subject. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The pharmaceutical compositions, if desired, can also contain minor amounts of wetting or emulsifying agents, or pH buffering agents. Examples of pharmaceutically acceptable carriers and excipients that can be used to formulate oral dosage forms are known in the art, e.g., described in the Handbook of Pharmaceutical Excipients, American Pharmaceutical Association (1986).

In certain embodiments, metformin glycinate of the present disclosure is formulated for oral administration in the form of tablets, capsules, gelcaps, caplets, lozenges, aqueous or oily solutions, suspensions, granules, powders, emulsions, syrups, or elixirs, for example. The tablets can be compressed, enteric-coated, sugar-coated, film-coated, multiply compressed or multiply layered.

Oral dosage forms comprising metformin glycinate of the present disclosure can contain one or more additional components such as, for example, sweetening agents such as fructose, aspartame or saccharin; flavoring agents such as peppermint, oil of wintergreen, or cherry; coloring agents; preserving agents; and stabilizers to provide stable, pharmaceutically palatable dosage forms. Techniques and compositions for making solid oral dosage forms are known in the art, e.g., described in Pharmaceutical Dosage Forms: Tablets (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16$^{th}$ ed., Mack Publishing, Easton, PA 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are known in the art, e.g., described in Pharmaceutical Dosage Forms: Disperse Systems, (Lieberman, Rieger and Banker, eds.) published by Marcel Dekker, Inc.

In certain embodiments, metformin glycinate of the present disclosure is delivered in an immediate release form. In other embodiments, metformin glycinate of the present disclosure is delivered in a controlled-release system or sustained-release system. Controlled- or sustained-release pharmaceutical compositions can improve drug therapy over the results achieved by their non-controlled or non-sustained-release counterparts. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the drug compound, and can thus reduce the occurrence of adverse side effects.

Controlled- or sustained-release compositions can initially immediately release an amount of metformin glycinate of the present disclosure that promptly produces the desired therapeutic or prophylactic effect, and gradually and continually release the remaining amounts to maintain a level of therapeutic or prophylactic effect over an extended period of time. Controlled- or sustained-release of an active ingredient can be stimulated by various conditions, including but not limited to, changes in pH, changes in temperature, concentration or availability of enzymes, concentration or availability of water, or other physiological conditions or compounds. Methods for making controlled- or sustained-release oral dosage forms are known in the art, e.g., as described *Remington's Pharmaceutical Sciences* 1553-1593 (Arthur Osol, ed., 16th ed., Mack Publishing, Easton, PA 1980). In some embodiments, the controlled- or sustained-release can be prepared by methods described in e.g., U.S. Pat. No. 5,007,790, the disclosure of which is incorporated herein reference in its entirety. Such controlled- or sustained-release oral dosage forms comprise a plurality of particles of a dispersion of a drug in a hydrophilic, water-swellable, crosslinked polymer that maintains its physical integrity over the dosing lifetime but thereafter rapidly dissolves. Once ingested, the particles swell to promote gastric retention and permit the gastric fluid to penetrate the particles, thereby dissolve and release the drug.

Controlled-release and sustained-release means for use according to the present disclosure may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. Other controlled- or sustained-release systems that are discussed in the review by Langer, *Science* 249: 1527-1533 (1990) can be selected for use according to the present disclosure.

When metformin glycinate of the present disclosure is in a tablet or a pill form, the tablet or pill can be coated to delay disintegration and absorption in the gastrointestinal tract, thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Controlled- or sustained-release oral pharmaceutical compositions comprising metformin glycinate include single unit dosage forms such as, but not limited to, tablets, capsules, gelcaps, and caplets. In some embodiments, the oral dosage forms are tablets or capsules.

The pharmaceutical compositions (e.g., oral dosage forms) comprising metformin glycinate can be administered once a day, twice a day, or three times a day. In some embodiments, the pharmaceutical compositions are administered once a day or twice a day. Typically, immediate-release dosage forms are administered more frequently than controlled- or sustained-release dosage forms.

The pharmaceutical compositions can comprise various amount of metformin glycinate. In some embodiments, the amount of metformin glycinate in a pharmaceutical composition is from about 500 mg to about 3000 mg, from about 500 mg to about 2500 mg, from about 500 mg to about 2000 mg, from about 500 mg to about 1500 mg, from about 500 mg to about 1000 mg, from about 600 mg to about 2500 mg, from about 600 mg to about 2000 mg, from about 600 mg to about 1500, from about 600 mg to about 1000 mg, from about 700 mg to about 2500 mg, from about 700 mg to about 2000 mg, from about 700 mg to about 1500 mg, from about 700 mg to about 1000 mg, from about 800 mg to about 2500 mg, from about 800 mg to about 2000 mg, from about 800 mg to about 1500 mg, from about 900 mg to about 2500 mg, from about 900 mg to about 2000 mg, from about 900 mg to about 1500 mg, from about 1000 mg to about 2500 mg, from about 1000 mg to about 2000 mg, from about 1000 mg to about 1500 mg, or any other range described herein. In some embodiments, the amount of metformin glycinate in a pharmaceutical composition is about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 3000 mg, or any other amount described herein. In some embodiments, the amount of metformin glycinate in a pharmaceutical composition is about 620 mg, about 930 mg, about 1240 mg, or about 2480 mg.

In some embodiments, the metformin glycinate pharmaceutical composition disclosed herein further comprises one or more additional anti-diabetic agents. In some embodiments, the pharmaceutical composition comprising metformin glycinate and the one or more additional antidiabetics agents is an oral pharmaceutical composition. In some embodiments, the oral pharmaceutical composition is a solid oral composition. In some embodiments, the solid oral pharmaceutical composition is a tablet, a capsule, a gelcap, a caplet, or a lozenge.

In some embodiments, the one or more anti-diabetic agents include those known and will be developed in the future. Non-limiting known anti-diabetic agents include sulfonylureas, glinidines, thiazolidinediones, DPP4 inhibitors, SGLT2 inhibitors, GLP1 receptor agonists, GLP-1, AGIs, insulin. Description of each class of the anti-diabetic agents and exemplary compounds in each class are disclosed above.

In some embodiments, the solid oral composition comprises metformin glycinate and a sulfonylurea. In other embodiments, the solid oral composition comprises metformin glycinate and a glinidine. In some embodiments, the solid oral composition comprises metformin glycinate and a thiazolidinedione. In some embodiments, the solid oral composition comprises metformin glycinate and a DPP4 inhibitor. In some embodiments, the solid oral composition comprises metformin glycinate and a SGLT2 inhibitor. In some embodiments, the solid oral composition comprises metformin glycinate and a GLP1 receptor agonist. In some embodiments, the solid oral composition comprises metformin glycinate and GPL-1. In some embodiments, the solid oral composition comprises metformin glycinate and an AGI. In some embodiments, the solid oral composition comprises metformin glycinate and insulin. In some embodiments, the solid oral composition comprises metformin glycinate and two or more anti-diabetic agents selected from a sulfonylurea, a glinidine, a thiazolidinedione, a DPP4 inhibitor, a SGLT2 inhibitor, a GLP1 receptor agonist, and an AGI. Exemplary compounds in each class of the anti-diabetic drugs are disclosed herein.

The amount of metformin glycinate and other anti-diabetic agents in the solid oral compositions can be determined in view of the daily dose of each drug contained in the composition, dosing frequency, and manufacturing considerations, which can be determined by those of ordinary skill in the art. Methods and excipients for making oral pharmaceutical compositions are disclosed herein.

Methods of Treating Obesity

In one aspect, the disclosure herein provides a method of treating obesity comprising administering to a subject in need thereof a therapeutically effective amount of metformin glycinate. In another aspect, the disclosure herein provides a method of reducing weight in a subject comprising administering to a subject in need thereof a therapeutically effective amount of metformin glycinate. Metformin glycinate reduces leptin levels in a subject.

Obesity as used herein refers to a condition of abnormal or excessive accumulation of adipose tissue, to the extent that health of a subject may be impaired. Obesity can be measured by the body mass index (BMI; $kg/m^2$) in humans, which refers to the weight in kilograms divided by the square of the height in meters. BMI is a commonly used index to classify overweight and obesity in adults. According to the WHO BMI classification for adults, underweight: BMI<18.5 $kg/m^2$, normal weight: BMI between 18.5 $kg/m^2$ and higher to 24.99 $kg/m^2$, overweight: BMI 25 $kg/m^2$ and higher to 29.99 $kg/m^2$, obese grade I: BMI 30 $kg/m^2$ and higher to 34.99 $kg/m^2$, obese grade II: BMI 35 $kg/m^2$ and higher to 39.99 $kg/m^2$, obese grade III and more: BMI≥40 $kg/m^2$. See who.int/features/factfiles/obesity/facts/en/. Thus, human adults with a BMI of 25 $kg/m^2$ and higher (e.g., overweight or obese adult humans) can be treated with the method.

In some embodiments, the method comprises administering a therapeutically effective amount of metformin glycinate to a subject (e.g., an adult human) with a BMI of ≥25 $kg/m^2$, in other embodiments, the method comprises administering a therapeutically effective amount of metformin glycinate to a subject (e.g., an adult human) with a BMI of ≥30 $kg/m^2$, in other embodiments, the method comprises administering a therapeutically effective amount of metformin glycinate to a subject (e.g., an adult human) with a BMI of ≥35 $kg/m^2$, in other embodiments, the method comprises administering a therapeutically effective amount of metformin glycinate to a subject (e.g., an adult human) with a BMI of ≥40 $kg/m^2$.

In some embodiments, the method comprises administering a therapeutically effective amount of metformin glycinate to a subject (e.g., an adult human) with a BMI of from 25 $kg/m^2$ and higher to 29.99 $kg/m^2$, in other embodiments, the method comprises administering a therapeutically effective amount of metformin glycinate to a subject (e.g., an adult human) with a BMI of from 30 $kg/m^2$ and higher to 34.99 $kg/m^2$, in yet other embodiments, the method comprises administering a therapeutically effective amount of metformin glycinate to a subject (e.g., an adult human) with a BMI of from 35 $kg/m^2$ and higher to 39.99 $kg/m^2$, in other embodiments, the method comprises administering a therapeutically effective amount of metformin glycinate to a subject (e.g., an adult human) with a BMI of ≥40 $kg/m^2$.

The therapeutic effective amount of metformin glycinate for treating an overweight or obese subject may depend on several factors including the degree of the condition (e.g., as reflected by the BMI of the subject), age of the subject and whether the subject has other diseases or conditions (e.g., decreased renal function of the subject). The goal of the treatment is to reduce body fat, e.g., bring the BMI of the subject to be within the normal weight range of between 18.5 $kg/m^2$ and higher to 24.99 $kg/m^2$. The treatment can be supplemented with lifestyle change, e.g., exercise and/or reducing dietary caloric intake.

In some embodiments, the therapeutically effective amount of metformin glycinate that can be used in the method is from about 500 mg to about 3000 mg, from about 500 mg to about 2500 mg, from about 500 mg to about 2000 mg, from about 500 mg to about 1500 mg, from about 500 mg to about 1000 mg, from about 600 mg to about 2500 mg, from about 600 mg to about 2000 mg, from about 600 mg to about 1500 mg, from about 600 mg to about 1000 mg, from about 700 mg to about 2500 mg, from about 700 mg to about 2000 mg, from about 700 mg to about 1500 mg, from about 700 mg to about 1000 mg, from about 800 mg to about 2500 mg, from about 800 mg to about 2000 mg, from about 800 mg to about 1500 mg, from about 900 mg to about 2500 mg, from about 900 mg to about 2000 mg, from about 900 mg to about 1500 mg, from about 1000 mg to about 2500 mg, from about 1000 mg to about 2000 mg, from about 1000 mg to about 1500 mg, or any other range described herein. In other embodiments, the therapeutically effective amount of metformin glycinate is from about 500 mg to about 2500 mg, from about 500 mg to about 2000 mg, from about 500 mg to about 1500 mg, or from about 500 mg to about 1000 mg. In other embodiments, the therapeutically effective amount of metformin glycinate is about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 3000 mg, or any other amount described herein. In some embodiments, the therapeutically effective amount of metformin glycinate is about 620 mg, about 930 mg, about 1240 mg, or about 2480 mg.

The therapeutically effective amount of metformin glycinate can be administered using any of the pharmaceutical compositions or delivery routes described herein. For example, the therapeutically effective amount of metformin glycinate can be administered systemically or locally via various routes known in the art. Nonlimiting exemplary routes of administration include oral, topical, transmucosal, injectable, and inhalation. In some embodiments, the therapeutically effective amount of metformin glycinate is administered orally, e.g., using an oral dosage form. The oral dosage form can be liquid (e.g., oral solution or oral suspension) or solid (e.g., tablets or capsules). In some embodiments, the therapeutically effective amount of metformin glycinate is administered once a day, twice a day, or three times a day, preferably in an oral dosage form. Oral dosage forms and methods of making those dosage forms are disclosed herein.

In some embodiments, the therapeutically effective amount of metformin glycinate is administered once a day, twice a day, or three times a day. In some embodiments, the therapeutically effective amount of metformin glycinate is administered once a day or twice a day.

In some embodiments, the subject in need thereof of the method is a human. In other embodiments, the subject is a mammal.

Methods of Treating Dyslipidemia and Cardiovascular Diseases

In one aspect, the disclosure provides a method of treating dyslipidemia comprising administering to a subject in need thereof a therapeutically effective amount metformin glycinate.

Dyslipidemia refers to a disorder with abnormal amounts of lipids in the blood. It is characterized by an elevated blood TG, an elevated blood LDL, a low level of HDL, a high level of total blood cholesterol, an elevated blood apoB level, an elevated blood apoA1 level, or a combination thereof. Total blood cholesterol level can be determined by methods known in the art, e.g., using the equation: HDL+LDL+20 percent of TG level. There are general guidelines for blood HDL, LDL, TG, apoA1, apoB, and total cholesterol levels.

Risk factors for dyslipidemia include primary (e.g., genetic) and/or secondary (e.g., lifestyle). Common secondary causes for dyslipidemia include sedentary lifestyle, excessive dietary intake of saturated fat, cholesterol, and trans fats, alcohol overuse, smoking, obesity, other diseases such as HIV infection, nephrotic syndrome, diabetes mellitus, hypothyroidism, primary biliary cirrhosis and other cholestatic liver diseases, chronic kidney disease, and drugs (e.g., thiazides, β-blockers, retinoids, highly active antiretroviral agents, cyclosporine, tacrolimus, estrogen and progestins, and glucocorticoids).

In humans, generally the target normal LDL level is less than 160 mg/dL (4.15 mmol/L) for patients with one risk factor, and 130 mg/dL (3.35 mmol/L) or less for patients with two or more risk factors. The target normal HDL level is 60 mg/dL or greater, the target normal TG level is 150 mg/dL or less, and the target normal total cholesterol level is 200 mg/dL (5.15 mmol/L) or less. The target apo B level is <90 mg/dL (patients with risk of CAD) or <80 mg/dL (patients with established CAD). AACE Guidelines, accessible at aace.com/files/lipid-guidelines.pdf. Blood HDL, LDL, TG, and total cholesterol levels can be determined by measuring fast lipid profile of a patient. Such measurements are well known in the art, e.g., can be performed by a clinical laboratory.

Any subject (e.g., human patients) who have one or more of blood LDL, TG, apoA1, apoB, and total cholesterol levels above the target normal levels, or the blood HDL level below the target normal level may be treated by the method disclosed herein. In some embodiments, the treatment reduces one or more of the blood LDL, TD, apoA1, apoB, and total blood cholesterol levels, or increases the blood HDL level, compared to that before the treatment. In certain embodiments, the treatment reduces one or more of the blood LDL, TG, apoA1, apoB, and total cholesterol levels, or raises the blood HDL level to be within the target normal level.

In some embodiments, the method comprises administering a therapeutically effective amount of metformin glycinate to a subject to treat or ameliorate dyslipidemia, or treat or ameliorate or reduce the symptoms associated with dyslipidemia. In some embodiments, the treatment lowers the blood TG level, lowers the blood LDL level, lowers the blood apoB level, lowers the blood apoA1 level, raises the blood HDL level, lowers the total cholesterol level in the blood or a combination thereof. In some embodiments, the treatment reduces the blood LDL, TG, apoA1, apoB, total cholesterol levels, or raises blood HDL level to be within the target range in the subject.

According to the third National Health and Nutrition Examination Survey (NHANES III) database 35% of men and 13% of women have low blood serum HDL cholesterol levels (e.g., less than 40 mg/L). Various studies have shown that individuals with low HDL levels have a higher incidence of cardiovascular (CV) events than those with HDL levels greater than 65 mg/L. In the Framingham Heart Study, about 44% of coronary events were observed in persons with HDL levels less than 40 mg/L (Castelli 1986). Accordingly to the AACE Guidelines, dyslipidemia is a primary, major risk factor for CAD and may even be a prerequisite for CAD. In addition, dyslipidemia/hypercholesterolemia and CAD are risk factors for cardiovascular events such as stroke, angina, and heart attack.

Therefore, in some embodiments, methods of the invention comprise administering a therapeutically effective amount of metformin glycinate to a subject to treat a heart disease such as atherogenesis, atherosclerosis, CAD, angina, heart attack, stroke, or a combination thereof. In some embodiments, the method comprises administering a therapeutically effective amount of metformin glycinate to a subject to treat atherosclerosis, CAD, angina, heart attack, stroke, or a combination thereof. In some embodiments, the method comprises administering a therapeutically effective amount of metformin glycinate to a subject to treat atherosclerosis, CAD, or a combination thereof. In some embodiments, the method comprises administering a therapeutically effective amount of metformin glycinate to a subject to treat atherosclerosis, in other embodiments, the method comprises administering a therapeutically effective amount of metformin glycinate to a subject to treat CAD.

The therapeutic effective amount of metformin glycinate for treating dyslipidemia and/or heart diseases (e.g., one or more of atherogenesis, atherosclerosis, CAD, angina, heart attack, and stroke) in a subject (e.g., a human) may depend on several factors including the degree of the condition (e.g., one or more blood LDL, TG, HDL, total cholesterol, apoA1, and apoB levels), age and gender of the subject, and whether the subject has other diseases or conditions (e.g., diabetes and hypothyroidism). The goal of the treatment is to bring the blood lipids level to be within the normal range.

In some embodiments, the therapeutically effective amount of metformin glycinate that can be used in the method is from about 500 mg to about 3000 mg, from about 500 mg to about 2500 mg, from about 500 mg to about 2000 mg, from about 500 mg to about 1500 mg, from about 500 mg to about 1000 mg, from about 600 mg to about 2500 mg, from about 600 mg to about 2000 mg, from about 600 mg to about 1500 mg, from about 600 mg to about 1000 mg, from about 700 mg to about 2500 mg, from about 700 mg to about 2000 mg, from about 700 mg to about 1500 mg, from about 700 mg to about 1000 mg, from about 800 mg to about 2500 mg, from about 800 mg to about 2000 mg, from about 800 mg to about 1500 mg, from about 900 mg to about 2500 mg, from about 900 mg to about 2000 mg, from about 900 mg to about 1500 mg, from about 1000 mg to about 2500 mg, from about 1000 mg to about 2000 mg, from about 1000 mg to about 1500 mg, or any other range described herein. In other embodiments, the therapeutically effective amount of metformin glycinate is from about 500 mg to about 2500 mg, from about 500 mg to about 2000 mg, from about 500 mg to about 1500 mg, or from about 500 mg to about 1000 mg. In other embodiments, the therapeutically effective amount of metformin glycinate is about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 3000 mg, or any other amount described herein. In some embodiments, the therapeutically effective amount of metformin glycinate is about 620 mg, about 930 mg, about 1240 mg, or about 2480 mg.

The therapeutically effective amount of metformin glycinate can be administered using any of the pharmaceutical compositions or delivery routes described herein. For example, the therapeutically effective amount of metformin glycinate can be administered systemically or locally via various routes known in the art. Nonlimiting exemplary routes of administration include oral, topical, transmucosal, injectable, and inhalation. In some embodiments, the therapeutically effective amount of metformin glycinate is administered orally, e.g., using an oral dosage form. The oral dosage form can be liquid (e.g., oral solution or oral suspension) or solid (e.g., tablets or capsules). In some embodiments, the therapeutically effective amount of metformin glycinate is administered once a day, twice a day, or three times a day, preferably in an oral dosage form. Oral dosage forms and methods of making those dosage forms are disclosed herein.

In treating dyslipidemia and/or heart diseases such as atherogenesis, atherosclerosis, CAD, angina, heart attack, stroke, or a combination thereof, metformin glycinate can be used together with one or more additional active agents. The one or more additional active agents include drugs from various lipid-lowering drug classes, including (1) HMG-CoA reductase inhibitors (e.g., statins such as lovastatin, pravastatin, fluvastatin, simvastatin, atorvastatin, rosuvastatin, and pitavastatin), (2) Fibric acid derivatives (e.g., gemfibrozil, fenofibrate, and fenofibric acid), (3) Niacin (e.g., nicotinic acid), (4) Bile acid sequestrants (e.g., cholestyramine, colestipol, colesevelam, and hydrochloride), (5) Cholesterol absorption inhibitors (e.g., ezetimibe), or a combination thereof (e.g., ezetimibe/simvastatin and niacin/simvastatin). The amount of the one or more additional active agents for treating dyslipidemia and/or heart diseases (e.g., atherogenesis, atherosclerosis, CAD, angina, heart attack, stroke, or a combination thereof) is known in the art, e.g., see the AACE Guidelines.

The one or more additional active agents can be administered together (e.g., at the same time) with metformin glycinate or separately (e.g., before or after). In some embodiments the one or more additional active agents are in the same dosage form as metformin glycinate. In some embodiments, metformin glycinate is formulated in the same dosage form such as a HMG-CoA reductase inhibitor. Also the treatment (e.g., metformin glycinate alone or in combination with the one or more active agents) can be supplemented with lifestyle change, e.g., exercise and/or reducing dietary caloric intake.

In some embodiments, the subject in need thereof of the method is a human. In other embodiments, the subject is a mammal.

Method of Treating Diseases Associated with IL-10 Up-regulation

In one aspect, the disclosure provides a method of treating a disease associated with IL-10 up-regulation comprising administering to a subject in need thereof a therapeutically effective amount metformin glycinate.

IL-10 is an anti-inflammatory cytokine that inhibits cytokine synthesis. Fioranelli M. and Grazia R. M., "Twenty-five years of studies and trials for the therapeutic application of IL-10 immunomodulating properties. From high doses administration to low dose medicine new paradigm," *Journal of Integrative Cardiology* Vol. 1(1): 2-6 (2014). Its inhibitory action is exerted mainly against the inflammation markers such as IL-1, IL-6, TNF-α, GM-CSF and IFN-γ. In addition, IL-10 also inhibits the production of anti-inflammatory factors including soluble TNF-α receptors and IL-1RA. IL-10 is produced by various cell types including lymphocytes, monocytes and macrophages.

IL-10 up-regulation is associated with increased risk of cancer development, viral infection chronicization, and the onset of Th2 dependent autoimmune, inflammatory and allergic disorders. IL-10 is up-regulated or over-expressed in many malignant diseases such as melanoma, carcinoma, lymphoma, and tumor cells derived from NK, T and B cell lymphomas. High levels of IL-10 are associated with disease progression, metastasize and immune suppression of these cancers. There is also a correlation between high levels of IL-10 and vascular endothelial growth factor (VEGF) over-expression in some types of esophageal cancer. Increased IL-10 levels are linked to poor prognosis, unresponsiveness to chemotherapy and tumor recurrence after surgery.

IL-10 up-regulation can lead to an inappropriate clearance of pathogens, which can aid immune escape of viruses such as HIV, HBV, HCV, EBV and HPV. Th2-driven allergic response (e.g., food allergy, asthma, eosinophilic esophagitis, and atopic dermatitis) is associated with IL-10 overexpression.

Metformin glycinate inhibits IL-10 expression in macrophages stimulated with lipopolysaccharide (LPS, a bacterial virulence factor with a strong proinflammatory activity) and IFN-γ. By contrast, metformin hydrochloride increases IL-10 expression in macrophages stimulated with LPS and IFN-γ. In addition, metformin glycinate inhibits cancer cell growth and induces apoptosis (cell death) of cancer cells in vitro.

Thus, in some embodiments, methods of the invention comprise administering a therapeutically effective amount of metformin glycinate for the treatment of diseases associated with IL-10 up-regulation such as cancers (e.g., melanoma, carcinoma, lymphoma, esophageal cancers, tumors derived from NK, T and B cell lymphomas) and allergic diseases (e.g., food allergy, asthma, eosinophilic esophagitis and atopic dermatitis).

In some embodiments, the method comprises administering a therapeutically effective amount of metformin glycinate to a subject to treat melanoma, carcinoma, or lymphoma. In some embodiments, the cancers are metastasized. In some embodiments, the method comprises administering a therapeutically effective amount of metformin glycinate to a subject to treat food allergy, asthma, eosinophilic esophagitis, atopic dermatitis, or a combination thereof. In some embodiments, the method comprises administering a therapeutically effective amount of metformin glycinate to a subject to treat asthma or atopic dermatitis.

The therapeutic effective amount of metformin glycinate for treating diseases associated with IL-10 up-regulation (e.g., cancers such as one or more of melanoma, carcinoma, lymphoma, esophageal cancers, tumors derived from NK, T and B cell lymphomas or allergic diseases such as food allergy, asthma, eosinophilic esophagitis and atopic dermatitis) in a subject (e.g., a human) may depend on factors such as the type of disease (e.g., cancers or allergic diseases) and age and gender of the subject.

In some embodiments, the therapeutically effective amount of metformin glycinate that can be used in a method of the invention is from about 500 mg to about 3000 mg, from about 500 mg to about 2500 mg, from about 500 mg to about 2000 mg, from about 500 mg to about 1500 mg, from about 500 mg to about 1000 mg, from about 600 mg to about 2500 mg, from about 600 mg to about 2000 mg, from about 600 mg to about 1500 mg, from about 600 mg to about 1000 mg, from about 700 mg to about 2500 mg, from about 700 mg to about 2000 mg, from about 700 mg to about 1500 mg, from about 700 mg to about 1000 mg, from about 800 mg to about 2500 mg, from about 800 mg to about 2000 mg, from about 800 mg to about 1500 mg, from about 900 mg to about 2500 mg, from about 900 mg to about 2000 mg, from about 900 mg to about 1500 mg, from about 1000 mg to about 2500 mg, from about 1000 mg to about 2000 mg, from about 1000 mg to about 1500 mg, or any other range described herein. In other embodiments, the therapeutically effective amount of metformin glycinate is the therapeutically effective amount of metformin glycinate is from about 500 mg to about 2500 mg, from about 500 mg to about 2000 mg, from about 500 mg to about 1500 mg, or from about 500 mg to about 1000 mg. In other embodiments, the therapeutically effective about of metformin glycinate is about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 3000 mg, or any other amount described herein. In some embodiments, the therapeutically effective amount of metformin glycinate is about 620 mg, about 930 mg, about 1240 mg, or about 2480 mg.

The therapeutically effective amount of metformin glycinate can be administered using any of the pharmaceutical compositions or delivery routes described herein. For example, the therapeutically effective amount of metformin glycinate can be administered systemically or locally via various routes known in the art. Nonlimiting exemplary routes of administration include oral, topical, transmucosal, injectable, and inhalation. In some embodiments, the therapeutically effective amount of metformin glycinate is administered orally, e.g., using an oral dosage form. The oral dosage form can be liquid (e.g., oral solution or oral suspension) or solid (e.g., tablets or capsules). In some embodiments, the therapeutically effective amount of metformin glycinate is administered once a day, twice a day, or three times a day, preferably in an oral dosage form. Oral dosage forms and methods of making those dosage forms are disclosed herein.

In treating cancers such as melanoma, carcinoma, or lymphoma, metformin glycinate can be used together with one or more additional active agents useful for treating these cancers. The one or more additional active agents include ipilimumab (Yervoy®), pembrolizumab (Keytruda®), nivolumab (Opdivo®), talimogene laherparepvec (T-VEC, Imlygic™), Zelboraf (vemurafenib), Tafinlar (dabrafenib), and Mekinist (trametinib). In some embodiments, the metformin glycinate is administered orally while the one or more anticancer drugs are administered injectably (e.g., intravenous, intramuscular, or subcutaneously). In some embodiments, both the metformin glycinate and the anticancer drugs are administered orally. The amount of the one or more additional active agents for treating cancers such as melanoma, carcinoma, or lymphoma is known in the art.

In treating allergic diseases such as food allergy, asthma, eosinophilic esophagitis, and atopic dermatitis, metformin glycinate can be used together with one or more additional active agents. The one or more additional active agents include antihistamines such as loratadine, diphendydramine, and cetirizine, steroids such as betamethasone, cortisone, dexamethasone, hydrocortisone, methylprednisolone, prednisolone, prednisone, and triamcinolone, and bronchodilators such as salbutamol and salmeterol. In some embodiments, a therapeutic effective amount of metformin glycinate is administered together with one or more antihistamines for the treatment of asthma or atopic dermatitis. In some embodiments, a therapeutic effective amount of metformin glycinate is administered together with one or more steroids for the treatment of asthma or atopic dermatitis. In some embodiments, the metformin glycinate and the one or more antihistamines are administered orally. In some embodiments, the metformin glycinate is administered orally while the one or more steroids are administered topically. In some embodiments, the metformin glycinate and the one or more steroids are administered orally. The amount of an antihistamine for treating asthma or atopic dermatitis is known in the rat. Similarly, the amount of a steroid for treating asthma or atopic dermatitis is known in the rat.

The one or more additional active agents can be administered together (e.g., at the same time) with metformin glycinate or separately (e.g., before or after). In some embodiments the one or more additional active agents and metformin glycinate are in the same dosage form. In some embodiments, the dosage form is an oral dosage form.

In some embodiments, metformin glycinate and an antihistamine such as loratadine, diphendydramine, and cetirizine are in the same oral dosage form (e.g., tablets or capsules). In some embodiments, metformin and glycinate and a steroid such as betamethasone, cortisone, dexamethasone, hydrocortisone, methylprednisolone, prednisolone, prednisone, and triamcinolone are in the same oral dosage form (e.g., tablets or capsules).

In some embodiments, the therapeutically effective amount of metformin glycinate is administered once a day, twice a day, or three times a day. In some embodiments, the therapeutically effective amount of metformin glycinate is administered once a day or twice a day.

In some embodiments, the subject in need thereof of the method is a human. In other embodiments, the subject is a mammal.

Method of Treating Diseases Associated with Elevated or Increased Blood Ceramide Level Ceramides are a family of lipid molecules. A ceramide is composed of sphingosine and a fatty acid that varies in length from 14 to 26 carbon atoms. Common ceramides include C16:0-ceramide and C18:0 ceramide.

Ceramides are found in high concentrations within the cell membrane of cells, as they are component lipids that make up sphingomyelin, one of the major lipids in the lipid bilayer. Ceramides participate in a variety of cellular signaling including regulating differentiation, proliferation, and programmed cell death (PCD) of cells. For example, C16:0 ceramide is believed to be a major mediator of insulin resistance. Hla T and Kolesnick R, "C16:0-ceramide signals insulin resistance" *Cell Metab.* 20(5): 703-5 (2014). Ceramide levels in an animal (e.g., a human) can be determined by, e.g., liquid chromatography/mass spectroscopy or electrospray ionization tandem mass spectrometry (ESI-MS/MS) analysis of blood and/or tissue samples.

Human Goodpasture antigen-binding protein (GPBP), encoded by the COL4A3BP gene, is an atypical protein kinase that phosphorylates the Goodpasture auto-antigen, the α3 chain of collagen IV. The COL4A3BP gene is alternatively spliced, producing two protein isoforms: GPBP and GPBPΔ26. The latter lacks a serine-rich domain composed of 26 amino acid residues. Both isoforms also function as ceramide transfer proteins (CERT). Granero-Molto et al., "Goodpasture Antigen-binding Protein and Its Spliced Variant, Ceramide Transfer Protein, Have Different Functions in the Modulation of Apoptosis during Zebrafish Development," *J Biol Chem.* 283(29): 20495-20504 (2008). GPBP/CERT transfers ceramides (e.g., C16:0-ceramide) from the endoplasmic reticulum (ER) to the Golgi apparatus where sphingolipids are synthesized. GPBP/CERT can be phosphorylated and phosphorylation leads to inactivation of the ceramide transferring activities of the protein. Thus, deficiency or absence of GPBP/CERT and/or GPBP/CERT phosphorylation leads to intracellular ceramide accumulation, which is believed to be one of the causes of insulin resistance and/or pre-diabetes. Turpin S M, et al. "Obesity-Induced CerS6-Dependent C16:0 Ceramide Production Promotes Weight Gain and Glucose Intolerance," *Cell Metab.* 20: 678-686 (2014).

Increased ceramide levels is associated with various other diseases or disorders including Alzheimer's disease, systemic lupus erythematosus, renal failure (e.g., diabetic neuropathy and following ischaemia/reperfusion), allergic encephalomyelitis, demyelinating syndromes and multiple sclerosis. Non-limiting examples of demyelinating syndromes include central pontine myelinolysis (CPM)(also known as osmotic demyelination syndrome or central pontine demyelination), transverse myelitis, tabes dorsalis (also known as syphilitic myelopathy), and optic neuritis (also known as optic papillitis). Kamal SHARMA and Yufang S H I, "The Yins and Yangs of Ceramide," *Cell Research* 9: 1-10 (1999), Maja Jazvinšćak Jembrek et al., "Ceramides in Alzheimer's Disease: Key Mediators of Neuronal Apoptosis Induced by Oxidative Stress and Aβ Accumulation," Vol. 2015 (2015), Article ID 346783.

Surprisingly, metformin glycinate, but not metformin hydrochloride, significantly reduces ceramide levels. Also surprisingly, metformin glycinate, but not metformin hydrochloride, inhibits or reduces phosphorylation of GPBP/CERT, resulting in intracellular ceramide transport and lowers or reduces ceramide levels.

Thus in one aspect, the disclosure provides a method of treating a disease or disorder associated with elevated or increased ceramide levels (e.g., blood ceramide level) comprising administering to a subject in need thereof a therapeutically effective amount metformin glycinate. In some embodiments, the disease or disorder is insulin resistance or pre-diabetes, Alzheimer's disease, systemic lupus erythematosus, renal failure, allergic encephalomyelitis, demyelinating syndromes (e.g., CPM, transverse myelitis, tabes dorsalis, and optic neuritis), multiple sclerosis, or a combination thereof. In some embodiments, the disease or disorder is insulin resistance, Alzheimer's disease, multiple sclerosis, systemic lupus erythematosus, or a combination thereof. In some embodiments, the disease or disorder is insulin resistance. In some embodiments, the disease or disorder is Alzheimer's disease.

The therapeutically effective amount of metformin glycinate is an amount that lowers the ceramide level in the subject compared to the ceramide level before the administration. In some embodiments, the therapeutically effective amount of metformin glycinate is from about 500 mg to about 3000 mg, from about 500 mg to about 2500 mg, from about 500 mg to about 2000 mg, from about 500 mg to about 1500 mg, or from about 500 mg to about 1000 mg, or any other dose or range of doses described herein.

The therapeutically effective amount of metformin glycinate can be administered by any route or composition described herein, for example, by the subject or by one other than the subject systemically (e.g., oral, transmucosal, and injectable) or locally (e.g., topically and suppositories) via various well known routes. Nonlimiting exemplary routes of administration include oral, topical (e.g., transdermal), transmucosal (e.g., buccal and sublingual), injectable (e.g., intravenous, intramuscular, and subcutaneous), and inhalation (e.g., aerosol). In some embodiments, the metformin glycinate is administered orally in a single dose or in divided dose (e.g., twice or more times a day). Oral dosage forms and their preparation are disclosed herein.

In some embodiments, the subject in need thereof of the method is a human. In other embodiments, the subject is a mammal.

GPBP, CERT, and Ceramides

GPBP/CERT (Goodpasture Antigen-Binding Protein) is also known as CERT (ceramide transfer protein); CERTL (ceramide transfer protein); and STARD11. It is a kinase serine/threonine that phosphorylates the non-collagenous domain (NC1) of the α3 chain of Type IV collagen in basal membranes. This domain is also known as Goodpasture's autoantigen, since it is the specific target of auto-antibodies that cause glomerulonephritis and pulmonary hemorrhage in Goodpasture Syndrome. Raya A et al., *J. Biol. Chem.* 274: 12642-9 (1999).

The coding gene for GPBP/CERT, COL4A3BP, expresses three polypeptides: GPBP/CERT1 (CERT1), GPBP/CERT2 (STARD11), and GPBP/CERT3. Raya A et al., *J. Biol. Chem.* 275: 40392-9 (2000); Revert F et al., *J. Biol. Chem.* 283: 30246-55 (2008).

GPBP/CERT1 is a protein that is secreted into the extracellular media and that regulates the organization of Type IV collagen net. Calvete J J, et al. *Proteomics.* 2006. GPBP/CERT2 is located in the cytosol and its main function involves transferring ceramide between the endoplasmic reticulum and the Golgi apparatus. It participates in the phosphorylated and dephosphorylated forms in intracellular signaling mechanisms, and regulates protein secretion as Type IV collagen. Revert F et al., *J Biol Chem.* 83: 30246-55 (2008). GPBP/CERT3 is an isoform bound to the external wall of the plasma membrane, that regulates GPBP/CERT1 exportation. In the striated muscle, where alternative isoforms are not expressed, GPBP/CERT1 remains in the cytoplasm and regulates myofibrillar organization through its interaction with a new protein family denominated GIP proteins (GPBP/CERT interacting proteins). In summary, GPBP/CERT1 regulates protein assembly in both intracellular and extracellular behavior. Revert F et al., *J Biol Chem.* 283: 30246-55 (2008).

An increase in GPBP's expression has been associated with several disorders, including autoimmunity (renal and articular), inflammation (fibrosis), type 2 diabetes, and cancer. Granero F et al., *FEBS J.* 272: 5291-305 (2005); Miralem T et al., *J Biol Chem.* 285: 12551-8 (2010).

Ceramides play an important role in diabetes by means of at least three different mechanisms: inducing apoptosis in pancreatic β cells, increasing insulin resistance, and reducing insulin genetic expression. Recent studies have linked high intracellular ceramide levels as key mediators in insulin resistance. This type of lipid is composed of a sphingosine column conjugated with a fatty acid derivate, and is found in all cell types. On the other hand, it should be noted that lipids' role in insulin resistance has been widely observed and it is an accepted mechanism. It is still under research if plasma circulating lipids or lipid accumulation in insulin-dependent cell types should be considered as a triggering mechanism in the insulin resistance phenomenon.

Consumption of food rich in saturated fatty acids, such as butter, cream, and red meat, has become common in the Western diet. Therefore, ceramides play a more important and clinically relevant role in individuals with diet-induced obesity, observed in developed nations, than previously assumed.

Ceramides are generated by 3 different pathways: 1) de novo, 2) by direct generation via sphingomyelin division by sphingomyelinase, or 3) by the "salvage pathway" through direct decomposition of sphingolipids in sphingosine, which can be converted in ceramides by the ceramide synthase. J. Y Xia et al., *Biochimie* 96: 130-139 (2014). Alterations in enzymatic activity in any of these steps can dramatically alter intracellular levels of these lipid fractions, a process that may be beneficial or fatal for the cell, depending on the physiological conditions. Since these three pathways may be active in a parallel manner, their inhibition may have either deep consequences or a marginal effect in cellular physiology, depending on cell type, development state or nutritional state.

Ceramides are essential for the phospholipid bilayer development in the cell membrane. Besides this structural role, ceramides also play an important role in cell signaling, inflammation, and apoptosis. Once generated, ceramides are common precursors of a series of complex sphingolipids, and they may also be glycosylated, deacetylated, and phosphorylated to produce a variety of metabolites and signaling molecules. The de novo ceramide generation pathway can be induced by a diet rich in saturated fat, an increase in diet serins, oxidative stress and oxidized LDL. Additionally, it has been demonstrated that inflammatory cytokines, such as TNFα and IL-1, may increase SPT enzyme expression and activity, leading to an increase in de novo ceramide synthesis. Sawada M et al., *Cell Death Differ.* 11(9): 997-1008 (2004).

Human plasma and murine are a rich source of ceramides, which circulate in the 0.5-10 μM micromolar range. Around 75% of these ceramides are contained in VLDL and LDL particles, and the rest in HDL. Due to its stable association with these lipoproteins, scientists may hypothesize that the primary source of circulating ceramides is the liver. This hypothesis has already been proven. However, the matter regarding the information that plasma ceramide levels reveal is far from being solved. So far, plasma ceramides are used as useful biomarkers for metabolic dysfunction.

Several clinical studies have reported high levels of circulating ceramides in type 2 diabetes patients, and these levels were correlated with the severity of insulin resistance. These studies are supported by in vivo evidence that reveals that LDL particles containing ceramides are able to induce insulin resistance when administered to non-obese mice. Other studies have shown that total levels of ceramides are correlated with several parameters related to insulin resistance, as high circulating levels of TNFα and IL-6. It has been also observed that plasma ceramide levels subsequent to gastric bypass were lower, as well as TNFα plasma levels. These reductions were correlated with a dramatic improvement in sensitivity to insulin in these patients. Together, these studies help to establish a relationship among circulating ceramides, inflammation, and subsequent insulin resistance in different obesity and type 2 diabetes stages.

Insulin activity is mediated through the insulin receptor (IR), which propagates its activity via three pathways: 1) the phosphatidylinositol 3-kinase (PI3k), 2) the mitogen-activated protein kinase (MAPK), and 3) Cb 1 (CAP) associated protein. The first pathway (PI3k) is in charge primarily of glucose transportation, and it is significantly distorted by ceramides. The IR is a tyrosine-kinase receptor that has two extracellular a subunits and two β transmembrane subunits. After insulin binding to the a subunit of the receptor, the insulin receptor is subject to an autophosphorylation of tyrosine residues in the intracellular β domain.

The insulin receptor substrate (IRS) has a binding domain to phosphotyrosine that recognizes activated IR and leads to the phosphorylation of tyrosine and IRS activation. After several reactions, protein kinase B (PKB, also called AKT) is activated, and this promotes its relocation in the cytosol, causing the translocation of the glucose transporter GLUT4 in the plasma membrane. Lee J O et al., *J Biol Chem.* 287: 44121-9 (2012). This stimulates glucose uptake. AKT also phosphorylates and inactivates glycogen synthase-kinase-3 (GSK3), an enzyme involved in glycogen synthase inactivation. This results in an increase of glycogen storage. To summarize, insulin receptor activation (IR) leads to AKT activation, which, once activated, reduces plasma glucose by inducing cell glucose uptake, glycogen synthesis, and protein and fatty acid synthesis. AKT acts also by inhibiting gluconeogenesis. Ceramides cause insulin resistance by inhibiting AKT; similarly, they reduce GLUT4. Kramer H F et al., *J Biol Chem.* 281: 31478-85 (2006).

Macrophages are primarily known for their role in the immune system. Macrophage infiltration in adipose tissue in obesity plays a fundamental role in insulin resistance. As obesity progresses, macrophages change from an alternative activated anti-inflammatory phenotype (M2) to a more classically activated anti-inflammatory phenotype (M1). M1 macrophages produce a great number of pro-inflammatory cytokines, including TNFα, which may increase ceramides levels in several tissues. Ceramide function and role in macrophages has been subject of investigation in the past decade. Literature has addressed ceramides as mediators in several key physiological processes in macrophages. Biswas and Mantovani, *Nat Immunol.* 11: 889-896 (2010).

Adipose tissue was once considered a simple triglyceride reservoir, but it is now recognized as an active endocrine organ that plays an important role in insulin resistance pathogenesis associated with obesity. Although skeletal muscle tissue is the main player in peripheral glucose consumption, adipose tissue also expresses insulin receptors and is responsible for taking a portion of plasma glucose. TNFα, which is up-regulated in adipose tissue during obesity, may induce resistance to insulin by mitigating its signaling at the insulin receptor level and suppressing the expression of the glucose transporter that responds to insulin, GLUT4. It is believed that TNFα induces these effects by mediating ceramide synthesis. The resulting increase in intracellular ceramide levels correlates with a 60% decrease of GLUT4. Furthermore, it has been observed that 3T3-L1 adipocytes treatment with C8-ceramide (a ceramide analog) also reduces GLUT4, which suggests that there is a signaling pathway, initiated by ceramides in adipocytes, that plays a role in facilitating TNFα control in GLUT4 expression. Bogan J S et al., *Nature.* 425: 727-33 (2003).

Several clinical studies have reported that there are high ceramide serum levels in type 2 diabetes patients that correlate with the severity of insulin resistance. Galadari S. et al., *Lipids Health Dis.* 12: 98. doi: 10.1186/1476-511X-12-98 (2013). These correlated studies are supported by in vivo evidence that shows that LDL particles containing ceramides were capable of inducing insulin resistance when injected in slim mice. Insulin stimulus increased glucose uptake and reduced CERT-mediated ceramide transportation in L6 myotubes exposed to these ceramides. Other studies have demonstrated that total high ceramide levels correlate with several parameters involved in insulin resistance and an increase in pro-inflammatory cytokines, such as TNFα and interleukin-6. Additionally, it has been observed that a reduction in plasma ceramide levels and TNFa levels following a gastric bypass. This reduction correlated with a dramatic improvement in sensitivity to insulin in these patients. Together, these studies help to establish ceramides as central mediators in inflammation and insulin resistance in different obesity and type 2 diabetes stages.

It has been found that AMPK increases the activity of GPBP/CERT. In addition, GPBP/CERT and LKB1 boost in a synergic way their kinase activity.

Metformin Glycinate

Metformin glycinate inhibits the GPBP/CERT activity, e.g., the kinase activity of GPBP (e.g., FIGS. 6 and 7).

Metformin glycinate dissociates GPBP-LKB1 aggregates; it increases the activity of LKB1 (e.g., FIG. 14).

Metformin glycinate inhibits the cross activation of GPBP/CERT and LKB1 (e.g., FIG. 15).

Compared to metformin hydrochloride, metformin glycinate has a different modulation profile of immune response, especially with the migration of M1 to M2; it inhibits the synthesis of IL10. Metformin hydrochloride stimulates the synthesis of IL-10 (e.g., FIG. 17).

Metformin glycinate translocates GLUT4, the transporter of glucose, more efficiently than metformin hydrochloride does (e.g., FIGS. 19A and 19B; FIG. 19A shows the presence of SLN2 translocated GLUT4 while the presence of SLN1 failed to do so; FIG. 19B shows a model depicting the translocation pathway of GLUT4 by SLN1 and SLN2).

Metformin glycinate acts on an additional form, via the interaction of VAPA-VAMP2 (e.g., FIG. 18, which shows that the presence of SLN1 and SLN2 reduced colocalization of VAPA and VAMPs, the presence of SLN1 had a greater reduction effect).

Metformin glycinate participates in AS160 (Akt substrate 160 kDa) regulation (e.g., FIG. 16).

Metformin glycinate reduces blood glucose levels by an over-induction of the regulated vesicle secretion that results from the cooperation of three dependent synergistic mechanisms of the inhibition of the activity of kinase of GPBP: 1) over-activation of route LKB1-AMPK-AS160 due to the release of LKB1 from LKB1-GPBP aggregates; 2) activation of the insulin route by accumulation of the receiver in the plasma membrane and to resist the negative regulating effect that GPBP exerts over this route; and 3) activation of an auxiliary regulated vesicle secretion route dependent on dephosphorylated GPBP and VAPA.

Metformin glycinate (SLN2) but not metformin hydrochloride (SLN1) activates Akt. SLN2's effect on Akt is conditioned by GPBP levels. Thus reducing GPBP levels (e.g., protein and/or mRNA levels) or activity abolishes SLN2 activation of Akt. Since SLN2 inhibits GPBP autophosphorylation and its activity is associated with intracellular accumulation of dephosphorylated GPBP, dephosphorylated GPBP may act as an Akt activator while phosphorylated GPBP is an inhibitor. If the state of baseline GPBP phosphorylation of cell line is high, GPBP silencing would eliminate an Akt inhibitor, leading to this kinase activation. In contrast, if there were an equimolar mixture of phosphorylated and dephosphorylated GPBP in cells instead, silencing would be removing both Akt activators and inhibitors, which would have no net effect on Akt activation.

Moreover, phosphorylated GPBP acts as an AMPK inhibitor by retaining LKB1. GPBP dephosphorylation by SLN2 would turn an AMPK and Akt inhibitor (phosphorylated GPBP) into an Akt activator (dephosphorylated GPBP), releasing activated LKB1 and promoting dephosphorylated GPBP and GLUT4 co-transport to the VAPA dependent plasma membrane mode. Dephosphorylated GPBP would thus be involved directly in the co-GLUT4 translocation path to the plasma membrane and indirectly in the classic Akt and LKB1-AMPK routes.

Additionally, GPBP-1 silencing parallels silencing of all isoforms expressing the gene with respect to Akt activation but not with regard to the LKB1-AMPK activation. This highlights the potential GPBP isoform-2 participation in LKB1-AMPK activation so that GPBP-2 could be part of the retention system and SLN2 also inhibits its kinase activity.

The disclosure herein in no way limits the way the compound acts and/or achieves its effects in a subject, e.g., a human.

The disclosure will be further illustrated by the examples below.

EXAMPLES

Example 1

Treatment of Type 2 Diabetes Using Metformin Glycinate

This was a randomized, double blinded phase 2 clinical study of the effects of metformin glycinate (DMMET-01) on insulin sensitivity in naïve type 2 diabetes patients by Glucose CLAMP Technique. The aim of this study was to determine the effect of DMMET-01 on insulin sensitivity by Glucose CLAMP technique in Mexican type 2 diabetes patients, after 2 months of treatment.

Primary Outcome Measures: Insulin sensitivity.

Secondary Outcome Measures: Insulin, fasting glucose, HbA1c, Adverse Events, Creatinine, Total Cholesterol, HDL, Triglycerides, Uric acid, AST, ALT, FA, and DHL.

Inclusion Criteria

Ages eligible for study: 40 to 60 years
With type 2 diabetes evolution <5 years without pharmacological treatment 1 month prior to the screening
Fasting glucose=130-200 mg/dL
A1c of 7% to 9%
Blood pressure <140/80 mmHg
Ability to communicate and meet the requirements of the study
Signed Written Informed Consent before to conducting any study
Body mass index (BMI) of 25 kg/m² to 35 Kg/m²

Exclusion Criteria

Suspected or confirmed pregnancy
Nursing
Inability to secure the non-pregnant during the study duration
Hypersensitivity to any biguanides
Use of an investigational drug within 30 days prior to the screening
Liver failure, heart failure, kidney failure or thyroid disease
Periods of acute or chronic diarrhea or vomiting
Chronic hepatic disease
Total Cholesterol >300 mg/dL Methods Drug: DMMET-01
60 days: 30 days, dose of 1050.6 mg per day (before dinner) and 30 days, dose 1050.6 mg twice a day 30 more days (before breakfast before dinner).

Drug: Placebo
60 days: 30 days placebo once a day (before dinner)+30 days twice a day (before breakfast and before dinner).

Results: after two months treatment, the A1c level in the patient group who received DMMET01 reduced from 8.1±0.8 to 7.1±1.0% (p=0.008) (FIG. 1). In addition, a statistically significant percentage of patients achieved a reduction of more of 1% in the A1C in the DMMET-01 treatment group (FIG. 1). The treatment did not change the patients' sensitivity to insulin. No statistically significant difference in adverse events was observed in the placebo and the DMMET01 groups.

Conclusion: treatment with DMMET01 reduced the A1c level by more than 1% type 2 diabetes patients without modifying sensitivity to insulin in the patients. No statistically significant difference in adverse events was observed in patients in placebo and DMMET01 groups.

Example 2

Food Effects on Metformin Glycinate Administration

The impact of food on metformin glycinate administration was studied by comparing pharmacokinetic parameters after single administration of 1240 mg metformin glycinate after a breakfast rich in fats vs. 1240 mg metformin glycinate without food. Compared to administration without food, the administration after food intake increased $T_{max}$. The results are shown in Table 1 below. Based on the results, it is recommended to administer the medication while fasting due to the fact that food delays absorption.

TABLE 1

| The impact of food intake on metformin glycinate administration | | |
|---|---|---|
| | Metformin glycinate 1240 mg TD Median [minimum-maximum] | Metformin glycinate 1240 mg Median [minimum-maximum] |
| $t_{max}$ (h) | 2.5 [0.50-6.00] | 1.50 [0.50-4.00] |

1240 mg TD: administration with food.

Example 3

Efficacy Study of Metformin Glycinate on Postprandial Lipemia

This is a randomized, double blind phase 2 clinical trial to investigate the efficacy of metformin glycinate on patients' lipid profiles (e.g., TG, LDL, HDL). Patients will be randomized and assigned into one of the two treatment groups: metformin glycinate 1240 mg twice a day (BID) or metformin hydrochloride 1000 mg BID. The patients will be followed for 4 months.

Blood count, blood chemistry, liver profile, lipid profile, A1c, apolipoprotein B, oxidized LDL, fibroblast growth factor 21, leptin, adiponectin, C-reactive protein, free fatty acids, fibrinogen, Good pasture Binding Protein (GPBP) and antioxidant activity of plasma will be measured at baseline and 4 months. Additionally, after a structured meal, glucose, insulin, triglycerides, apolipoprotein B and oxidized LDL (baseline and 4 months) will be measured. Throughout the study adverse events will be documented.

Primary Outcome Measures: Change in postprandial lipemia at 4 months.

Secondary Outcome Measures: Change in oxidized LDL at 4 months, change in FGF-21 levels at 4 months, change in A1C at 4 months, change in alanine aminotransferase at 4 months, change in uric acid at 4 months, and number of participants with serious and non-serious adverse events.

Methods: Metformin glycinate (620 mg tablets of metformin glycinate): 1 tablet by mouth at night for 3 days, 1 tablet in the morning and evening for 3 days, 1 tablet in the morning and 2 tablets in the evening for 3 days and 2 tablets in the evening and 2 tablets in the morning until the end of the study.

Metformin hydrochloride (500 mg tablets of metformin hydrochloride):1 tablet by mouth at night for 3 days, 1 tablet in the morning and evening for 3 days, 1 tablet in the morning and 2 tablets in the evening for 3 days and 2 tablets in the evening and 2 tablets in the morning until the end of the study.

Example 4

Metformin Glycinate Inhibits IL-10 Expression in Macrophages Activated by LPS and INF-γ

RAW264.7 macrophage cells (a mouse macrophage cell line) were treated with 10 mM metformin hydrochloride (SLN1) or metformin glycinate (SLN2) for 2 hours. Afterwards LPS (0.5 µg/mL) and IFN-γ (20 ng/mL) were added to the culture media. Following different incubation times, cells were processed and the relative expression (RQ) of IL-10 was analyzed by reverse transcription polymerase chain reaction (RT-PCR) and quantitative PCR (qPCR), normalized against the expression of the hypoxanthine-guanine phosphoribosyltransferase gene (HPRT1). The expression level of IL-10 in non-stimulated cells was used as a reference (Time 0). The results are shown in FIG. 3. The area under the curve (AUC) for control, metformin hydrochloride and metformin glycinate is indicated in FIG. 3. The results show that metformin glycinate inhibits IL-10 expression in macrophages activated by LPS and INF-γ. On the other hand, metformin hydrochloride increased IL-10 expression in macrophages similarly treated.

Example 5

Metformin Glycinate Inhibits Growth of Cancer Cells

HeLa cells (a human cervical cancer cell line) were cultivated in DMEM medium supplemented with 10% SBF and penicillin/streptomycin for 20 h in absence (Cells) or presence of 10 mM metformin glycinate (SLN2), metformin hydrochloride (SNL1), or the corresponding vehicle. After the incubation, the cells were washed with PBS, collected and washed again, then fixed with methanol:acetone (50:50) for 16 h at −20° C., and stained with 10 µg/mL of propidium iodide, 0.01 mg/mL RNase, 0.01% sodium citrate, for 20 min at 37° C. in darkness. The stained cells were analyzed by flow cytometry using a BD FACS cell sorter and BD FACSuite™ software. The results are shown in FIG. 4. As shown in the figure, treatment with metformin glycinate resulted in about 56% of the cancer cells to enter G1 phase cell cycle arrest, which prevents the cells from dividing and spreading.

Example 6

Metformin Glycinate Reduces Fasting Serum Leptin Levels in IRS2 Knockout Mouse

Insulin receptor substrate 2 (IRS2) is a cytoplasmic signaling molecule that mediates effects of insulin, insulin-like growth factor 1, and other cytokines by acting as a molecular adaptor between diverse receptor tyrosine kinases and downstream effectors. Mice lacking IRS2 (e.g., IRS2 knockout mice) have a diabetic phenotype and increased serum leptin levels. Leptin is a hormone made by adipose cells that regulates appetite and inhibits hunger.

Female IRS2 knockout mice (KO) and their corresponding wild type controls (WT) were treated during 4 weeks with 100 mg/kg/day metformin glycinate (SLN2) or metformin hydrochloride (SLN1). The levels of fasting serum leptin, at the beginning and at the end of the treatments, were determined with a kit (Sigma) following the instructions by the manufacturer. The results are shown in FIG. 5 (the bars show the deviations for each group (n=3)). As shown in the figure, treatment with SLN2 reduced fasting serum leptin levels in the mice. In addition, compared to metformin hydrochloride, treatment with metformin glycinate resulted in a greater reduction of fasting serum leptin levels.

Example 7

Metformin Glycinate Inhibits GPBP/CERT Kinase Activity and Phosphorylation

Figure 6A:
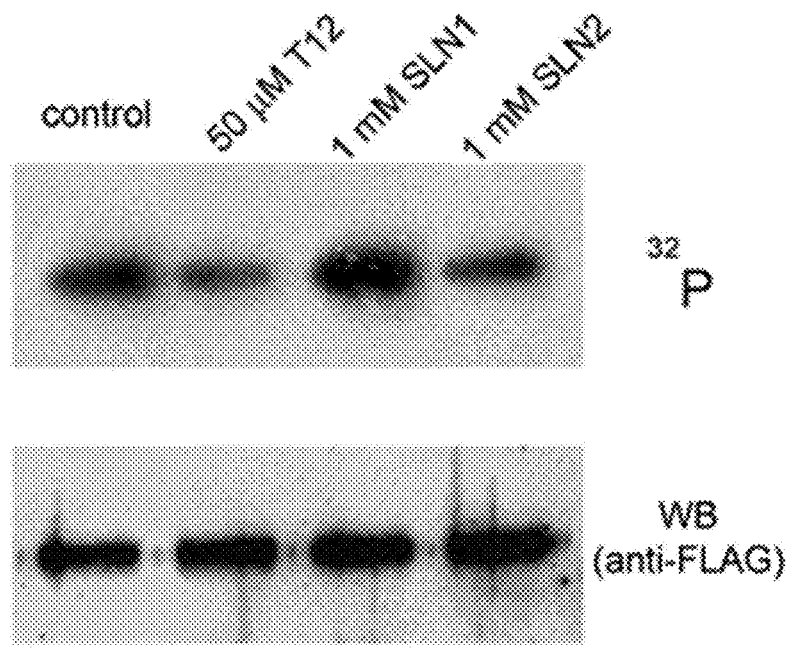
FIG. 6A shows metformin glycinate inhibition of GPBP auto-phosphorylation activity.

Recombinant FLAG-GPBP (expressed in *Pichia pastoris* (Invitrogen) and purified with anti-FLAG resin (Sigma)) were incubated in the absence (negative control) or presence of 50 µM T12 (a specific GPBP kinase inhibitor, positive control), 1 mM metformin hydrochloride, or 1 mM metformin glycinate, in a phosphorylation solution (final concentration: 25 mM β-glycerophosphate (pH 7.0), 0.5 mM EDTA, 0.5 mM EGTA, 8 mM $MgCl_2$, 5 mM $MnCl_2$, 1 mM DTT) without ATP for 10 min at room temperature (RT). Then [γ-$^{32}$P] ATP (Perkin Elmer) (final concentration of 0.132 µM) was added. The reaction mixtures (25 µl) were incubated at 30° C. with shaking (350 rpm) for 15 min, and then analyzed by SDS PAGE. The proteins were electrotransferred to a PVDF membrane (Immobilon P, Millipore). The membranes were subjected to autoradiography ($^{32}$P), and then detection with anti-FLAG antibodies (ECL Prime, GE Healthcare, WB anti-FLAG). The results are shown in FIG. 6A.

Figure 6B:
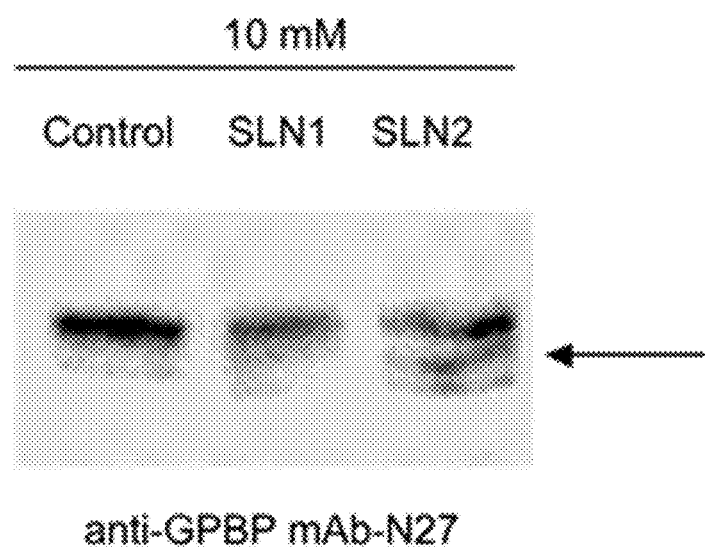
FIG. 6B shows that treatment with metformin glycinate resulted in GPBP dephosphorylation (shown by distinct mobility upon Western blotting analysis), which is indicative of a reduced GPBP kinase activity.

In a separate study, mouse C2C12 myoblasts were differentiated under low serum concentration conditions (DMEM supplemented with 2% horse serum and penicillin/streptomycin) for 3 days at 37° C. and treated for 3 h at the same temperature in the presence of 10 mM metformin hydrochloride, 10 mM metformin glycinate, or with the vehicle (control). The cells were lysed in a lyse buffer (50 µM Tris-HCl, 150 µM NaCl, 1% Triton X-100, 1 µM phenylmethylsulphonylfluoride (PMSF) and 10 µg/mL leupeptin) for 30 min at 4° C. Lysates were centrifuged at 16000× g for 5 min at 4° C. and the total protein concentration of the supernatants determined with the Bradford reagent (Bio-Rad). The samples were analyzed by Western blot using the anti-GPBP mAb-N27 and detected with chemoluminiscence (ECL Prime, GE Healthcare). The results are shown in FIG. 6B. The arrow indicates the dephosphorylated GPBP bands. As shown in the figure, more GPBP dephosphorylation resulted from the cells treated with metformin glycinate than that in the untreated cells or the cells treated with metformin.

Example 8

Metformin Glycinate Inhibits GPBP Phosphorylation

3T3-L1 cells were differentiated for 9 days under the following conditions: 3T3-L1 pre-adipocytes were cultured to confluence in DMEM supplemented with 10% calf serum. Two days after reaching confluence (day 0), cells were cultured for 2 days in DMEM supplemented with 10% fetal bovine serum (FBS), 1 µM dexamethasone, 2 µM rosiglitazone, 167 µM insulin and 115 mg/mL 3-isobutyl-1-methylxanthine (IBMX), and for 2 additional days in DMEM supplemented with 10% FBS and 167 nM insulin. Then culture media were changed to DMEM with 10% FBS and were renewed every 2 days until day 9. The cells were treated with 1 mM metformin glycinate or metformin hydrochloride during the last 24 h. Cells were washed with PBS and collected in 8M urea supplemented with 1× Halt protease and phosphatase inhibitor cocktail (Thermo Fisher Scientific), frozen at −80° C., thawed and centrifuged (16,000× g, 10 min, 4° C.). Supernatants (1.2 mL) were precipitated with trichloroacetic (TCA) to the final concentration of 10%, incubated 16 h at 4° C. and centrifuged. The precipitated material was washed 2 times with cold acetone, dried with speed-vac and resuspended in 8 M urea with stirring (1 h). Urea was diluted to 2 M with water and the resulting solutions filtered to remove non-solubilized material. The protein concentration was determined and DTT and alkylated with iodoacetamide were added to each sample (50 µg). Thereafter the urea concentration was adjusted to 1 M and the sample was trypsinized for 16 h at 37° C. The digested samples were dried with speed-vac and resuspended in 0.1% trifluoroacetic (TFA) for analysis by LC-MS.

In the LC-MS analysis, the peptides were concentrated with a precolumn C18 Acclaim PepMap 100 microns×2 cm (Thermo Fisher Scientific) using a nanoLC 425 (Eksigent Technologies) and eluted and separated sequentially using a C18 column Acclaim PepMap RSLC 75 microns×25 cm, with particle size of 2 microns (Thermo Scientific, P/N 164536). The flow rate of the Nano pump was set at 250 nL/min and a gradient was performed during 2 hours. The composition of phase A was 0.1% formic acid (FA) in water and phase B was 0.1% FA in acetonitrile. The ionization of the peptides was performed by infusion using a PicoTip emitter and an internal diameter of 10 µm (New Objective, Woburn, MA, USA) with a voltage of 2600 V at 75° C. and using a nanospray source III (Sciex). The mass spectrometric analysis was performed with a TripleTOF 5600+ (Sciex) using the Analyst TF v1.6 software. The spectra were acquired during the 2 hours chromatography period with an accumulation time for 250 ms TOF MS with mass range 350-1250 units m/z. Fragmentation of all ions of interest was performed throughout the chromatography with an accumulation time optimized according to the number of ions to fragment to achieve a cycle time not exceeding 3 seconds, high sensitivity mode and a mass range of 230-1500 units of m/z. The amounts of peptide 130-152 of Gpbp phosphorylated in three residues were quantified and represented with a histogram. The results are shown in FIG. 7 (Means±SEM). Treatments and analysis were performed in duplicate (N=2). Metformin glycinate (SLN2), but not metformin hydrochloride (SLN1) reduced the amount of triple phosphorylation (FIG. 7).

Example 9

Metformin Glycinate Reduces Ceramide Levels

3T3-L1 cells expressing GPBP or CERT with or without EYFP (Enhanced Yellow Fluorescent Protein) fusion were differentiated for 12 days as follows: 3T3-L1 pre-adipocytes were cultured to confluence in DMEM supplemented with 10% calf serum. Two days after reaching confluence (day 0), the cells were cultured for 2 days in DMEM supplemented with 10% fetal bovine serum (FBS), 1 µM dexamethasone, 2 µM rosiglitazone, 167 nM insulin and 115 µg/mL 3-isobutyl-1-methylxanthine (IBMX), and for 2 additional days in DMEM supplemented with 10% FBS and 167 nM insulin. Then culture media were changed to DMEM with 10% FBS and were renewed every 2 days until day 12. The cells were treated with metformin glycinate (SLN2) or metformin hydrochloride (SLN1) (1 mM each) during the last 48 h. Next, the cells were treated with trypsin and washed three times with 10 mL of PBS. The C16:0 ceramide content was determined by liquid chromatography and mass spectrometry (LC-MS) using a 1290 Infinity Series LC coupled to Triple Quad iFunnel 6495 MS/MS (Agilent Technologies). With 1/10 of each culture a protein extract in TBS supplemented with 1% Triton X-100, 0.1% SDS and 1× Halt Phosphatase Inhibitor and Protease™ Cocktail (Thermo Fisher Scientific) was made. The ceramide C16:0 content was measured and normalized vs. amount of total protein. The results are shown in FIG. 8 with means and standard errors of the means (n=2) shown.

Example 10

Accumulation of the Insulin Receptor Subunit β on the Plasma Membrane After Treatment with Metformin Glycinate C2C12 cells were differentiated to myotubes for 5 days in DMEM supplemented with 2% horse serum, then treated for 3 h with 10 mM metformin glycinate, 10 mM metformin hydrochloride, or with vehicle (control) at 37° C. Next, cells were washed with PBS and their membrane proteins were extracted. The content of insulin receptor (IRβ) was analyzed by Western blot with specific subunit β antibodies and the results are shown in FIG. 9. As shown in the figure, treatment with metformin glycinate (SLN2) resulted in significantly more accumulation of IRβ on the cell membrane than treatment with metformin hydrochloride (SLN1).

Example 11

Treatment with Metformin Glycinate Reduces Pro-inflammatory Cytokines

Palmitate is a saturated fatty acid that simulates an experimental obese state. It can be used as a pro-inflammatory stimulant for cytokines such as proIL-1β, TNFα, iNOS, IL-6, MCP-1 and IL-12.

Differentiated L1 adipocytes were treated for 24 h with palmitate (500 µM) in the presence or absence of the metformin hydrochloride (SLN1) or metformin glycinate (SLN2) (10 mM). Next, the relative expression of inflammation markers was analyzed by RT and qPCR using HPRT-1 as a normalizer and the untreated cell expression levels as a reference (for MCP-1 and IL-12) or those treated palmitate. After the treatments, culture media were collected and subsequently analyzed, cells were washed with PBS, and RNA was extracted (illustra RNAspin Mini, GE Healthcare) and reverse transcribed (High Capacity cDNA Reverse Transcription Kit, Life Technologies). The expression of the genes that were the object of the study was analyzed by qPCR using specific probes (TaqMan® Gene Expression Assays, Life Technologies). The relative expression (RQ), represented in the figure, was calculated by the AACt method. The results are shown in FIG. 10.

As shown in FIG. 10, metformin hydrochloride and metformin glycinate attenuated the inflammatory response of palmitate-stimulated adipocytes, but metformin glycinate is significantly more effective than metformin hydrochloride. These anti-inflammatory effects correlated with the in vitro inhibitory activity on GPBP suggesting that this kinase activity mediates in the pro-inflammatory response induced by palmitate.

Example 12

Metformin Glycinate Decreased Hyperglycemic Levels of in C2C12 Myotubes Induced by M1 Macrophage Conditioned Media There is considerable evidence showing that inflammation and hyperglycemia are interconnected: inflammation induces hyperglycemia and reciprocally hyperglycemia induces inflammation with the molecular bases not elucidated yet. To explore the participation of GPBP, glucose intake under normoglycemic conditions with conditioned media generated by macrophages differentiated to a proinflammatory M1 phenotype was monitored.

In the experiments, RAW264.7 macrophages were treated with metformin hydrochloride (SLN1) or metformin glycinate (SLN2) (10 mM) for 2 h and then stimulated with LPS (0.5 µg/mL) and IFNγ (20 ng/mL) for 16 h. Then the culture media were collected, their glucose concentration adjusted to 100 mg/100 mL and were used to culture C2C12 myoblasts that had been previously differentiated to myotubes in DMEM supplemented with 2% horse serum for 5 days. The glucose concentration of the myotube cultures was determined at different times with Glucocard (Arkray). The controls used were the C2C12 cultured with media conditioned with no stimulated macrophages (Cells) or with M1 conditioned media (M1). The initial glucose levels (time 0) were used as a reference (100%) in each series. The results are shown in FIG. 11.

As shown in FIG. 11, hyperglycemic levels were induced in myotubes grown in a proinflammatory M1 macrophage-derived conditioned media. Treatment with metformin glycinate, but not metformin hydrochloride, reduced the hyperglycemic levels. In other words, whereas metformin hydrochloride slowed down the progression towards hyperglycemia, metformin glycinate maintained values at normoglycemic levels. These results are consistent with the GPBP inhibition capacity, revealing that the metabolic response to soluble hyperglycemic factors released by proinflammatory macrophages can effectively be modulated by GPBP specific inhibitors.

Example 13

Glycemic Levels and Appetite in C57BL/6 Mice and Fasting Glycemia and Insulinemia in IRS2-/- Mice Treated with Metformin Hydrochloride or Metformin Glycinate Insulin resistance characterizes type 2 diabetes, obesity, and the metabolic syndrome. Thus, insulin sensitivity is a major therapeutic objective for these metabolic diseases. Insulin receptor substrate (IRS) proteins regulate the physiological actions of insulin upon binding to the receptor. Specific deletion of IRS2 in mice produces diabetes due to a developmental reduction of the pancreatic β-cell mass and the inability of existing β-cells to expand in response to peripheral insulin resistance. Additionally, IRS2-deficiency in mice causes hepatic insulin resistance concurrent with failed suppression of hepatic glucose production. While male IRS2-/- mice often die of diabetic complications by 12 weeks of age, females IRS2-/- mice develop a milder form of diabetes and many live up to 6 months. The observation that female IRS2-/- mice eat more than controls led to the discovery that this molecule is critical for hypothalamic regulation of food intake. Interestingly, the expression of human IRS2 is significantly reduced in islets obtained from patients with type 2 diabetes compared to controls, demonstrating that IRS2 likewise exerts an essential role in the development of diabetes in humans.

In this experiment, C57BL/6 mice were either not treated with any drugs and on an unrestricted diet (control) or treated with metformin hydrochloride (SLN1) or metformin glycinate (SLN2) (100 mg/kg/day) mixed with solid food for 1 week. The mean glycemic values at the beginning and end of the experiment are represented for each group (n=3) with their standard deviations. The differences between the values at the beginning and the end were significant in the groups treated with metformin hydrochloride (P<0.05) and metformin glycinate (P<0.01), according to the corresponding paired Student's t-tests (FIG. 12A). Relative daily dietary intake of the mice used in was determined and shown in FIG. 12B.

In addition, female IRS2-/- (KO) mice, aged 10-12 weeks, and their corresponding controls (WT) were treated for 4 weeks with metformin hydrochloride or metformin glycinate (100 mg/kg/day), and their fasting glycemic levels were determined using Glucocard before and after the treatment. The mean glycemic values are represented per group (n=3) pre-treatment (black bars) and post-treatment (gray bars) along with their standard deviations. An asterisk (*) denotes statistically significant differences (P<0.05) among the indicated groups according to the Student's t-test (FIG. 12C). Also, female IRS2-/- (KO) mice and their corresponding controls (WT) were treated for 4 weeks with metformin hydrochloride or metformin glycinate (100 mg/kg/day) mixed with solid food, as previously indicated. The fasting serum insulin levels taken pre-treatment (black bars) and post-treatment (gray bars) were determined using a kit (Millipore), following the manufacturer's instructions. Mean values and standard deviations are presented for each group (n=3) (FIG. 12D).

As shown in FIG. 12A, metformin hydrochloride and to a greater extent metformin glycinate, significantly reduced glycemia with statistical significance. As expected, food intake was greater in mice treated with metformin hydrochloride and metformin glycinate compared to untreated mice (FIG. 12B).

Subsequently, 10-12-week-old IRS2-/- female mice (KO) with fasting glycemia levels of 90-110 mg/dL (pre-diabetic stage) were treated with metformin hydrochloride or metformin glycinate at 100 mg/kg/day (administered with food for 4 weeks). After treatment, the fasting glycemia rates of untreated mice reached the typical values of diabetic stage. In contrast, in the mice treated with metformin glycinate, the fasting glycemia levels post-treatment were significantly lower than those pre-treatments. In the metformin hydrochloride treated mice, fasting glycemia post-treatment was slightly lower, though not statistically significant compared to control (FIG. 12C).

Due to peripheral resistance to insulin, the IRS2-/- mice also develop hyperinsulinemia. Treatment with metformin glycinate (100 mg/kg/day) during 4 weeks lowered the fasting insulin levels in female IRS2-/- mice. Conversely, final fasting insulinemia in untreated mice or treated with metformin hydrochloride was higher than at the initiation of the experiment (FIG. 12D). These results suggest that metformin glycinate, but not metformin hydrochloride, reduced resistance to insulin in peripheral tissues in diabetic mice.

All together, the results indicate that peripheral resistance to insulin in female IRS2-/- mice was mediated, at least in part, by GPBP activity since an inhibitor of GPBP kinase (metformin glycinate), but not a compound without this activity (metformin hydrochloride), was capable of offsetting it. This is in agreement with the observation that metformin glycinate is more effective than metformin hydrochloride in lowering hyperglycemia in female IRS2-/- mice, and is consistent with the observation that levels of activated Akt (phosphorylated in Thr308) in mice myoblasts GPBP-deficient (Gpbp-1-/-) were higher than in the control myoblasts.

Example 14

Metformin Association with Glycine in an Aqueous Solution

Results from this example support that glycine forms stable complexes with metformin in aqueous solutions.

An aqueous glycine solution with a known concentration was evaluated with an increasing amount of metformin to determine the formation of metformin glycinate complexes. The generation of stable metformin glycinate complexes was quantified by the variation of proton signal displacement by nuclear magnetic resonance (NMR). The alpha protons signal of the glycine (singlet at 3.56 ppm) shifted towards higher δ values as the amount of metformin increased, suggesting a direct interaction between glycine and metformin (not shown). The formation of metformin glycinate complexes was analyzed using the WINEQNMR2 program, which calculates the association constants by adjusting the real chemical displacement according to the concentrations of the components. FIG. 13 was obtained when considering a 2:1 complex (2 molecules of metformin for 1 of glycine). The complexation constant was calculated to be 712±19.

Example 15

Safety and Efficacy of Metformin Glycinate vs. Metformin Hydrochloride on Metabolic Control and Inflammatory Mediators in Type 2 Diabetes Patients This is a randomized, double blind, phase 3 clinical trial. There are 2-parallel groups.

Number of subjects: 200 patients aged between 18 and 70 of both sexes will be recruited.

Objective: To compare the efficacy and safety of treatment with metformin glycinate at 1050.6 mg dose and metformin hydrochloride at 850 mg dose for 12 months in recently diagnosed patients with type 2 diabetes, with no pharmacological treatment or previously treated; additionally, to compare the effect of treatment on the concentration of inflammatory mediators, adipocytokines, and adhesion molecules.

Specific Objectives

1. To compare HbA1c concentration after 12 months of treatment with Metformin glycinate in doses of 2101.2 mg/day with a group treated with metformin hydrochloride in doses of 1700 mg/day, in patients with type 2 diabetes.
2. To compare fasting plasma glucose concentration, after 12 months of treatment with metformin glycinate in doses of 2101.2 mg/day with a group treated with metformin hydrochloride in doses of 1700 mg/day, in patients with type 2 diabetes.
3. To compare concentrations of total cholesterol, its LDL and HDL fractions, and triglycerides, after 12 months of treatment with metformin glycinate in doses of 2101.2 mg/day with a group treated with metformin hydrochloride in doses of 1700 mg/day, in patients with type 2 diabetes.
4. To know the frequency of adverse events, after 12 months of treatment with metformin glycinate in doses of 2101.2 mg/day, compared with a group treated with metformin hydrochloride in doses of 1700 mg/day, in patients with type 2 diabetes.
5. To compare concentrations of TNF-α, adiponectin, resistin, IL-10, and soluble adhesion molecules, such as ICAM-1 and VCAM-1, after 12 months of treatment with metformin glycinate in doses of 2101.2 mg/day, with a group treated with metformin hydrochloride in doses of 1700 mg/day, in patients with type 2 diabetes.
6. To compare malondialdehyde and superoxide dismutase concentrations, after 12 months of treatment with metformin glycinate in doses of 2101.2 mg/day with a group treated with metformin hydrochloride in doses of 1700 mg/day, in patients with type 2 diabetes.

Example 16

SLN2 Alters GPBP Aggregation State

HeLa cells, cultured in DMEM, supplemented with 10% fetal bovine serum (FBS), and penicillin/streptomycin, were treated or not (control) with SLN1 or SLN2 1 mM for 24 h. After treatment, cells were washed with PBS, collected with a cell scrapper in PBS, and centrifuged (1850× g, 10 min, 4° C.). Subsequently, cell precipitates were dispersed in five volumes of hypotonic solution (10 mM HEPES, pH 7.9, 1.5 mM $MgCl_2$, 10 mM KCl, 0.2 mM PMSF, 0.5 M DTT), centrifuged (1850× g, 5 min, 4° C.), and then dispersed again in 3 volumes of hypotonic solution and stored in ice for 10 min. Cells were then lysed with a Dounce homogenizer (18 pestle movements) and centrifuged (3300× g, 15 min, 4° C.). Supernatants (cytoplasmic fraction) were put into a concentrated solution (10×) of 30 mM HEPES, pH 7.9, 140 mM KCl, 0.3 mM $MgCl_2$, and centrifuged for 1 h at 100,000× g. Supernatants were dialyzed against 50 volumes of dialysis solution (20 mM HEPES, pH 7.9, 20% glycerol, 100 mM KCl, 0.2 mM EDTA, 0.2 mM PMSF, 0.5 M DTT), cleared (25000× g, 20 min, 4° C.), and concentrated (Microcon 10K). Then, protein concentration was determined (Bio-Rad) and samples were stored at −80° C. Similar extract quantities were analyzed via gel filtration, using a Superdex 200 column, balanced with PBS (5 GE Healthcare), and a Hitachi HPLC device, collecting fractions of 500 μL. Equivalent fraction volumes were analyzed via Western blots with anti-GPBP N27-HRP antibodies. The results are shown in FIG. 14. In this Figure, bars and numbers show location and size in kDa of molecular weight standards used in electrophoresis. The arrow indicates high molecular weight aggregates formed in cultures treated with SLN2 which were not present in cultures treated with SLN1.

Example 17

SLN2 Inhibits Cross Activation of GPBP/CERT, Increases AS160 Phosphorylation in the Presence of GPBP, AMPK, and AKT Two hundred nanograms of AS160 (Origene Technologies) was incubated either in the absence (−) or in the presence (+) of FLAG-GPBP (270 ng), AKT (Millipore) (200 ng) and SLN1 or SLN2 (5 mM) in phosphorylation solution (β-glycerophosphate 25 mM (pH 7.0), EDTA 0.5 mM, EGTA 0.5 mM, $MgCl_2$ 8 mM, $MnCl_2$ 5 mM, DTT 1 mM) without ATP for 10 min at RT, after which [γ-$^{32}$P] ATP (Perkin Elmer) (0.132 μM) and ATP (Sigma) (100 μM) were added. Reaction cocktails (25 μl) were incubated at 30° C. for 15 min, and stirred (350 rpm). Then, they were analyzed by Western blot and autoradiography (FIG. 15), and revealed using antibodies (not shown) to identify phosphorylated polypeptides (arrows). Metformin glycinate (SLN2) counteracted GPBP and AKT cross activation.

In a separate experiment, two hundred nanograms of AS160 (Origene Technologies) was incubated either in the absence (−) or in the presence (+) of FLAG-GPBP (270 ng), AKT (Millipore) (200 ng), AMPK (Millipore) (200 ng), and SLN1 or SLN2 (5 mM), or T12 (50 µM) (a GPBP inhibitor) in phosphorylation solution (β-glycerophosphate 25 mM, pH 7.0, EDTA 0.5 mM, EGTA 0.5 mM, $MgCl_2$ 8 mM, $MnCl_2$ 5 mM, DTT 1 mM), without ATP for 10 min at RT, after which [γ-$^{32}$P] ATP (Perkin Elmer) (0.132 µM) and ATP (Sigma) (100 µM) were added. The reactions (25 µL) were carried out at 30° C., and stirred (350 rpm) for 15 min. Then, they were stopped with a reducing loading buffer, heated (95° C., 2 min), and analyzed using electrophoresis, electrotransfer, and autoradiography. The results are shown in FIG. 16. As shown in FIG. 16, phosphorylation of AS160 increased in the presence of SLN2. On the other hand, the addition of SLN1 (metformin hydrochloride) inhibited AS160 phosphorylation similar to the inhibitor T12.

Example 18

GPBP-1 Expression is Required for IL-1 Beta and IL-10 Expression and Secretion to Extracellular Media SL2, which inhibits GPBP-1, inhibits the expression of IL-10.

Furthermore, metformin glycinate acts via the interaction of VAPA-VAMP2. As shown in FIG. 18, the presence of SLN1 and SLN2 reduced colocalization of VAPA and VAMPs, while the presence of SLN1 had a greater reduction effect. Moreover, FIG. 19A shows that metformin glycinate translocates GLUT4 more efficiently than metformin hydrochloride, and FIG. 19B shows a model depicting the pathways of metformin glycinate and metformin hydrochloride in translocating GLUT4.

Example 19

Body Weight Measurements in IRS2 Knockout Mice Treated with Metformin Hydrochloride or Metformin Glycinate IRS2 knockout mice (KO IRS2) and their corresponding wild type controls (WT) were treated with 100 mg/kg/day metformin glycinate (SLN2) or metformin hydrochloride (SLN1). Body weight of the mice was measured prior to the onset of treatment, at 4 weeks after treatment, and at 8 weeks after treatment. There were 8 mice in each group at the pre-treatment and 4-week treatment time points. At the 8-week treatment time point, there were 8 mice in each of the WT groups, 6 mice in the KO IRS2 untreated control group, 7 mice in the KO IRS2 SLN1 treated group, and 8 mice in the KO IRS SLN2 treated group. FIG. 20 shows that the average body weight of KO IRS2 mice treated with SLN2 was significantly lower after 8 weeks than before treatment. Pre-treatment body weight was not significantly different from post-treatment in KO IRS2 mice treated with SLN1, and no differences were noted between KO IRS2 receiving SLN1 and control KO IRS2 at the end of the 8-week study period. Statistical differences between the experimental groups shown in FIG. 20 were assessed by Student's T test. P value of <0.05 is indicated by *.

Example 20

Serum Triglyceride Measurements in IRS2 Knockout Mice Treated with Metformin Hydrochloride or Metformin Glycinate IRS2 knockout mice (KO IRS2) and their corresponding wild type controls (WT) were treated with 100 mg/kg/day metformin glycinate (SLN2) or metformin hydrochloride (SLN1) and their serum triglycerides (TG) were measured at 8 weeks after treatment. At the 8-week treatment time point, there were 8 mice in each of the WT groups, 6 mice in the KO IRS2 untreated control group, 7 mice in the KO IRS2 SLN1 treated group, and 8 mice in the KO SLN2 treated group. Blood was collected at the time of sacrifice and used to measure TG under fasting conditions. Due to the presence of insulin resistance, circulating TG in the untreated KO IRS2 was higher than untreated controls (FIG. 21, p<0.05). Serum TG were lower in KO IRS2 treated with either SLN1 or SLN2 as compared to untreated KO IRS2. TG were also lower in WT mice treated with SLN2 as compared to untreated or SLN1-treated control mice. Statistical differences between the experimental groups shown in FIG. 21 were assessed by Student's T test. P value of <0.05 is indicated by *.

Example 21

Adipose Triglycerides are Lower in IRS2 Knockout Mice Treated with SLN2

IRS2 knockout mice (IRS2-/-) and their corresponding wild type controls (WT) were treated with 100 mg/kg/day metformin glycinate (SLN2) and their serum triglycerides (TG) were measured at 8 weeks after treatment. At the 8-week treatment time point, there were 6 mice in each treatment group. Adipose tissue was collected upon sacrifice and frozen in liquid $N_2$. Lipidomics analysis of the tissue was then performed using HPLC/MS. Triglycerides 16:0 and 18:1n-9c (nmol/mg of adipose tissue) were increased in all groups of IRS2-/- compared to the groups of WT mice (FIG. 22). However, 16:0 was significantly lower in IRS2-/- treated with SLN2 compared to control IRS2-/-, reaching levels similar to WT. Furthermore, levels of 18:1n-9c in adipose tissue were drastically reduced in IRS2-/- mice treated with SLN2 when compared to control IRS2-/-. Statistical differences between the experimental groups shown in FIG. 22 were assessed by Student's T test. P value of <0.01 is indicated by **.

Example 22

Pharmacokinetic Profile of Metformin Glycinate

The pharmacokinetic profile of metformin glycinate was evaluated in healthy volunteers in a two-stage, open, random and crossed clinical trial using metformin glycinate 620 mg (A), metformin glycinate 1240 mg (B), metformin glycinate 2480 mg (C), and metformin hydrochloride 1000 mg (D) after single and multiple doses and after food intake.

More specifically, administration of a single dose of metformin glycinate 620 mg, 1240 mg, or 2480 mg was tested (Stage A), as well as administration of metformin glycinate 620 mg in multiple doses for 8 days (Stage B). Administration of metformin glycinate 1240 mg while the subject was fasting and after ingesting a breakfast high in fats (E) was also tested.

A total of 49 subjects, both sexes, were randomized. Twenty five volunteers went through Stage A (13 men and 12 women) and 24 volunteers (12 men and 12 women) in Stage B. All of them completed the study.

Stage A: Every subject received a single dose of each studied treatment during 5 experimental sessions with a minimum lavage period of 6 days in between treatments and a follow-up of up to +36 hours.

Stage B: All the subjects received multiple doses of each treatment during 2 experimental sessions of 8 days with a minimum lavage period of 6 days in between treatments and a follow-up of up to +36 hours.

The following parameters were calculated: t½, Cmax, Tmax, $AUC0^t$, AUC0∞, extrapolated % of AUC, Vd/F, Cl/F in both stages (A and B) and t½ ss, Cmaxss, Tmaxss, $AUC0^{12}$, AUC0∞, Vss, Clss/F, Cminss, % FTP and % of balance in stage B, and Emax.

Results

Stage A

The pharmacokinetic parameters obtained in the formula test (metformin glycinate) and reference (metformin hydrochloride) were similar for the metformin glycinate 1240 mg dose. The confidence intervals of the parameters obtained in the study are summarized in Table 2.

TABLE 2

| C.I. 90% (n = 25) | Metformin (A-D) | Metformin (B-D) | Metformin (C-D) | Metformin (E-B) |
| --- | --- | --- | --- | --- |
| Ln Cmax (µg · h/mL) | 108.75-128.06 | 95.78-118.57 | 83.68-100.96 | 64.80-78.95 |
| Ln $AUC_0^t$ (µg · h/mL) | 119.16-133.99 | 98.11-115.03 | 75.52-87.93 | 76.09-92.49 |
| Ln Cmax (µg · h/mL) | 108.75-128.06 | 95.78-118.57 | 83.68-100.96 | 64.80-78.95 |
| Ln $AUC_0^\infty$ (ng/mL) | 118.89-133.10 | 97.87-114.49 | 75.71-88.15 | 76.28-92.26 |

The pharmacokinetic parameters of bioavailability in velocity (Ln Cmax) for metformin showed statistically significant differences attributed to the formula factor:
Metformin glycinate 620 mg in comparison with metformin hydrochloride 1000 mg.
Metformin glycinate 1240 mg vs metformin glycinate 1240 mg after intake of a breakfast rich in fats.

The pharmacokinetic parameters of bioavailability in magnitude (Ln AUCt0) for metformin showed statistically significant differences attributed to the formula factor:
Metformin glycinate 620 mg and metformin hydrochloride 2480 mg in comparison with metformin hydrochloride 1000 mg.
Metformin glycinate 1240 mg vs metformin glycinate 1240 mg after intake of a breakfast rich in fats.

No statistically significant differences were detected that were attributed to the sequence and period factors after analysis through ANOVAs of repeated measures.

The pharmacokinetic parameters of bioavailability in magnitude (Ln AUC0∞) for metformin showed statistically significant differences attributed to the formula factor:
Metformin glycinate 620 mg and metformin glycinate 2480 mg in comparison with metformin hydrochloride 1000 mg.
Metformin glycinate 1240 mg vs metformin glycinate 1240 mg after intake of a breakfast rich in fats.

No statistically significant differences were detected that were attributed to the sequence and period factors after analysis through ANOVAs of repeated measures. No statistically significant differences were observed between metformin glycinate 1240 mg and metformin hydrochloride 1000 mg.

In the comparative analysis of Tmax between the different doses of metformin glycinate and metformin hydrochloride, statistically significant differences were observed between metformin glycinate 2480 mg and metformin hydrochloride 1000 mg.

90% of the calculated Confidence Intervals (C.I.) for Cmax, AUCt0 and AUC0∞ were not within the theoretical framework of bioequivalence (80%-125%) for:
Metformin glycinate 620 mg that shows a slight suprabioequivalence regarding metformin hydrochloride 1000 mg.
Metformin glycinate 1240 mg vs metformin glycinate 1240 mg after intake of a breakfast rich in fats, which showed infrabioequivalence when administered after breakfast.

90% of the calculated Confidence Intervals (C.I.) for Cmax, AUCt0 and AUC0∞
were not within the theoretical framework of bioequivalence (80%-125%) for:
Metformin glycinate 2480 mg showing infrabioequivalence vs a Metformin hydrochloride 1000 mg.

90% of the Confidence Intervals (C.I.) calculated for the pharmacokinetic parameters in magnitude as well as velocity for metformin glycinate 1240 mg against metformin hydrochloride 1000 mg were within the theoretical ranges of bioequivalence.

The results of the kinetic proportionality evaluation for metformin glycinate 620 mg, 1240 mg and 2480 mg indicate the existence of a good linear correlation between pharmacokinetic parameters and the three metformin doses.

Stage B

The pharmacokinetic parameters obtained in the formula test (metformin glycinate) and reference (metformin hydrochloride) were similar.

The confidence intervals (C.I.) of the parameters obtained in the study for metformin are summarized in Table 3.

TABLE 3

| C.I. 90% (n = 24) | Metformin |
| --- | --- |
| Ln Cmax (µg · h/mL) | 97.73-117.55 |
| Ln Cmin (µg · h/mL) | 89.73-117.58 |
| Ln $AUC_0^t$ (µg · h/mL) | 91.78-107.50 |
| Ln $AUC_0^{12}$ (µg · h/mL) | 92.39-108.81 |
| Ln $AUC_0^\infty$ (ng/mL) | 91.39-106.36 |

The pharmacokinetic parameters of bioavailability in velocity (Ln Cmax) for metformin did not show statistically significant differences attributed to the formula, period and sequence factors after analysis with ANOVAs of repeated measures.

The pharmacokinetic parameters of bioavailability in velocity (Ln Cmin) for metformin did not show statistically significant differences attributed to the formula, period and sequence factors after analysis with ANOVAs of repeated measures.

The pharmacokinetic parameters of bioavailability in magnitude (Ln AUCt), (Ln AUC12) and (Ln AUC0) for metformin did not show statistically significant differences attributed to the formula, period and sequence factors after analysis with ANOVAs of repeated measures.

The comparative analysis of Tmax showed statistically significant differences between metformin glycinate 620 mg BID and metformin hydrochloride 1000 mg BID.

90% Confidence Intervals (C.I.) calculated for the pharmacokinetic parameters in magnitude as well as velocity for metformin glycinate 620 mg against metformin hydrochloride 500 mg were within the theoretical ranges of bioequivalence.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

What is claimed is:

1. A method of treating diabetes comprising the step of: administering to a subject in need thereof a therapeutically effective amount of metformin glycinate in combination with one or more additional antidiabetic agents selected from the group consisting of a sulfonylurea, a thiazolidinedione, a dipeptidyl peptidase 4 (DPP4) inhibitor, a sodium/glucose cotransporter 2 (SGLT2) inhibitor, a glucagon-like peptide-1 (GLP1) receptor agonist, glucagon like peptide-1 (GLP-1), and insulin.

2. The method of claim 1, wherein the metformin glycinate and the one or more additional antidiabetic agents are administered concurrently.

3. The method of claim 1, wherein the metformin glycinate and the one or more additional antidiabetic agents are administered rally.

4. The method of claim 2, wherein the metformin glycinate and the one or more additional antidiabetic agents are in the same dosage form.

5. The method of claim 1, wherein the metformin glycinate is administered once daily or twice daily.

6. The method of claim 1, wherein the treatment reduces the blood glycated hemoglobin (HbA1c) level in the subject to ≤7%.

7. A pharmaceutical composition, comprising:
   (i) metformin glycinate; and
   (ii) (a) one or more antidiabetic agents selected from the group consisting of a sulfonylurea, a thiazolidinedione, a DPP4 inhibitor, a SGLT2 inhibitor, a GLP1 receptor agonist, GLP-1, and insulin.

8. The pharmaceutical composition of claim 7, wherein the DPP4 inhibitor is present and is sitagliptin, saxagliptin, linagliptin, or alogliptin.

9. The pharmaceutical composition of claim 8, wherein the composition comprises from about 2.5 mg to about 100 mg of the DPP4 inhibitor.

10. The pharmaceutical composition of claim 7, wherein the thiazolidinedione is present and is rosiglitazone.

11. The method of claim 1, wherein the DPP4 inhibitor is present and is sitagliptin, saxagliptin, linagliptin, or alogliptin.

12. The method of claim 1, wherein the thiazolidinedione is present and is rosiglitazone.

13. The method of claim 1, wherein the sulfonylurea is present and is glimepiride, glipizide, or glyburide.

14. The method of claim 1, wherein the SGLT2 inhibitor is present and is canagliflozin or dapagliflozin.

15. The method of claim 1, wherein the one or more additional antidiabetic agents comprise insulin.

16. The pharmaceutical composition of claim 7, wherein the sulfonylurea is present and is glimepiride, glipizide, or glyburide.

17. The pharmaceutical composition of claim 7, wherein the SGLT2 inhibitor is present and is canagliflozin or dapagliflozin.

18. The pharmaceutical composition of claim 7, wherein the one or more additional antidiabetic agents comprise insulin.

* * * * *